(12) United States Patent
Kondo et al.

(10) Patent No.: US 6,329,027 B1
(45) Date of Patent: *Dec. 11, 2001

(54) CHLOROBENZENE DERIVATIVES, LIQUID-CRYSTAL COMPOSITION, AND LIQUID-CRYSTAL DISPLAY ELEMENTS

(75) Inventors: Tomoyuki Kondo; Shuichi Matsui; Kazutoshi Miyazawa; Hiroyuki Takeuchi; Fusayuki Takeshita; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/319,009

(22) PCT Filed: Nov. 27, 1997

(86) PCT No.: PCT/JP97/04329

§ 371 Date: May 28, 1999

§ 102(e) Date: May 28, 1999

(87) PCT Pub. No.: WO98/23561

PCT Pub. Date: Jun. 4, 1998

(30) Foreign Application Priority Data

Nov. 28, 1996 (JP) .................................................. 8-332766

(51) Int. Cl.⁷ .......................... C09K 19/30; C09K 19/12; C07C 25/13; C07D 239/02; C07D 309/00; C07D 319/06; C07D 213/00

(52) U.S. Cl. ................ 428/1.1; 252/299.63; 252/299.66; 544/242; 544/335; 544/336; 546/1; 549/356; 549/369; 549/377; 556/406; 570/127; 570/129; 570/144

(58) Field of Search .......................... 252/299.63, 299.66; 570/127, 129, 144; 428/1.1; 544/242, 298, 335, 336; 546/1; 549/369, 377, 356; 556/406

(56) References Cited

U.S. PATENT DOCUMENTS

| | | | |
|---|---|---|---|
| 4,368,135 | 1/1983 | Osman | 252/299.63 |
| 4,551,264 | 11/1985 | Eidenschink et al. | 252/299.62 |
| 5,230,826 | 7/1993 | Boller et al. | 252/299.61 |
| 5,292,452 | 3/1994 | Buchecker et al. | 252/299.61 |
| 5,523,440 | * 6/1996 | Nakashima et al. | 556/406 |
| 5,641,431 | * 6/1997 | Kinsho et al. | 252/299.63 |
| 5,659,059 | 8/1997 | Ogihara et al. | 556/406 |
| 5,858,275 | * 1/1999 | Matsui et al. | 252/299.63 |
| 5,932,138 | * 8/1999 | Plach et al. | 252/299.66 |
| 5,948,319 | * 9/1999 | Tanaka et al. | 252/299.66 |
| 6,004,479 | * 12/1999 | Weber et al. | 252/299.63 |

FOREIGN PATENT DOCUMENTS

| | | |
|---|---|---|
| 4219819 | 12/1993 | (DE) . |
| 23728 | 5/1980 | (JP) . |
| 58-167528 | 10/1983 | (JP) . |
| 61-36251 | 2/1986 | (JP) . |
| 1-157925 | 6/1989 | (JP) . |
| 2-501311 | 5/1990 | (JP) . |
| 4-169573 | 6/1992 | (JP) . |
| 4-282355 | 10/1992 | (JP) . |
| 5-214342 | 8/1993 | (JP) . |
| 7-10787 | 1/1995 | (JP) . |
| 7-173176 | 7/1995 | (JP) . |

* cited by examiner

*Primary Examiner*—Shean C. Wu
(74) *Attorney, Agent, or Firm*—Wenderoth, Lind & Ponack, L.L.P.

(57) ABSTRACT

Provided are liquid crystalline compounds having excellent physical properties and being excellent in miscibility with other liquid crystal materials; liquid crystal compositions comprising the crystalline compound; and liquid crystal display device fabricated by using the liquid crystal composition;

the liquid crystalline compounds being specific chlorobenzene derivatives expressed by the general formula (1)

$$Ra-A_1-Z_1-A_2(-Z_2-A_3)_m-(Z_3-A_4)_n-Rb \quad (1)$$

wherein Ra, Rb, $A_1$ to $A_4$, $Z_1$ to $Z_3$, m, and n are herein defined.

12 Claims, No Drawings

CHLOROBENZENE DERIVATIVES, LIQUID-CRYSTAL COMPOSITION, AND LIQUID-CRYSTAL DISPLAY ELEMENTS

This application is a 371 application of International Application No. PCT/JP97/04329 filed Nov. 27, 1997.

TECHNICAL FIELD

The present invention relates to liquid crystalline compounds and liquid crystal compositions. More specifically, the invention relates to liquid crystalline compounds having chlorine substituted 1,4-phenylene group, liquid crystal compositions comprising the compound, and liquid crystal display devices fabricated by using the liquid crystal composition.

BACKGROUND ART

Display devices produced by using liquid crystalline compounds (the term "liquid crystalline compounds" is used in this specification as a general term for the compounds which exhibit a liquid crystal phase and for the compounds which do not exhibit a liquid crystal phase but are useful as component of liquid crystal compositions) have widely been utilized for the display of watches, tabletop calculators, word processors, or the likes. In recent years, researches on in-plane switching (IPS) mode and vertical alignment (VA) mode by which viewing angle can be improved at a moderate cost have extensively been conducted.

For the liquid crystal compositions used in these modes, such physical properties as a high voltage holding ratio, low threshold voltage, small their dependency on temperature, low optical anisotropy value ($\Delta n$), wide temperature range of liquid crystal phase, excellent miscibility with other liquid crystal materials, and low viscosity have been sought.

As the component of liquid crystal compositions having such characteristics, many liquid crystalline compounds in which fluorine atom substituted at a lateral position were investigated, and patents disclosing, for example, the following compounds are published:

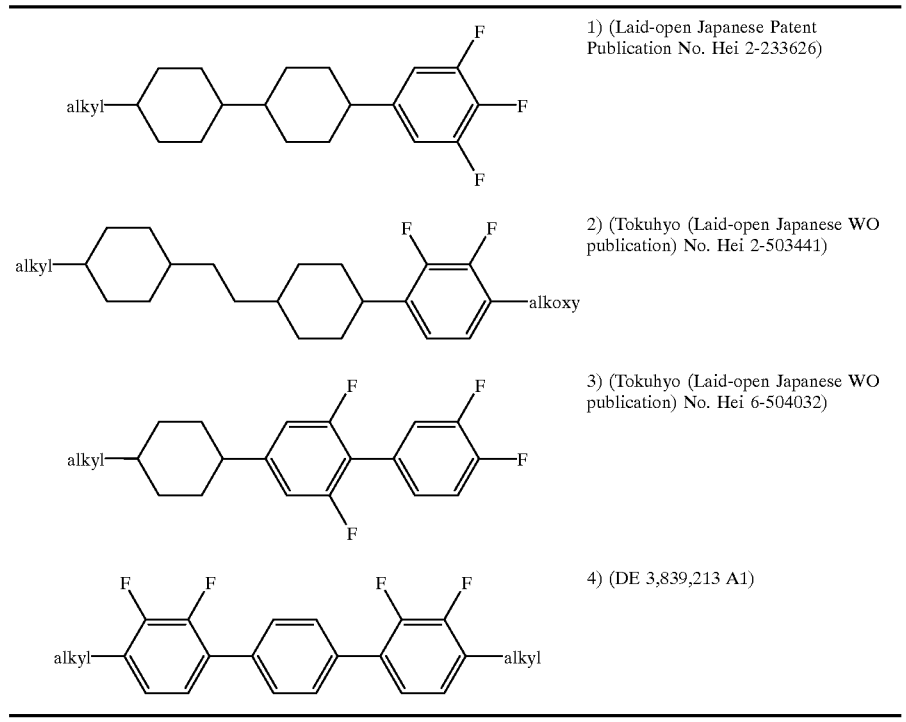

1) (Laid-open Japanese Patent Publication No. Hei 2-233626)

2) (Tokuhyo (Laid-open Japanese WO publication) No. Hei 2-503441)

3) (Tokuhyo (Laid-open Japanese WO publication) No. Hei 6-504032)

4) (DE 3,839,213 A1)

Whereas the compounds of the formula 1) or 2) have a low $\Delta n$, their threshold voltage is high. Whereas the compounds of the formula 3) or 4) have a low threshold voltage, their $\Delta n$ is high. Thus, these compounds can not be said to have satisfied the requirements mentioned above.

Chlorine substituted compounds are disclosed, for example in 5) DE 2,933,563 and 6) DE 4,219,819.

A part of the compounds expressed by the general formula (1) are formally included in the prior literature 5) or 6) mentioned above. However, as to the compounds of the present invention, data such as physical properties are not described at all and their characteristics are not specifically mentioned in the prior publications. Thus, the publications have not suggested the utility of the compounds of the present invention.

DISCLOSURE OF THE INVENTION

In view of the required characteristics described above, an object of the present invention is to provide liquid crystalline compounds having an extremely high voltage holding ratio and a low threshold voltage, being considerably small in their dependency on temperature, having a low $\Delta n$, and being excellent in miscibility with other liquid crystal materials besides; to provide liquid crystal compositions comprising the compound, and to provide liquid crystal display devices fabricated by using the liquid crystal composition.

As a result of diligent investigations by the present invention to solve the problems described above, it has been found out that the chlorobenzene derivatives expressed by the following general formula (1) have desired properties, leading to the accomplishment of the present invention:

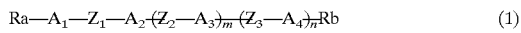

$$Ra—A_1—Z_1—A_2(—Z_2—A_3)_m(—Z_3—A_4)_n Rb \quad (1)$$

wherein Ra represents a straight chain or branched alkyl group having 1 to 20 carbon atoms in which group, any methylene group (—CH$_2$—) may be replaced by —O—, —CO—, —CH=CH—, —C≡C—, —SiH$_2$—, or cyclobutane-1,3-diyl, but in no case continues —O—, and one or more hydrogen atoms in the Ra may be replaced by a halogen atom or cyano group; Rb represents a group selected from the Ra, a halogen atom, or cyano group; $A_1$, $A_2$, $A_3$, and $A_4$ independently represent trans-1,4-cyclohexylene or 1,4-phenylene in which ring any —CH$_2$— may be replaced by —O—, >CH— may be replaced by >SiH—, and —CH= may be represented by —N=, respectively, and one or two hydrogen atoms on the six-membered ring may be replaced by a halogen atom provided that at least two hydrogen atoms among all hydrogen atoms on the six-membered rings which constitute the compound are replaced by a halogen atom including chlorine atom; $Z_1$, $Z_2$, and $Z_3$ independently represent single bond or an alkylene group in which one or more hydrogen atoms may be replaced by a halogen atom, any methylene group (—CH$_2$—) in the alkylene group may be replaced by —O—, —CO—, —CH=CH—, —C≡C—, or —SiH$_2$— but in no case continues —O—; m and n are independently 0 or 1; provided that when m=1, n=0, $A_1$ is trans-1,4-cyclohexylene, $A_2$ and $A_3$ are 1,4-phenylene, and $Z_1$ and $Z_2$ are single bond, or when m+n=1, and at least one of $Z_1$ and $Z_2$ is —COO or —OCO—, then at least three hydrogen atoms in all hydrogen atoms on the six-membered rings which constitute the compound are replaced by a halogen atom including chlorine atom; and provided that when m=1, n=0, $A_1$ and $A_2$ are trans-1,4-cyclohexylene, and $A_3$ is 1,4-phenylene, then in no case are $Z_1$ and $Z_2$ single bond; and an atom which constitutes the compound may be replaced by its isotope.

In the general formula (1), while Ra represents a straight chain or branched alkyl group having 1 to 20 carbon atoms, methyl, ethyl, propyl, butyl, pentyl, hexyl, heptyl, decyl, pentadecyl, and icosyl can specifically be mentioned as straight chain alkyl group; and isopropyl, sec-butyl, tert-butyl, 2-methylbutyl, isopentyl, isohexyl, 3-ethyloctyl, 3,8-dimethyltetradecyl, and 5-ethyl-5-methylnonadecyl can be mentioned as branched alkyl group.

In these alkyl groups, any methylene group (—CH$_2$—) may be replaced by —O—, —CO—, —CH=CH—, —C≡C—, —SiH$_2$—, or cyclobutane-1,3-diyl provided that —O— does not continue.

As examples of these groups, alkoxy group, alkoxyalkyl group, alkenyl group, alkadienyl group, alkenyloxy group, alkoxyalkenyl group, alkynyl group, alkynyloxy group, alkoxyalkynyl group, silanyl group, alkylsilyl group, alkoxysilyl group, alkylsilylalkyl group, alkoxysilylalkyl group, alkyldisilanyl group, alkyldisilanylalkyl group, and alkyltrisilanyl group can be mentioned. Further, one or more hydrogen atoms in these groups may be replaced by a halogen atom, and as its examples, a halogen substituted alkyl group, halogen substituted alkoxy group, halogen substituted alkenyl group, and halogen substituted alkynyl group can be mentioned.

Among them, examples of preferable groups are mentioned as follows:

As groups in which —CH$_2$— is replaced by —O—, alkoxy groups such as methoxy, ethoxy, propoxy, butoxy, pentyloxy, and nonyloxy, and alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl, and octyloxymethyl; and as branched alkoxy groups, 2-methylpropoxy, 2-methylpentoxy, and 1-methylheptoxymethyl can be mentioned.

As groups in which —CH$_2$— is replaced by —CH=CH—, alkenyl groups such as vinyl, propenyl, butenyl, pentenyl, hexenyl, and decenyl, alkoxyalkenyl groups such as methoxypropenyl, ethoxypropenyl, pentyloxypropenyl, methoxybutenyl, ethoxybutenyl, pentyloxybutenyl, methoxypentenyl, propoxypentenyl, methoxyhexenyl, propoxyhexenyl, methoxyheptenyl, and methoxyoctenyl, alkenyloxy groups such as propenyloxy, butenyloxy, pentenyloxy, octenyloxy, and propenyloxymethyl, groups such as propenyloxyethyl, propenyloxybutyl, butenyloxymethyl, butenyloxyethyl, butenyloxypentyl, pentenyloxymethyl, pentenyloxypropyl, hexenyloxymethyl, hexenyloxyethyl, heptenyloxymethyl, and octenyloxymethyl, and alkadienyl groups such as butadienyl, heptadienyl hexadienyl, heptadienyl, octadienyl, and icosadienyl can be mentioned.

As groups in which —CH$_2$— is replaced by —C≡C—, alkynyl groups such as ethynyl, propynyl, butynyl, pentynyl, and octynyl, alkynyloxy groups such as ethynyloxy, propynyloxy, butynyloxy, pentynyloxy, and tetradecynyloxy, and alkoxyalkynyl groups such as methoxypropynyl, methoxypentynyl, ethoxybutynyl, propoxypropynyl, hexyloxyheptynyl, methoxymethylbutynyl, methoxypropylethynyl, and butoxymethylpropynyl can be mentioned.

As groups in which —CH$_2$— is replaced by —SiH$_2$—, alkylsilyl groups such as methylsilyl, ethylsilyl, propylsilyl, butylsilyl, pentylsilyl, and nonylsily, alkylsilylalkyl groups such as methylsilylmethyl, methylsilylethyl, methylsilylpropyl, methylsilylbutyl, methylsilylheptyl, ethylsilylmethyl, ethylsilylethyl, ethylsilylpropyl, ethylsilylhexyl, propylsilylmethyl, propylsilylethyl, propylsilylpropyl, butylsilylmethyl, butylsilylethyl, butylsilylpropyl, pentylsilylmethyl, hexylsilylmethyl, hexylsilylethyl, heptylsilylmethyl, and octylsilylmethyl, alkoxysilyl groups such as methoxysilyl, ethoxysilyl, propoxysilyl, butoxysilyl, pentyloxysilyl, and octyloxysilyl, silanyl groups such as silanyl, disilanyl, trisilanyl, tetrasilanyl, pentasilanyl, and decasilanyl, alkyldisilanyl groups such as methyldisilanyl, ethyldisilanyl, propyldisilanyl, butyldisilanyl, and pentyldisilanyl, alkyltrisilanyl groups such as methyltrisilanyl, ethyltrisilanyl, propyltrisilanyl, and hexyltrisilanyl, alkyldisilanylalkyl groups such as methylnonasilanyl, methyldisilanylmethyl, methyldisilanylethyl, methyldisilanylpentyl, ethyldisilanylmethyl, ethyldisilanylethyl, ethyldisilanylbutyl, ethyldisilanylhexyl, propyldisilanylmethyl, butyldisilanylpentyl, pentyldisilanylmethyl, hexyldisilanylethyl, and heptyldisilanylmethyl, alkyltrisilanylalkyl groups such as methyltrisilanylmethyl, methyltrisilanylpentyl, ethyltrisilanylmethyl, ethyltrisilanylpropyl, propyltrisilanylmethyl, propyltrisilanylbutyl, butyltrisilanylmethyl, pentyltrisilanylmethyl, and hexyltrisilanylmethyl, and groups such as methylhexasilanylmethyl, ethylheptasilanylmethyl, methyloctasilanylmethyl, 2-fluoroethylsilyl, 3,3-difluoropropylsilyl, and 1,2,3,3-tetrafluoropropylsilyl can be mentioned.

As groups in which —CH$_2$— is replaced by —CO—, groups such as methylcarbonyl, ethylcarbonyl, propylcarbonyl, methoxycarbonyl, ethoxycarbonyl, propoxycarbonyl, butoxycarbonyl, heptyloxycarbonyl, 2-oxopropyl, 2-oxobutyl, 3-oxobutyl, 2-oxopentyl, 4-oxopentyl, 3-oxohexyl, 5-oxohexyl, 2-oxoheptyl, 3-oxoheptyl, 6-oxoheptyl, 2-oxooctyl, 4-oxooctyl, 7-oxooctyl, 3-oxononyl, 6-oxononyl, 8-oxononyl, 2-oxodecyl, 5-oxodecyl, and 9-oxodecyl can be mentioned.

Hydrogen atom in these groups may be replaced by a halogen atom or cyano group, and specifically halogen substituted alkyl groups such as fluoromethyl, difluoromethyl, trifluoromethyl, 2-fluoroethyl, 1,2-difluoroethyl, 2-bromo-1,2-difluoroethyl, 3-fluoropropyl, 1,2,3,3-tetrafluoropropyl, 4-fluorobutyl, 1,1,2,4-tetrafluorobutyl, 5-fluoropentyl, 1,1,3,3,3-pentafluoropropyl, 2,3,3,4,5-pentafluoropentyl, 6-fluorohexyl, 2,3,4,6-tetrafluorohexyl, 7-fluoroheptyl, and 8,8-difluorooctyl, halogen substituted alkoxy groups such as difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 1,1,3,3,3-pentafluoropropoxy, 1,1,2,3,3,3-hexafluoropropoxy, and perfluoropropoxy, and halogen substituted alkenyl groups such as 3-fluoropropenyl, 4-fluoro-1-butenyl, 4-fluoro-2-butenyl, 5-fluoro-1-pentenyl, 5-fluoro-2-pentenyl, 5-fluoro-3-pentenyl, 6-fluoro-1-hexenyl, 6-fluoro-3-hexenyl, 7-fluoro-5-heptenyl, 2,2-difluorovinyl, 1,2-difluorovinyl, 2-chloro-2-fluorovinyl, 2-bromo-2-fluorovinyl, 2-fluoro-2-cyanovinyl, 3,3-difluoro-2-propenyl, 3-chloro-3-fluoro-1-propenyl, 2,3-difluoro-1-propenyl, 1,3-difluoro-2-propenyl, 1,3,3-trifluoro-2-propenyl, 1,2,4,4-tetrafluoro-3-butenyl, 5,5-difluoro-4-pentenyl, 3,3-difluorohexenyl, and 8,8-difluoro-7-octenyl can be mentioned.

Among them, alkyl groups, alkoxy groups, alkoxyalkyl groups, alkenyl groups, alkoxyalkenyl groups, alkylsilyl groups, halogen substituted alkyl groups, halogen substituted alkoxy groups, and halogen substituted alkenyl groups are more preferable.

Next, Rb is selected from the group which is further selected from Ra; cyano group; or a group of halogen atoms including F, Cl, Br, and I. However, groups or atoms except Br and I are preferable from the aspect of stability.

$A_1$, $A_2$, $A_3$, and $A_4$ independently from one another represent trans-1,4-cyclohexylene, or 1,4-phenylene in which one or two hydrogen atoms may be replaced by a halogen atom. In the six-membered ring, —CH$_2$— may be replaced by —O—, >CH— may be replaced by >SiH—, and —CH= may be replaced by —N=, respectively. Specifically, piperidinediyl, piperazinediyl, pyridinediyl, pyrazinediyl, pyrimidinediyl, pyridazinediyl, triazinediyl, tetrazinediyl, tetrahydropyrandiyl, dioxanediyl, and silacyclohexanediyl can be mentioned.

Among them, as preferable groups, trans-1,4-cyclohexylene, 1,4-phenylene, and 1,4-phenylene in which one or two hydrogen atoms are replaced by a halogen atom, that is, 2-fluoro-1,4-phenylene, 3-fluoro-1,4-phenylene, 2,3-difluoro-1,4-phenylene, 3,5-difluoro-1,4-phenylene, 2-chloro-1,4-phenylene, 3-chloro-1,4-phenylene, 2,3-dichloro-1,4-phenylene, 3,5-dichloro-1,4-phenylene, 2-chloro-3-fluoro-1,4-phenylene, 3-chloro-2-fluoro-1,4-phenylene, and 3-fluoro-5-chloro-phenylene can be mentioned. In divalent groups of six-membered ring having a hetero atom, pyridine-2,5-diyl, pyrimidine-2,5-diyl, tetrahydropyran-2,5-diyl, 1,3-dioxane-2,5-diyl, 1,4-dioxane-2,5-diyl, and 1-sila-1,4-cyclohexanediyl can be mentioned. More preferably, when cis-trans isomers exist in these six-membered rings, steric structure of the rings is trans form.

While $Z_1$, $Z_2$, and $Z_3$ are single bond or an alkylene group having 1 to 4 carbon atoms in which group one or more hydrogen atoms contained therein may be replaced by a halogen atom, single bond, ethylene, or butylene is preferable. Also, the methylene group (—CH$_2$—) which constitutes the alkylene group may be replaced by —SiH$_2$—, —O—, —CH=CH—, or —C≡C—, but in no case continues —O—. As such groups, ones having —SiH$_2$—, such as 1,2-disilanediyl, 1,4-tetrasilanediyl, 1-silaethylene, 2-silaethylene, 1-sila-1,4-butylene, 2-sila-1,4-butylene, and 3-sila-1,4-butylene, groups having —O—, such as oxymethylene, methylenoxy, 1-oxy-1,4-butylene, 2-oxy-1,4-butylene, 3-oxy-1,4-butylene, 4-oxy-1,4-butylene, and ester bond, groups having —CH=CH—, such as vinylene, 1-butenylene, 2-butenylene, and 3-butenylene, groups having —C≡C—, such as ethynylene, 1-butynylene, 2-butynylene, and 3-butynylene, and each of the groups described above in which one or more hydrogen atoms are butenylene, and 3-butenylene, groups having —C≡C—, such as ethynylene, 1-butynylene, 2-butynylene, and 3-butynylene, and each of the groups described above in which one or more hydrogen atoms are replaced by a halogen atom, for example, fluoromethylenoxy, oxyfluoromethylene, difluoromethylenoxy, oxydifluoromethylene, 1,1-difluoroethylene, 2,2-difluoroethylene, 1,2-diflurovinylene, 1-fluorovinylene, 1-bromo-2-flurovinylene, 1-chloro-2-fluorovinylene, 1,2-difluoro-1-butenylene, 2,3-difluoro-2-butenylene, 3,4-difluoro-3-butenylene, as well as 3-oxy-1-butenylene and 4-oxy-1-butenylene can be mentioned.

While all compounds of the present invention which are composed of groups selected from each of the Ra, Rb, $A_1$ to $A_4$, if and $Z_1$ to $Z_3$ described above and used in combination are preferable ones having characteristics inherent to the compounds of the present invention, more preferably the compounds of the present invention do not include two or more rings having a hetero atom.

Among such compounds, a group of compounds having especially preferable characteristics are those shown by one of the following formulas (1-1) to (1-131):

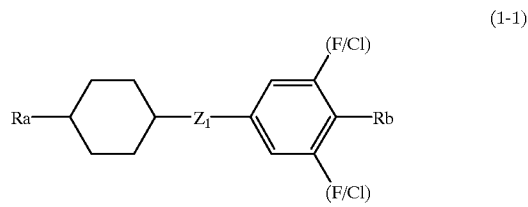

(1-1)

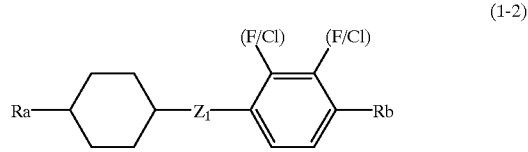

(1-2)

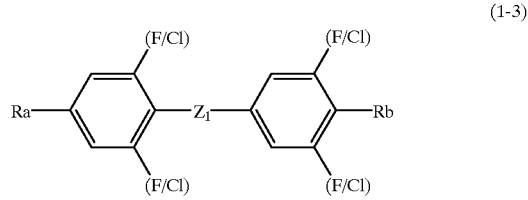

(1-3)

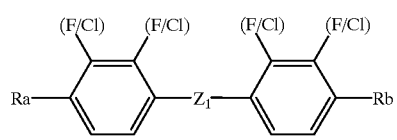
(1-4)
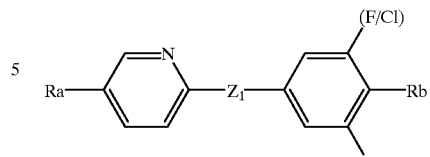
(1-13)
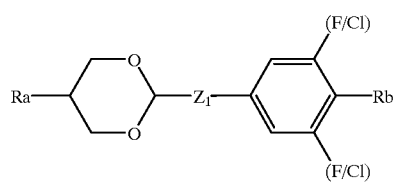
(1-5)
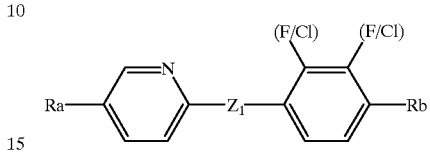
(1-14)
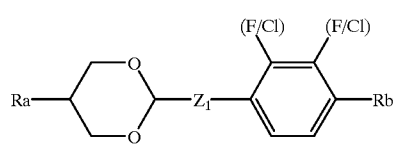
(1-6)
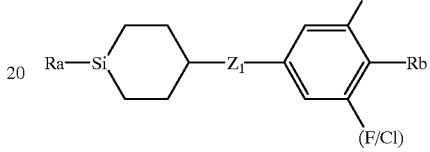
(1-15)
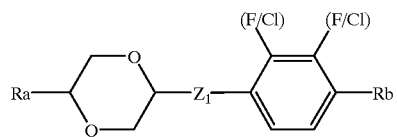
(1-7)
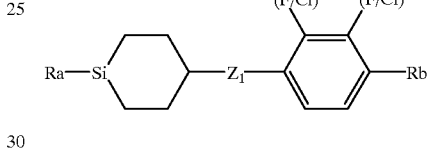
(1-16)
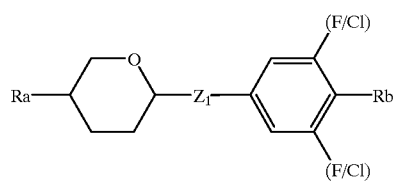
(1-8)
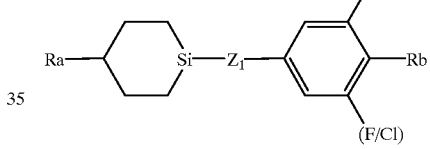
(1-17)
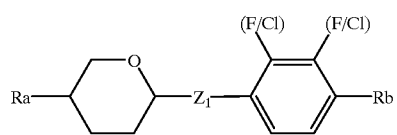
(1-9)
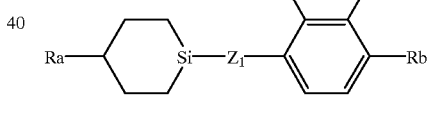
(1-18)
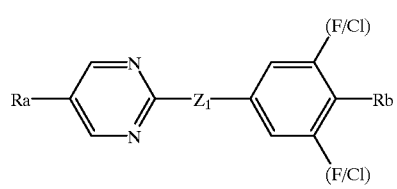
(1-10)
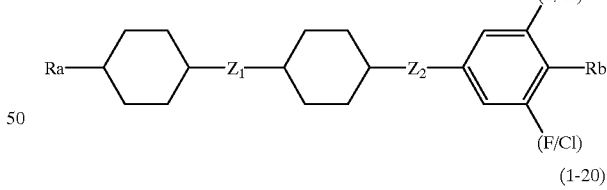
(1-19)
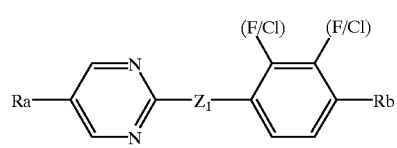
(1-11)
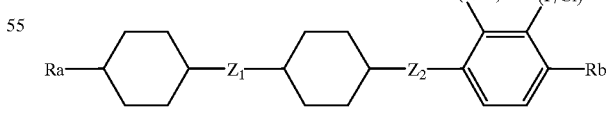
(1-20)
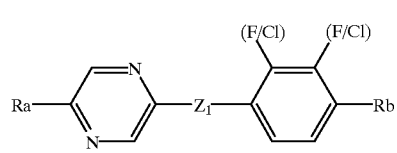
(1-12)
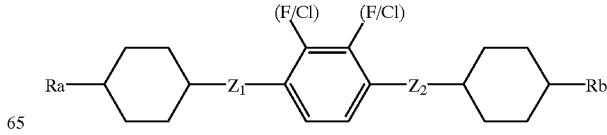
(1-21)

(1-22)
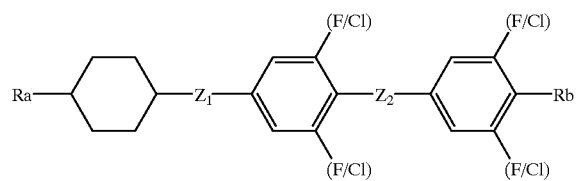
(1-23)
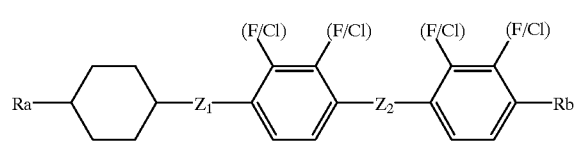
(1-24)
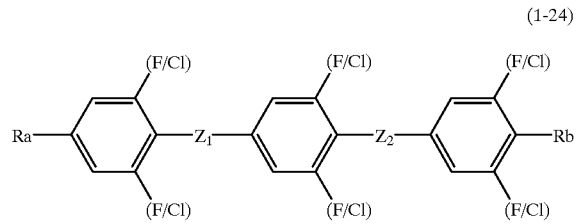
(1-25)
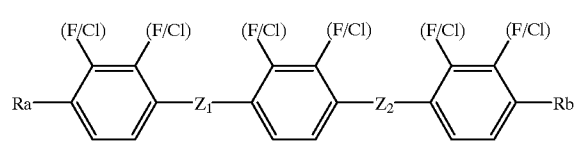
(1-26)
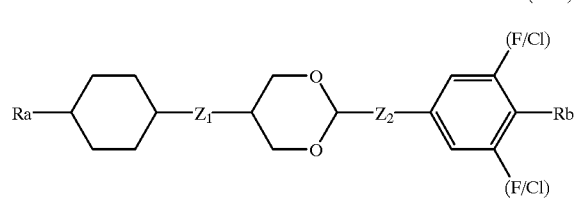
(1-27)
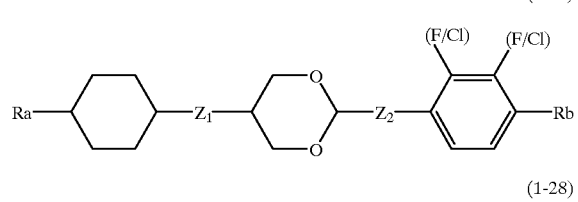
(1-28)
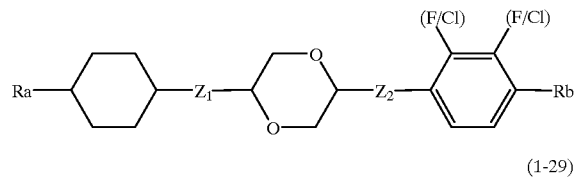
(1-29)
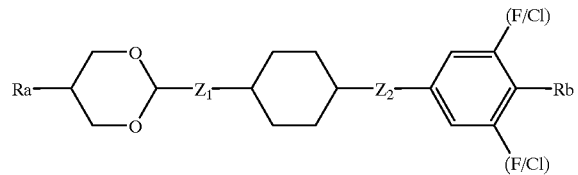
(1-30)
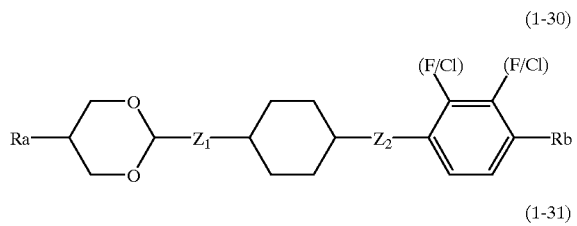
(1-31)
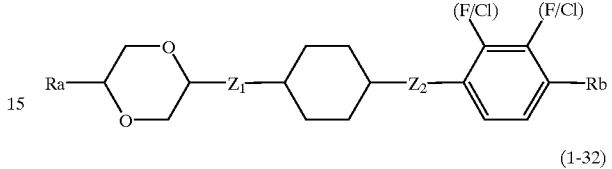
(1-32)
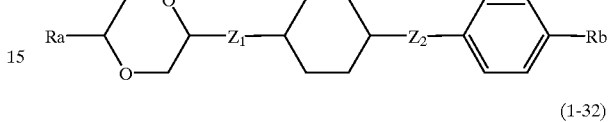
(1-33)
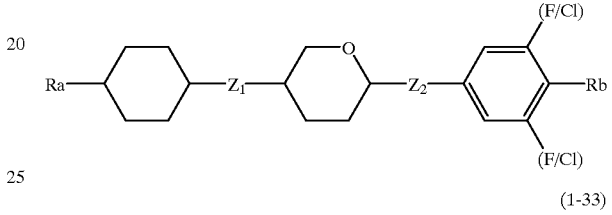
(1-34)
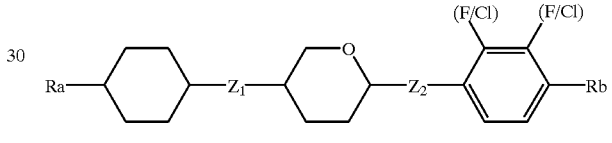
(1-35)
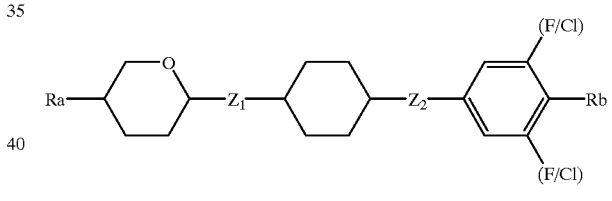
(1-36)
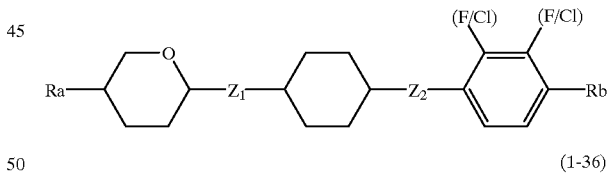
(1-37)
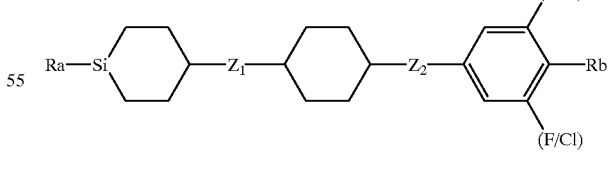

(1-38)
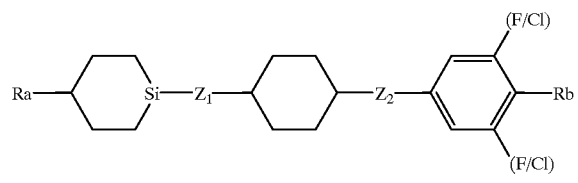
(1-39)
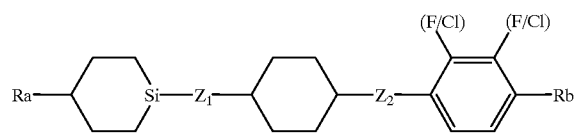
(1-40)
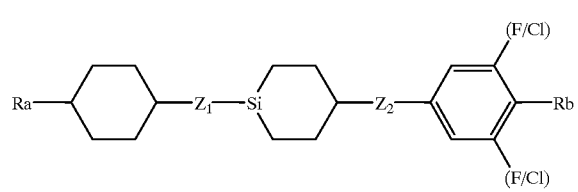
(1-41)
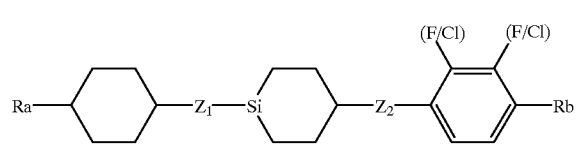
(1-42)
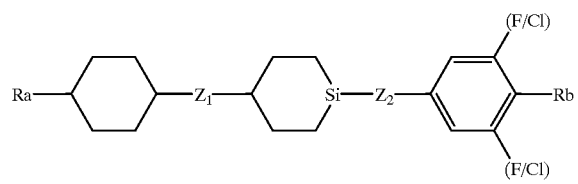
(1-43)
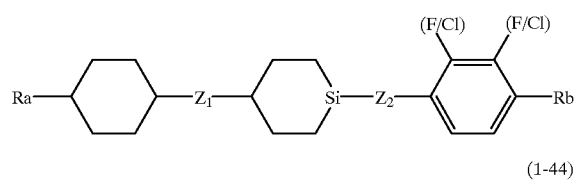
(1-44)
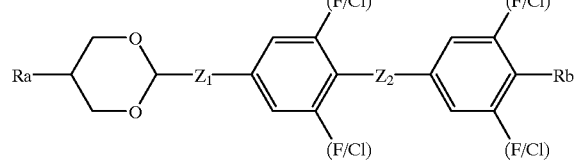
(1-45)
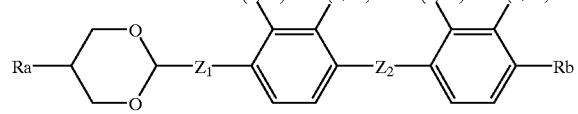
(1-46)
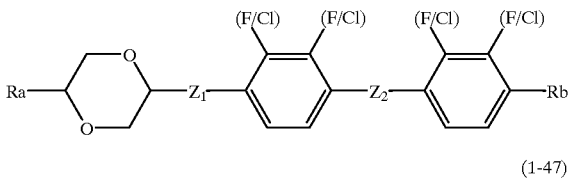
(1-47)
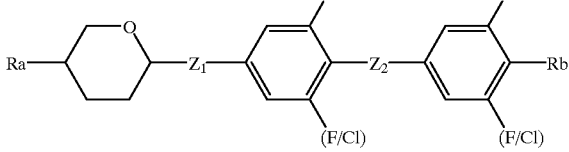
(1-48)
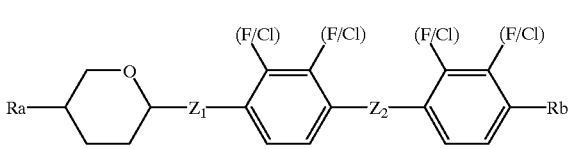
(1-49)
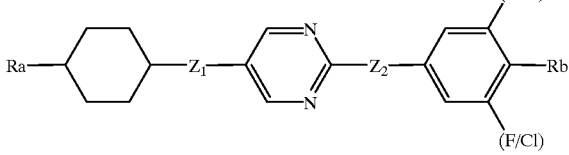
(1-50)
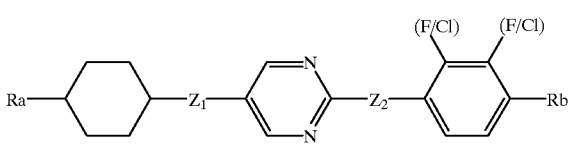
(1-51)
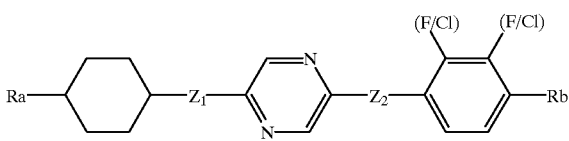
(1-52)
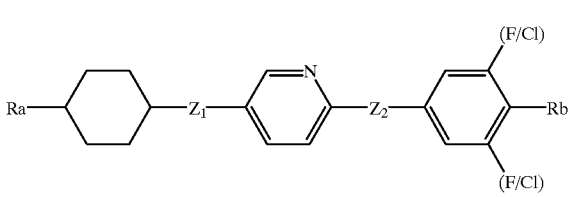
(1-53)
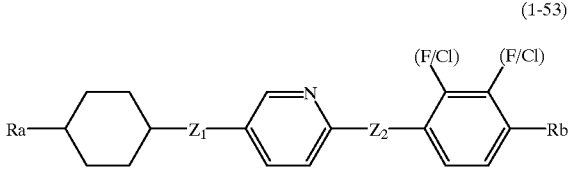

(1-54)
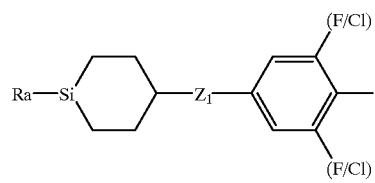
(1-55)
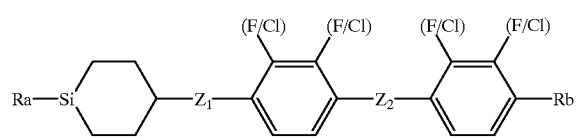
(1-56)
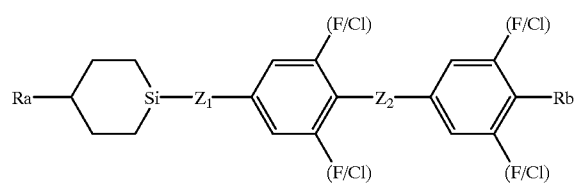
(1-57)
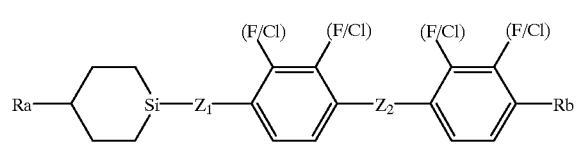
(1-58)
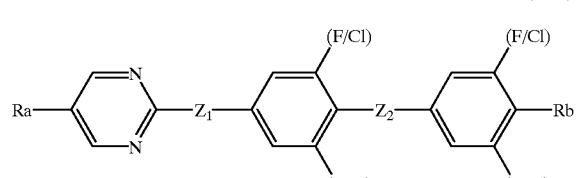
(1-59)
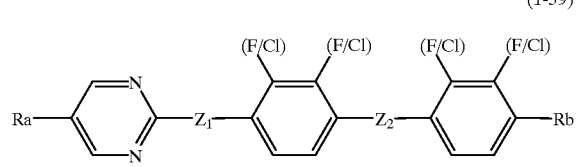
(1-60)
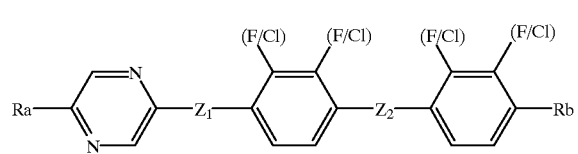
(1-61)
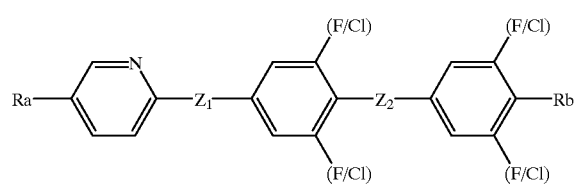
(1-62)
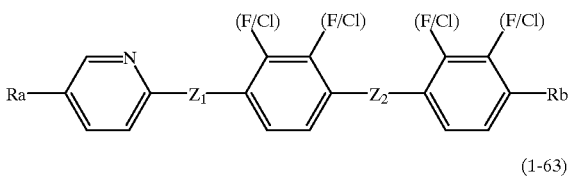
(1-63)
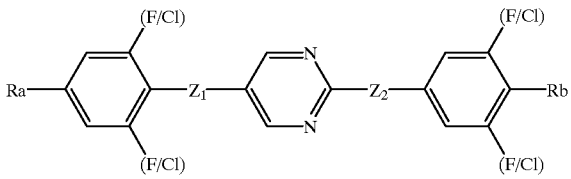
(1-64)
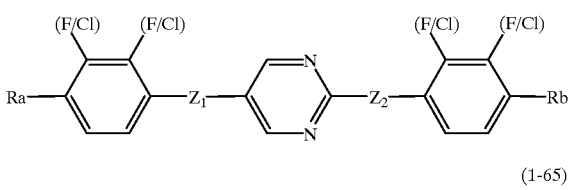
(1-65)
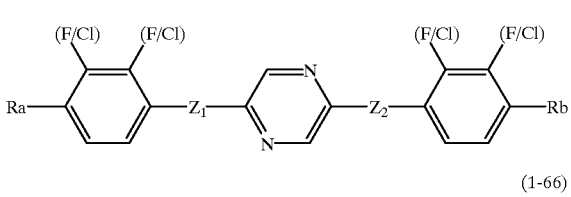
(1-66)
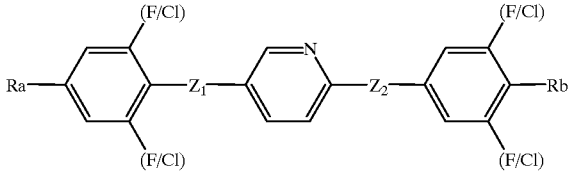
(1-67)
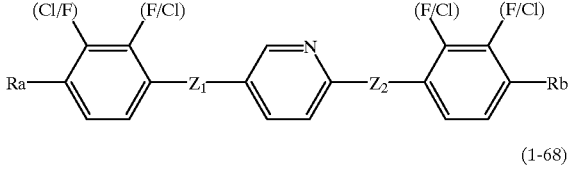
(1-68)
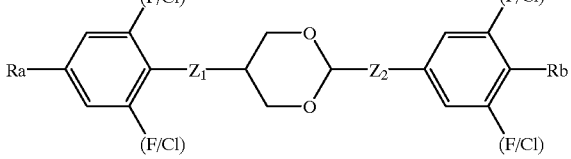
(1-69)
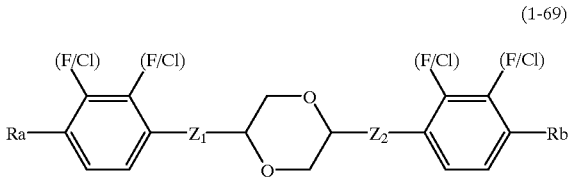

-continued
(1-70)
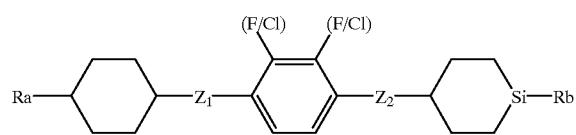
(1-71)
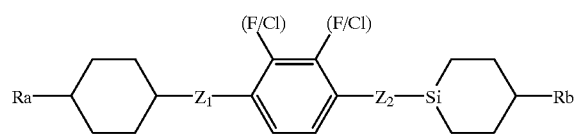
(1-72)
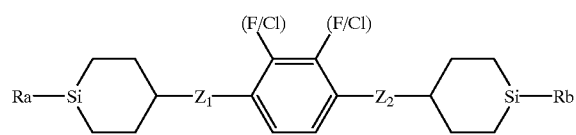
(1-73)
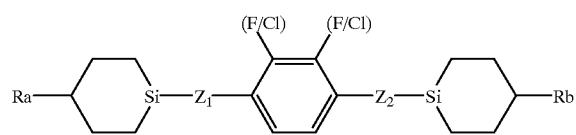
(1-74)
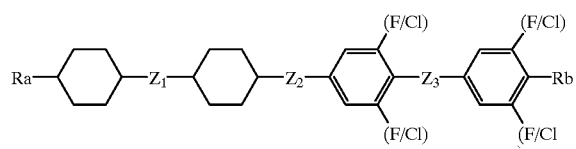
(1-75)
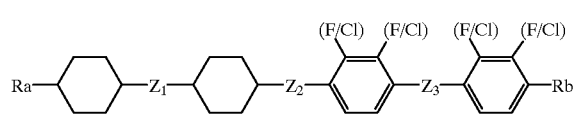
(1-76)
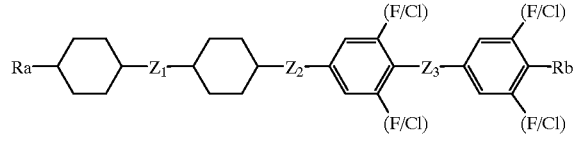
(1-77)
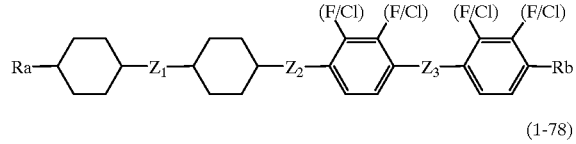
(1-78)
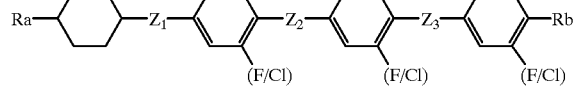
-continued
(1-79)
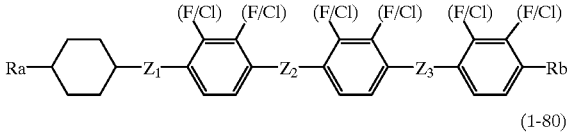
(1-80)
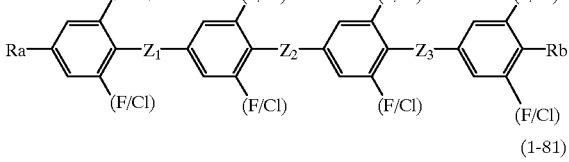
(1-81)
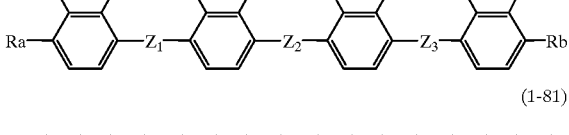
(1-81)
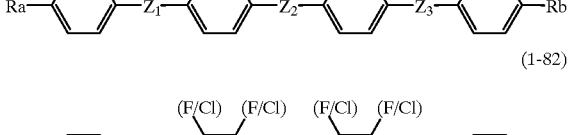
(1-82)
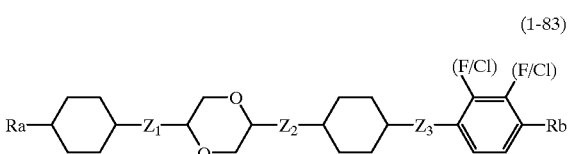
(1-83)
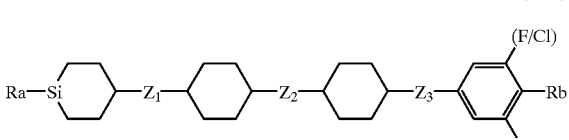
(1-84)
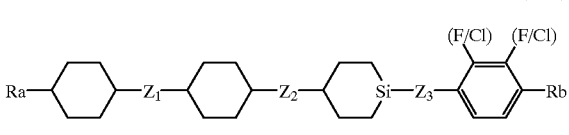
(1-85)
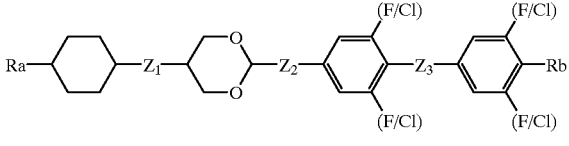
(1-86)
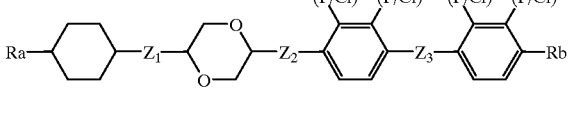
(1-87)

(1-88)
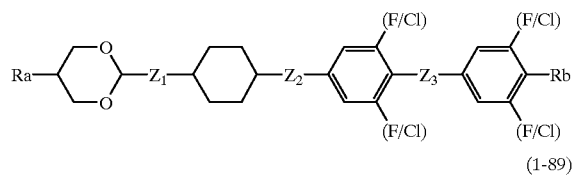
(1-89)
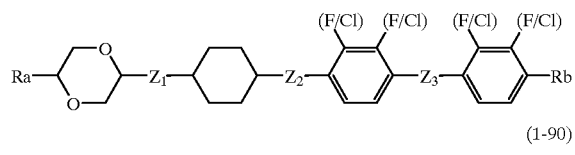
(1-90)
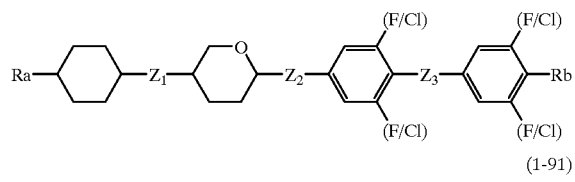
(1-91)
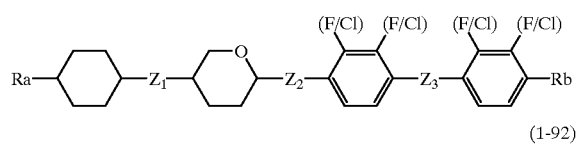
(1-92)
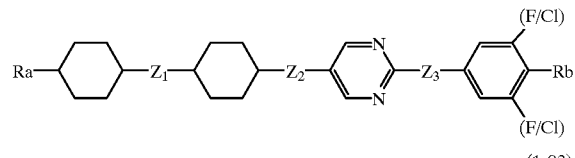
(1-93)
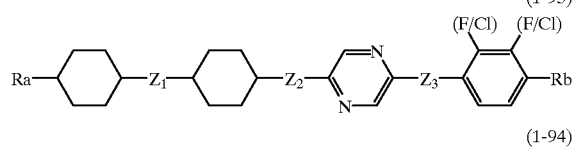
(1-94)
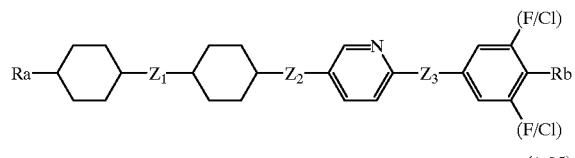
(1-95)
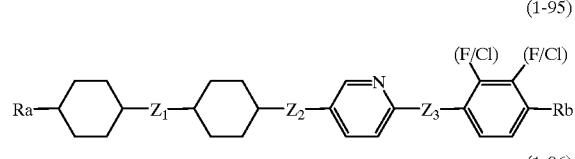
(1-96)
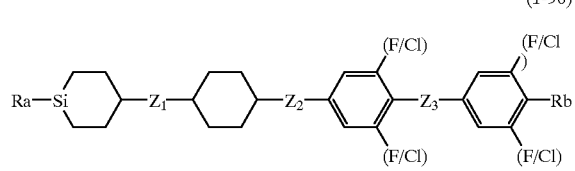
(1-97)
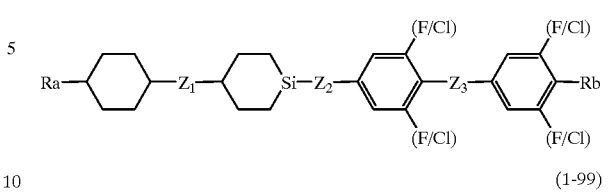
(1-98)
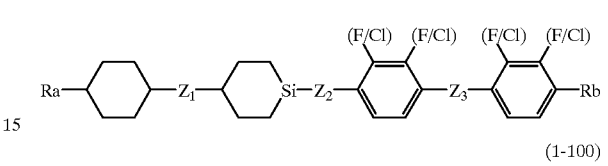
(1-99)
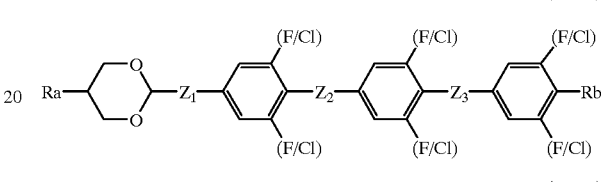
(1-100)
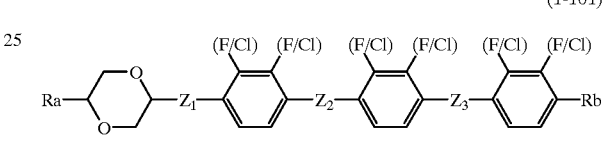
(1-101)
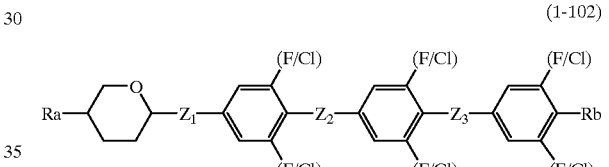
(1-102)
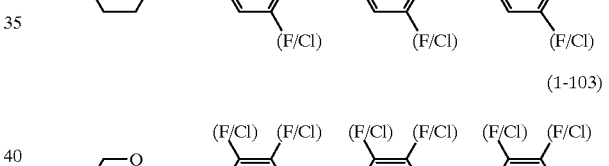
(1-103)
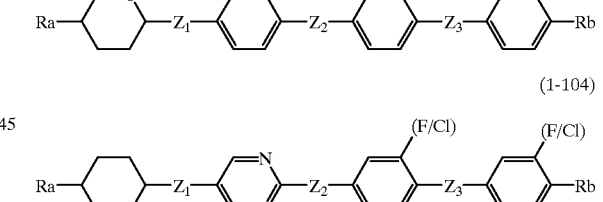
(1-104)
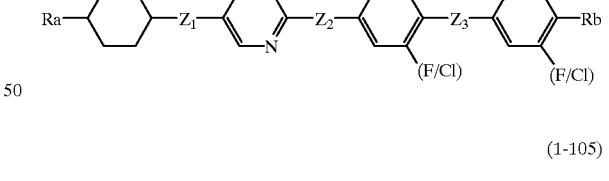
(1-105)
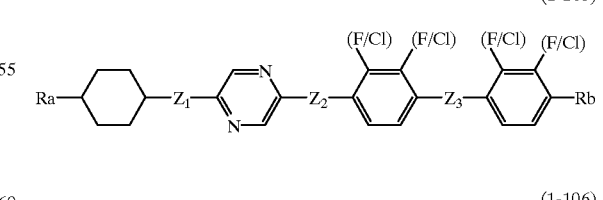
(1-106)
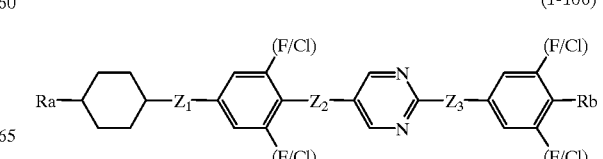

-continued
(1-107)
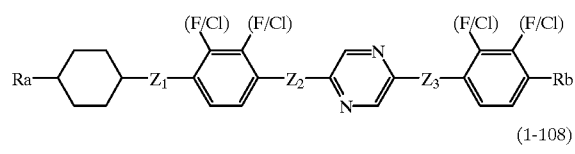
(1-108)
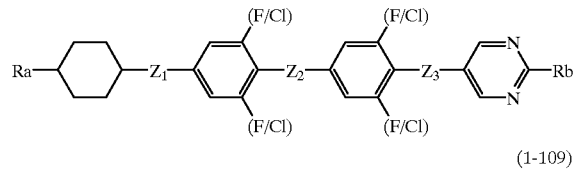
(1-109)
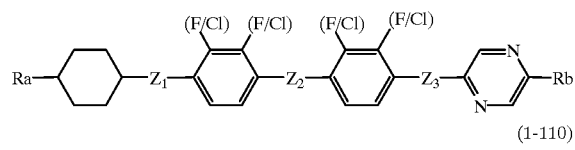
(1-110)
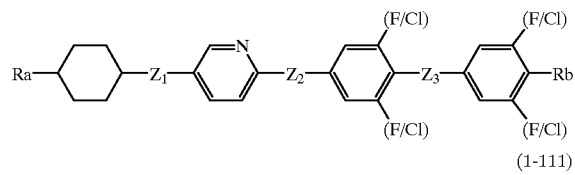
(1-111)
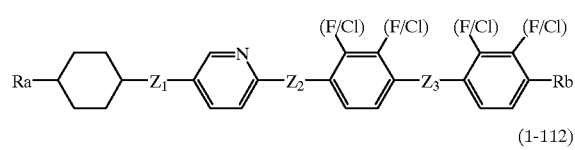
(1-112)
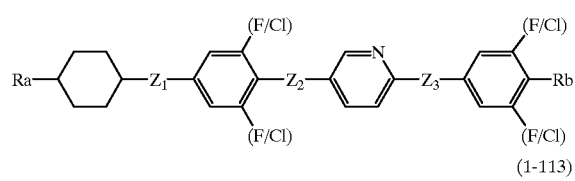
(1-113)
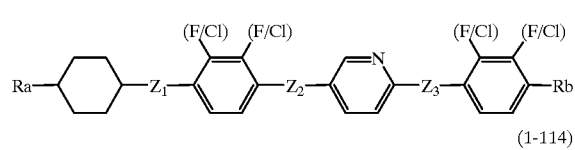
(1-114)
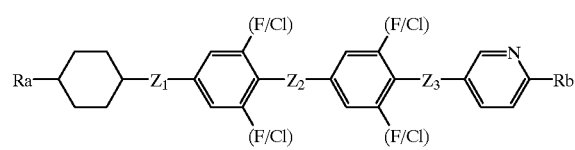
(1-115)
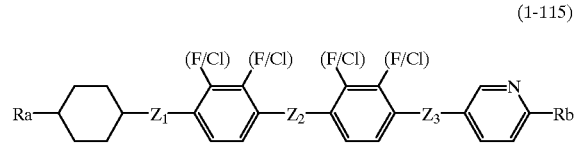
(1-116)
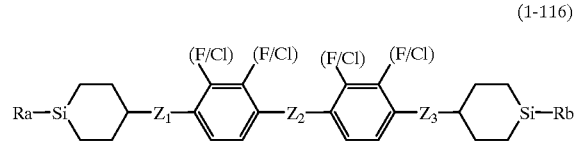
(1-117)
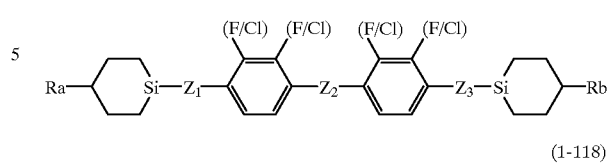
(1-118)
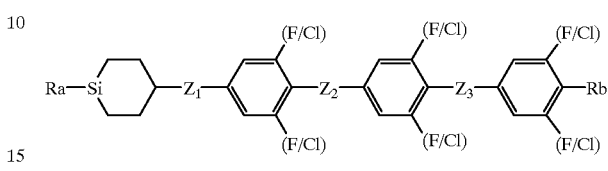
(1-119)
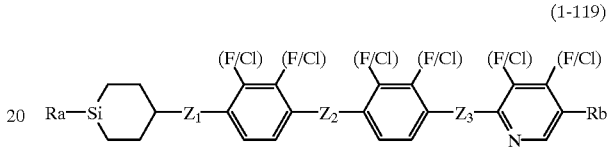
(1-120)
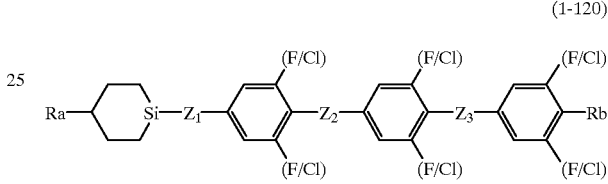
(1-121)
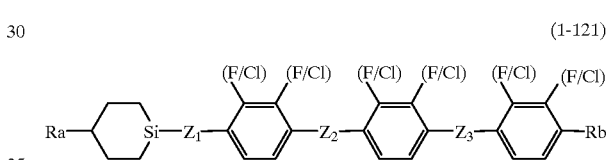
(1-122)
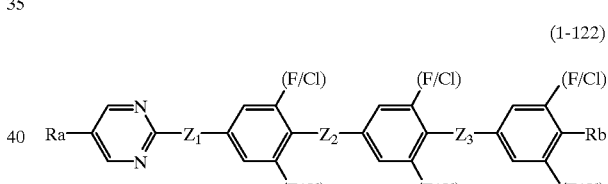
(1-123)
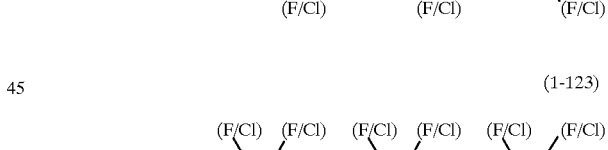
(1-124)
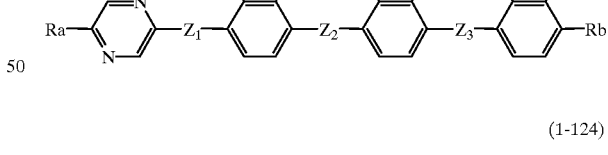
(1-125)
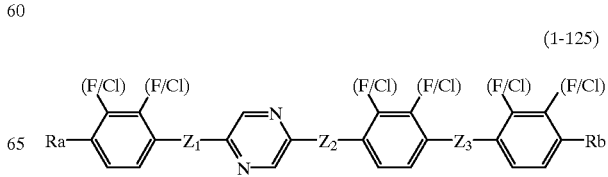

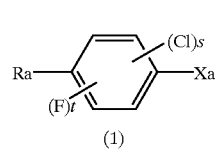
(1-126)

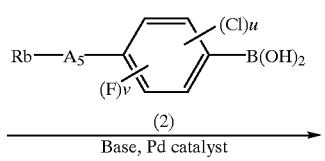
(1-127)

(1-128)

(1-129)

(1-130)

(1-131)

wherein Ra, Rb, and $Z_1$ to $Z_3$ have the same meaning and the hydrogen atom on 1,4-phenylene group may independently be replaced by the atom shown in the parentheses within the scope of the present invention.

While the liquid crystalline compounds of the present invention expressed by the general formula (1) can be produced by ordinary methods of organic synthesis, they can conveniently be produced, for instance, by the following methods:

(scheme1)

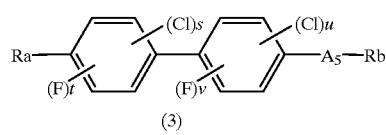
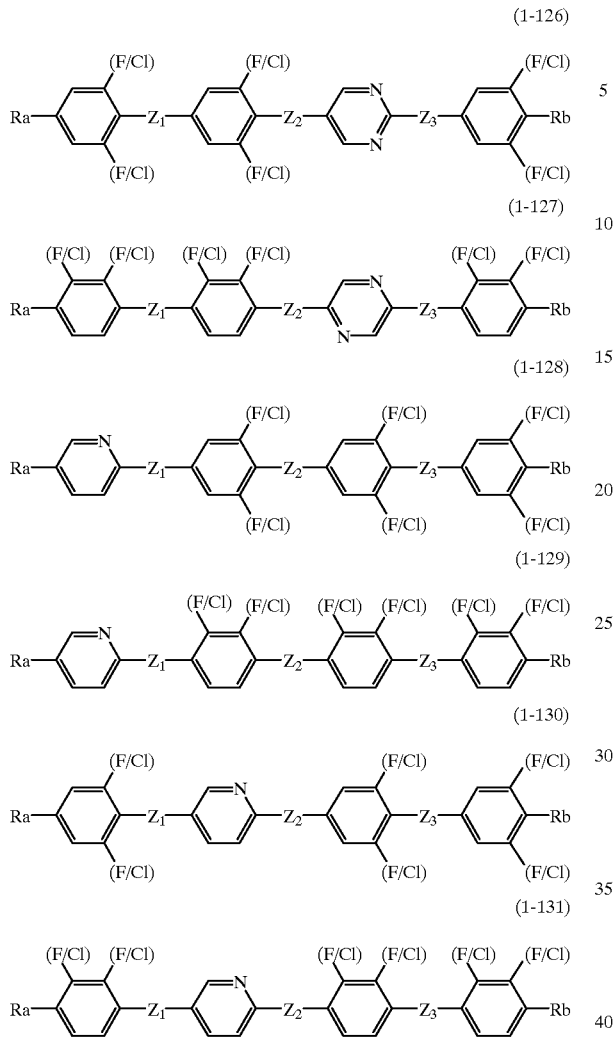

(scheme2)

(scheme3)

(scheme4)

(scheme5)

(scheme6)

Ra—A₁—C≡C—H    (17)
Rb—A₅—A₂—Xa   (18)
→ (Pd catalyst, CuI) →
Ra—A₁—C≡C—A₂—A₅—Rb   (19)

(scheme7)

Ra—A₁—COOH (20) →(SOCl₂)→ Ra—A₁—COCl (21) →(12),Py→ Ra—A₁—COO—A₂—A₅—Rb (22)

(scheme8)

Ra—A₁—Xa (23) →[1) n-BuLi, Xb(CH₂)rXc (24); 2) Li/ultrasound, SiCl₄]→
Ra—A₁—(CH₂)rSiCl₃ (25) →[Rb—A₅—A₂—Li (26)]→
Ra—A₁—(CH₂)rSiCl₂—A₂—A₅—Rb (27) →SBH→
Ra—A₁—(CH₂)rSiH₂—A₂—A₅—Rb (28)

(scheme9)

(23) →(Mg, CS₂, H₂O, HCl)→ Ra—A₁—CSSH (29) →[DCC; Rb—A₅—A₂—ONa (30)]→
Ra—A₁—C(=S)O—A₂—A₅—Rb (31) →DAST→
Ra—A₁—CF₂O—A₂—A₅—Rb (32)

(scheme10)

Ra—CH₂—COOC₂H₅ (33) →(LDA, XaCOOC₂H₅ (34))→

Ra—CH(COOC₂H₅)₂ (35) →LAH→ Ra—CH(CH₂OH)₂ (36) →(15), H⁺→

[1,3-dioxane: Ra at 5-position, A₂—A₅—Rb at 2-position] (37)

(scheme11)

Ra—A₁—(CH₂)q—CH=CH₂ (38) →mCPBA→

Ra—A₁—(CH₂)q—[epoxide] (39) →CF₃COOH→

Ra—A₁—(CH₂)q—CH(OH)—CH₂OH (40) →TBDMS-Cl→

Ra—A₁—(CH₂)q—CH(OH)—CH₂OTBDMS (41) →(CF₃SO₂)₂O→

Ra—A₁—(CH₂)q—CH(O₂SCF₃)—CH₂OTBDMS (42)

HO—CH₂—CH(A₅—Rb)—O—C(=O)—(2,4,6-trimethylphenyl) (43)
→

Ra—A₁—(CH₂)q—CH(—CH₂OTBDMS)—O—CH₂—CH(A₅—Rb)—O—C(=O)—(2,4,6-trimethylphenyl) (44) →NaOH→

Ra—A₁—(CH₂)q—CH(—CH₂OH)—O—CH₂—CH(OH)—A₅—Rb (45) →H⁺→

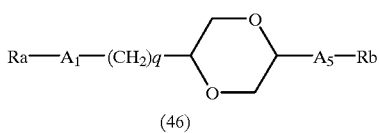

(46)

(scheme12)

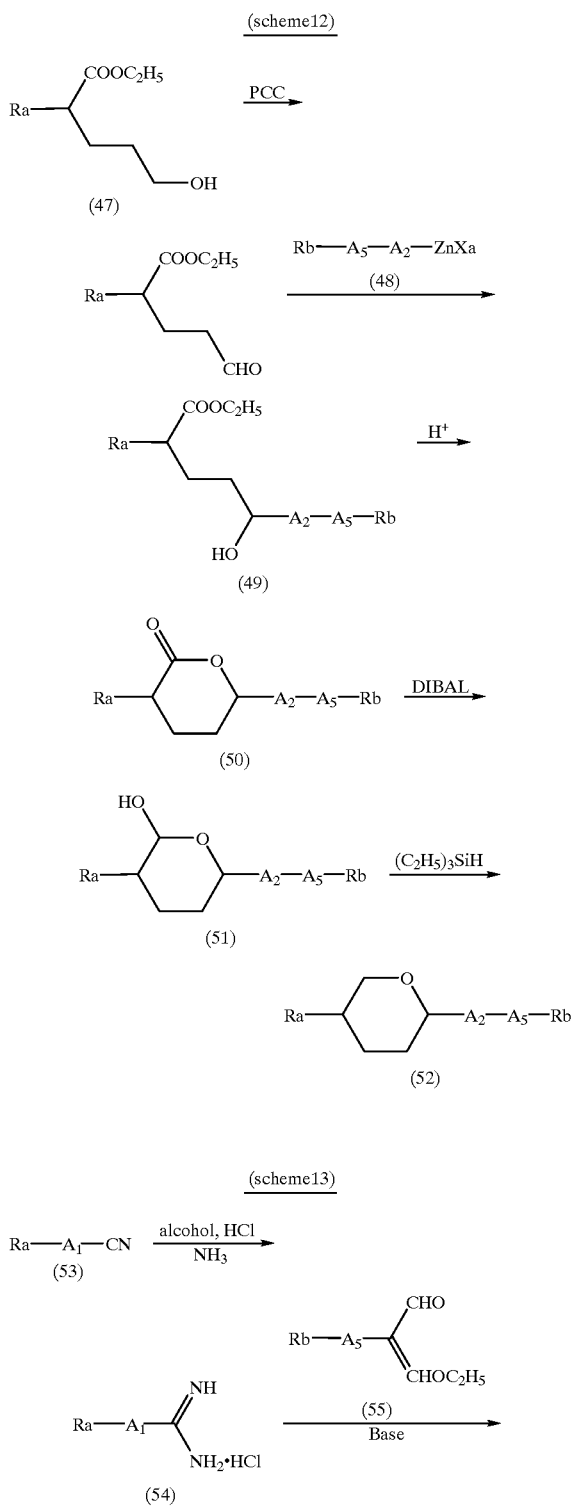

(scheme13)

Ra—A₁—CN (53)  →(alcohol, HCl / NH₃)

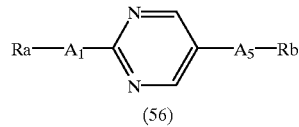

(56)

(scheme14)

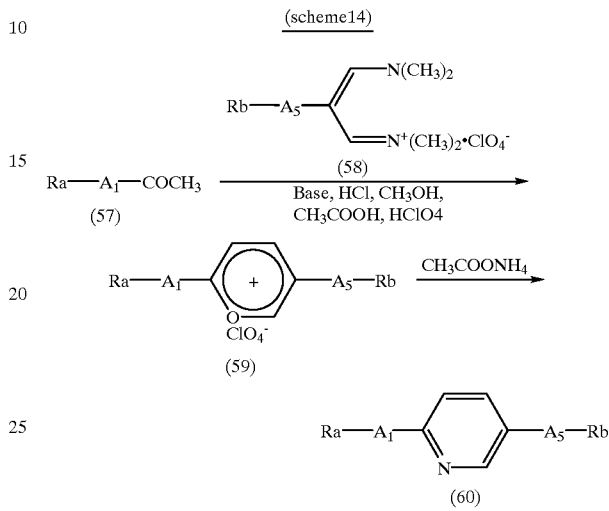

wherein Ra, Rb, A₁. and A₂ have the same meaning as described above, Xa and Xb represent a halogen atom (particularly bromine and iodine are preferable), q is an integer of 0 to 4, r is an integer of 1 to 3, (Cl)s, (Cl)u, (F)t, and (F)v indicate that hydrogen atom on the ring may be replaced by fluorine atom or chlorine atom, respectively, s, t, u, and v are independently 0, 1, or 2 provided that s+t=u+v≦2, and A₅ represents the following group:

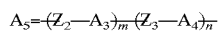

That is, as shown in scheme 1, compound (3) which is an example of the compounds of the present invention can be produced by reaction compound (1) with dihydroxyborane derivative (2) in a mixed solvent of toluene, xylene or the like, an alcohol such as ethanol, and water in the presence of a base such as K₂CO₃ and Na₂CO₃, and a catalyst such as palladium carried on carbon (Pd-C), Pd(PPh₃)₄, and PdCl₂(PPh₃)₂ (M. Hird et al., Liq. Cryst., 18 (1), 1 (1995)).

As shown in scheme 2, compound (7) of the present invention can be produced by converting compound (1) into compound (5) by the method of Imamoto et al. (J. Am. Chem. Soc., 111, 4392 (1989)), subjecting to a dehydration reaction in the presence of an acidic catalyst such as p-toluenesulfonic acid (PTS), and then subjecting to a reduction with hydrogen in the presence of a catalyst such as Pd-C and Raney nickel.

As shown in scheme 3, compound (10) of the present invention can be produced by reacting compound (8) with lithium and a zinc compound, and then reacting with compound (9) in the presence of a palladium catalyst (Hayashi et al., J. Am. Chem. Soc., 106, 158 (1984)).

As shown in scheme 4, compound (13) of the present invention can be produced by reacting compound (11) with compound (12) in a solvent such as dimethyl sulfoxide, dimethyl formamide, 1,2-dimethoxyethane, tetrahydrofuran, hexamethylphosphoric triamide, and toluene in the presence of a base such as sodium amide (J. B. Wright et al., J. Am. Chem. Soc., 70, 3098 (1948)), potassium carbonate (W. T.

Olson et al., J. Am. Chem. Soc., 69, 2451 (1947)), triethylamine (R. L. Merker et al., J. Org. Chem., 26, 5180 (1961)), sodium hydroxide (C. Wilkins, Synthesis, 156 (1973)), potassium hydroxide (J. Rebek et al., J. Org. Chem., 44, 1485 (1979)), barium hydroxide (Kawabe et al., J. Org. Chem., 37, 4210 (1972)), and sodium hydride (NaH) (C. J. Stark, Tetrahedron Lett., 22, 2089 (1981) and K. Takai et al., Tetrahedron Lett., 21, 1657 (1980)).

As shown in scheme 5, compound (16) which is an example of the compounds of the present invention can be produced by subjecting compound (14) and compound (15) to the Wittig reaction in the presence of a base such as potassium-tert-butoxide, sodium methoxide, and n-butyl lithium (A. Maercker, Org. React., 14, 270). Further, an isomerizing reaction can subsequently be conducted with benzenesulfinic acid or p-toluenesulfinic acid.

As shown in scheme 6, compound (19) of the present invention can be produced by subjecting compound (17) and compound (18) to a coupling reaction in the presence of copper iodide and a Pd catalyst such as Pd(PPh$_3$)$_4$, PdCl$_2$(PPh$_3$)$_2$, and Pd(OAc)$_2$.(PPh$_3$)$_2$ (L. Cassar, J. Organomet. Chem., 93, 253 (1975)).

As shown in scheme 7, compound (22) of the present invention can be produced by converting compound (20) into compound (21) with a halogenating agent such as thionyl chloride in a solvent such as toluene and benzene, or in the absence of a solvent, and then reacting the compound (21) with compound (12) (E. J. Corey et al., J. Org. Chem., 38, 3223 (1973)). This reaction is preferably conducted in the presence of a base such as pyridine (Py), triethylamine (B. Iselin et al., Helv. Chim. Acta., 40, 373 (1957)), dimethylaniline (C. Raha, Org. Synth., IV, 263 (1963)), and tetramethylurea (M. S. Newman et al., Tetrahedron Lett., 3267 (1967)) for promoting reaction.

While the methods for producing compounds having silicon atom are described in detail in such books as E. W. Colvin et al. (Silicon in Organic Synthesis, Butteworths, London (1981)), W. P. Weber (silicon Reagents for Organic Synthesis, Springer-Verlag, Berlin (1983), and E. W. Colvin (Silicon Reagents in Organic Synthesis, Academic Press, London (1988), the compounds can be produced, for instance, by the method shown in scheme 8.

That is, as shown in scheme 8, compound (23) is reacted with n-butyl lithium (n-BuLi) and compound (24) to obtain a halide, lithiating the halide with lithium, and then reacting it with tetrachlorosilane to form compound (25). Compound (28) of the present invention can be produced by reacting the compound (25) with compound (26), and then reducing with a reducing agent such as sodiumboro hydride (SBH) and lithium aluminum hydride (LAH).

As shown in scheme 9, compound (23) is converted into compound (29) by the method of J. Houben et al. (Chem. Ber., 40, 1303 (1907), and then converted into compound (31) by the method of Kato et al. (Liebigs Ann. Chem., 7, 1229 (1982)). Subsequently, the compound (31) is fluorinated with a fluorinating agent such as diethylaminosulfur trifluoride (DAST) (W. H. Bunnell et al., J. Org. Chem., 55, 768 (1990)), tetrabutylammonium dihydrogentrifluoride/N-bromosuccinimide (Laid-open Japanese Patent Publication No. Hei 5–255165) and (HF) n-pyridine to produce compound (32) of the present invention.

As shown in scheme 10, compound (37) of the present invention can be produced by converting compound (33) into compound (35) by the method of N. Petraganani et al. (Synthesis, 112 (1977)), reducing it with a reducing agent such as LAH, SBH/AlCl$_3$, lithium borohydride, and bis(2-methoxyethoxy)aluminum sodium hydride, and then subjecting together with compound (15) to a dehydration reaction in the presence of an acidic catalyst such as PTS.

As shown in scheme 11, compound (38) is converted into compound (39) with a peroxide such as peracetic acid (D. Swern et al., J. Am. Chem. Soc., 68, 1504 (1946)), perbenzoic acid (J. Grigor et al., J. Chem. Soc., 2333, (1954)), trifluoroperacetic acid (E. J. Corey et al., J. Am. Chem. Soc., 101, 5841 (1979)), m-chloroperbenzoic acid (mCPBA) (A. G. Hortmann et al., J. Org. Chem., 35, 4920 (1970) and M. Sworin et al., J. Am. Chem. Soc., 111, 1815 (1989)), and then the compound (39) is hydrolyzed with trifluroacetic acid (A. C. Cope et al., J. Am. Chem. Soc., 85, 3752 (1963)), trichloroacetic acid (G. Berti et al., Tetrahedron Lett., 3421 (1965)), or trinitrobenzenesufonic acid (M. A. Khuddus et al., J. Am. Chem. Soc., 95, 8393 (1973)) to convert into compound (40).

Terminal —OH of the compound (40) is protected with tert-butyldimethylsilyl chloride (TBDMS-Cl) (K. K. Oglivie et al., Tetrahedron Lett., 317 (1973) and S. K. Chaudhary et al., Tetrahedron Lett., 99 (1979)) and the like, led to trifluoromethanesulfonic acid ester (T. Gramstad et al., J. Chem. Soc., 4069 (1957)), sulfonic acid ester (Ogura et al., Bull. Chem. Soc. Jpn., 56, 1257 (1983), or oxalic acid ester (E. E. Smissman et al., J. Org. Chem., 37, 3944 (1972)), and then reacted with compound (43) to convert into compound (44).

Compound (46) of the present invention can be produced by deprotecting the TBDMS portion in the compound (44) (I. J. Bolton et al., J. Chem. Soc., 2944 (1971)), and then subjecting it to a dehydration reaction in the presence of an acid catalyst such as PTS.

As shown in scheme 12, compound (47) is oxidized with an oxidizing agent such as pyridinium chlorochromate (PCC) (G. Melvin et al., J. Chem. Soc., Perkin Trans., 1, 599 (1981)) and pyridinium dichromate, and then reacted with compound (48) to obtain compound (49). Subsequently, the compound (49) is dehydrated in the presence of an acid catalyst such as a mineral acid, for example, hydrochloric acid and sulfuric acid, and PTS (W. J. Johnson et al., J. Am. Chem. Soc., 83, 606 (1961)) to obtain compound (50). The compound (50) is reduced with a reducing agent such as diisobutylaluminum hydride (DIBAL) (E. J. Corey et al., J. Am. Chem. Soc., 91, 5675 (1969)) and sodium bis(2-methoxyethoxy)aluminum hydride (Tokoroyama et al, Tetrahedron Lett., 36, 3377 (1980)) to obtain compound (51). Further, the compound (51) is reduced with a hydrosilane such as triethylsilane (G. A. Kraus et al., J. Chem. Soc., Chem. Commun., 1568 (1986)) to obtain compound (52) of the present invention.

As shown in scheme 13, compound (56) of the present invention can be produced by converting compound (53) into compound (54) by the method of A. W. Dox (Org. Synth., 1, 5 (1941)), and then treating by the method of A. Boller et al. (Mol. Cryst. Liq. Cryst., 42, 215 (1977)).

As shown in scheme 14, compound (60) of the present invention can be produced by the method described in Laid-open Japanese Patent Publication No. Sho 61-58474.

Compounds expressed by the general formula (1) having silacyclohexane ring therein can readily be produced according to the method disclosed in Laid-open Japanese Patent Publication No. Hei 7-70148, Laid-open Japanese Patent Publication No. Hei 7-112990, Laid-open Japanese Patent Publication No. Hei 7-173176, or Laid-open Japanese Patent Publication No. Hei 7-252273.

While starting materials having benzene ring in which chlorine atom is introduced (for example, 1-bromo-3-chlorobenzene or 1-bromo-3-chloro-5-fluorobenzene) are commercially available, they can be purchased to use. However, it is possible to introduce chlorine atom into $A_1$ to $A_4$ at any stage of schemes 1 to 13, for instance, by chlorination of hydroxyl group (G. A. Wiley et al., J. Am. Chem. Soc., 86, 964 (1946)), the Sandmeyer reaction (H. Becker et al., "Organikum", VEB Deutscher Verlag der Wissenschaften, 591 (1973)), the method described in DE 4,219,819, or the method of V. Bezbordov et al., (Liq. Cryst., 20 (1), 1 (1996)).

Also, starting materials having an alkyl group in which fluorine atom is introduced are available on the market. However, as the methods by which fluorine atom is introduced into Ra and/or Rb, the following methods can be shown:

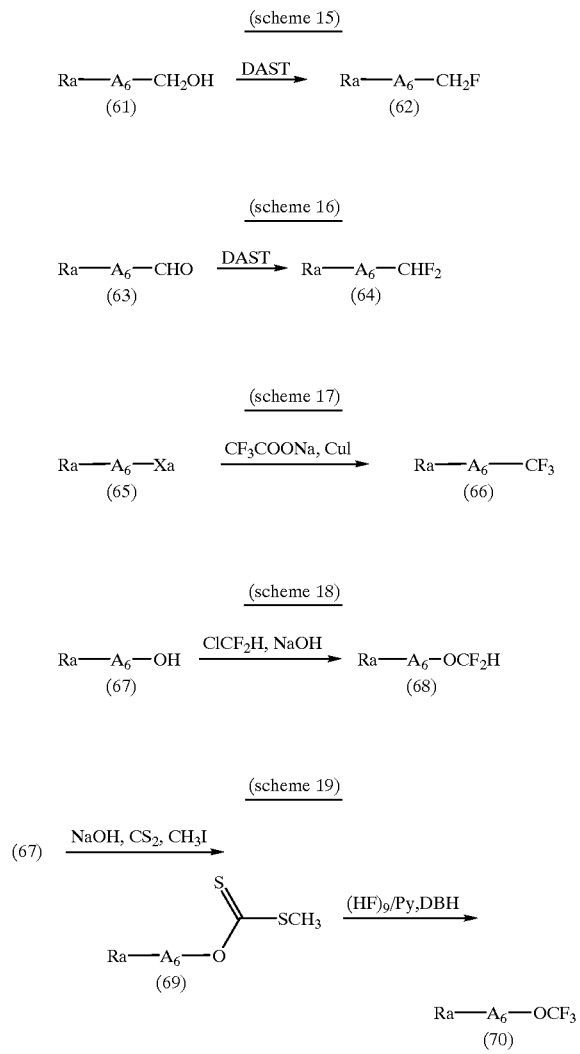

in schemes 15 to 19, Ra and Xa have the same meaning as described above, and $A_6$ represents the following group:

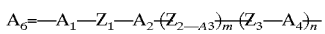

wherein $A_1$ to $A_4$, $Z_1$ to $Z_3$, m, and n have the same meaning as described above.

That is, as shown in scheme 15, compound (62) can be produced by fluorinating compound (61) with a fluorinating agent such as diethylaminosulfur trifluoride (DAST) (W. J. Middleton et al, J. Org. Chem., 40, 574 (1975), S. Rozen et al., Tetrahedron Lett., 41, 111 (1985), M. Hudlicky, org. React., 35, 513 (1988), and P. A. Messina et al., J. Fluorine Chem., 42, 137 (1989)), morphorinosulfur trifluoride (K. C. Mange et al., J. Fluorine Chem., 43, 405 (1989)), and diethylaminehexafluoropropene (Ishikawa et al., Bull. Chem. Soc. Jpn., 52, (11), 3377 (1979)).

As shown in scheme 16, compound (64) can be produced by fluorinating compound (63) with DAST or the like.

As shown in scheme 17, compound (66) can be produced by reacting compound (65) with sodium trifluoroacetate/copper (I) iodide (G. E. Carr et al., J. Chem. Soc., Perkin Trans. 1, 921 (1988)) or methyl fluorosulfonyldifluoroacetate/copper (I) iodide (Q. Y. Chen et al., J. Chem. Soc., Chem. Commun, 705 (1989)).

As shown in scheme 18, compound (68) can be produced by reacting compound (67) with chlorodifluoromethane/sodium A hydroxide (Tokuhyo (Laid-open Japanese WO publication) No. Hei 3-500413). Alternatively, compound (68) can be produced even by the method of Chen et al. (J. Fluorine Chem., 44, 433 (1989).

As shown in scheme 19, compound (67) is converted into compound (69) by the method of Albert et al. (Synth. Commun., 19, 547 (1989)). This compound can be fluorinated by the method of Kurohoshi et al. (Tetrahedron Lett., 33 (29), 4173 (1992) to A produce compound (70).

Compounds of the present invention can be produced by using the reactions described above in a suitable combination depending on the qualities of the compounds.

While all of the reactions described above are known in public, it is needless to say that other known reactions can further be used when necessary.

Liquid crystalline compounds of the present invention obtained by such methods as described above have an extremely high voltage holding ratio and a low threshold voltage, are considerably small in their dependency on temperature, have a low Δn, are readily mixed with various liquid crystal materials, and have a remarkably excellent miscibility even at low temperatures.

Besides, the liquid crystalline compounds of the present invention are sufficiently stable physically and chemically under conditions in which liquid crystal display devices are ordinarily used, and are considerably excellent as component of nematic liquid crystal compositions.

Liquid crystalline compounds of the present invention can preferably be used as component even in liquid crystal compositions for TN, STN, TFT, and other display modes.

Whereas some of the compounds of the present invention exhibit a negative dielectric anisotropy value (Δ∈), these compounds can be very preferably used as component of liquid crystal compositions for IPS mode or VA mode.

Among the compounds expressed by the general formula (1), compounds having 2 six-membered rings exhibit a comparatively low phase transition temperature to isotropic phase and a low viscosity, and compounds having three or four six-membered rings exhibit a high phase transition temperature to isotropic phase and a rather high viscosity. Compounds having cyclohexane ring, dioxane ring, tetrahydropyran ring, or silacyclohexane ring in the molecule exhibit a low Δn, compounds having cyclohexane ring, silacyclohexane ring, or benzene ring exhibit a low viscosity, compounds having benzene ring, pyridine ring, or pyrimidine ring exhibit a wide temperature range of liquid crystal phase and high Δn, and the compounds having pyridine ring, pyrimidine ring or dioxane ring exhibit a comparatively high Δ∈.

Since the compounds having double bond in Ra, Rb and/or $Z_1$ to $Z_3$ exhibit a large elastic constant ratio (bend elastic constant/splay elastic constant) and a low viscosity, liquid crystal compositions which are steep in the change of transmittance in T-V curve can be produced when such compounds are used as component of liquid crystal compositions for STN, and display devices having a high contrast can be provided. Compounds having triple bond exhibit a high Δn and low viscosity, Compounds having dihydrosilyl group (—SiH$_2$—) exhibit a low threshold voltage and low viscosity.

Compounds in which Ra and/or Rb is an optically active group are particularly useful as chiral dopant. When Rb is a halogen atom, halogen substituted alkyl group, or halogen substituted alkoxy group, the compounds exhibit a high Δ∈ and when it is cyano group, the compounds exhibit a particularly high Δ∈.

It is possible to make A E higher by replacing the hydrogen atom in the ring structure by fluorine atom, and miscibility is improved at the same time.

Compounds having difluoromethylenoxy group (—CF$_2$O—) or oxydifluoromethylene group (—OCF$_2$—) in at least one of Z$_1$ to Z$_3$ exhibit a comparatively high Δ∈ and a low viscosity, and the compounds in which it is 1,2-diflurovinylene (—CF═CF—) exhibit a remarkably low viscosity.

Also, the compounds of the present invention in which an atom is replaced by its isotope can be said to be preferable since such compounds also exhibit similar characteristics.

Based on these facts, new liquid crystalline compounds having desired physical properties can be obtained by selecting proper rings, substituents, and bonding groups.

Now, the liquid crystal compositions of the present invention are described. Liquid crystal compositions of the present invention preferably comprise at least one compound expressed by the general formula (1) in the ratio of 0.1 to 99.9% by weight to develop excellent characteristics, and the ratio is more preferably 1 to 60% by weight.

In more detail, the liquid crystal compositions provided by the present invention are completed by mixing compounds selected from the group consisting of the compounds each expressed by one of the general formulas (2) to (12) depending on the purposes of the liquid crystal compositions, in addition to the first component comprising at least one compound expressed by the general formula (1).

As preferable examples of the compounds used in the liquid crystal compositions of the present invention and expressed by one of the general formulas (2) to (4), the following compounds can be mentioned:

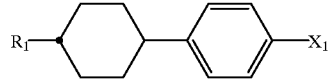

(2-1)

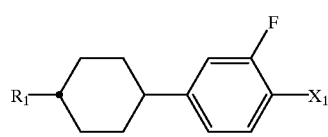

(2-2)

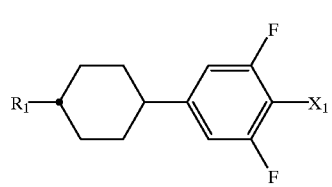

(2-3)

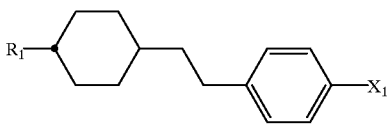

(2-4)

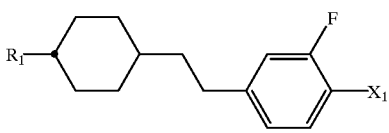

(2-5)

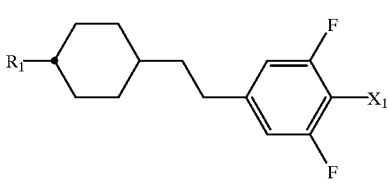

(2-6)

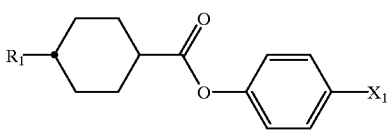

(2-7)

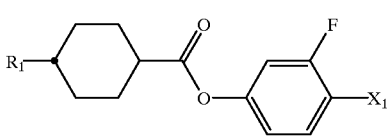

(2-8)

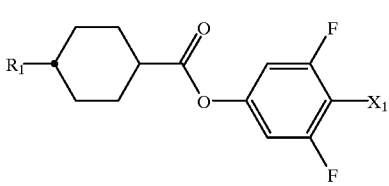

(2-9)

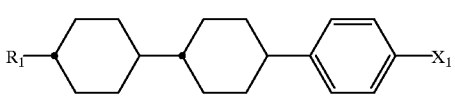

(3-1)

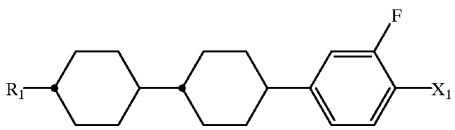

(3-2)

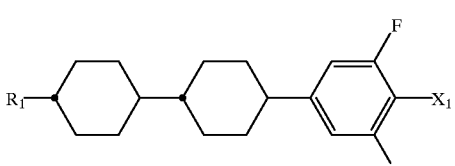

(3-3)

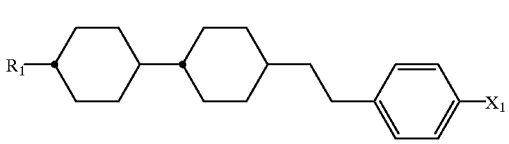

(3-4)

(3-5)
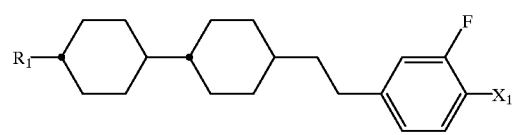
(3-6)
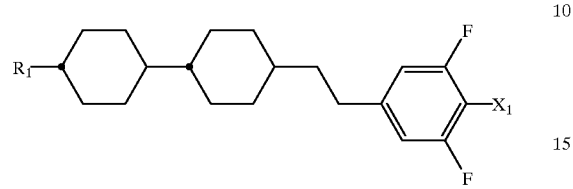
(3-7)
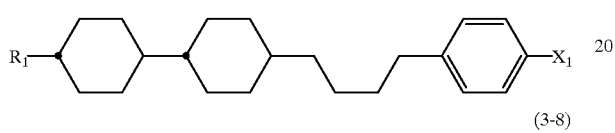
(3-8)
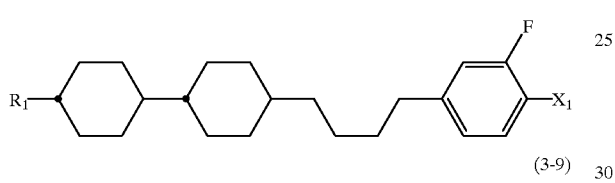
(3-9)
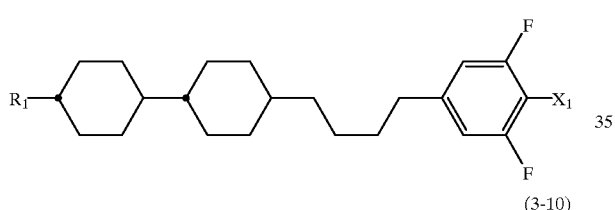
(3-10)
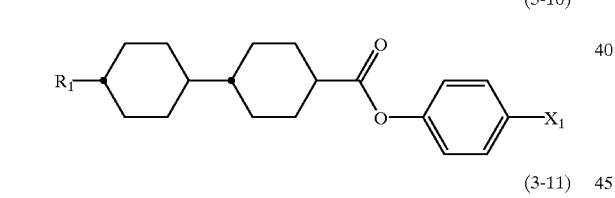
(3-11)
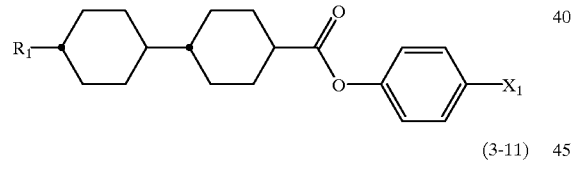
(3-12)
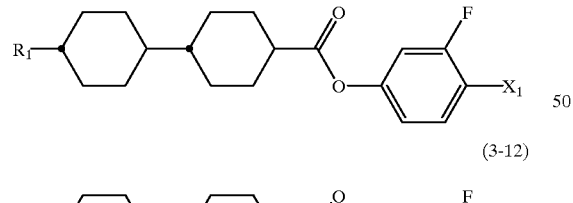
(3-13)
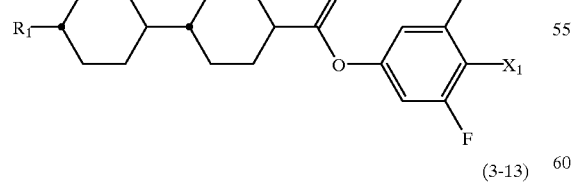
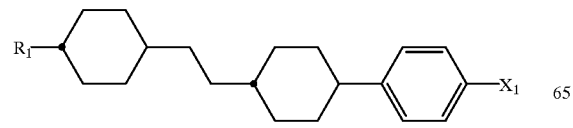
(3-14)
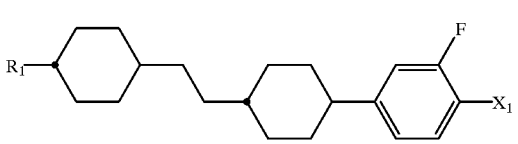
(3-15)
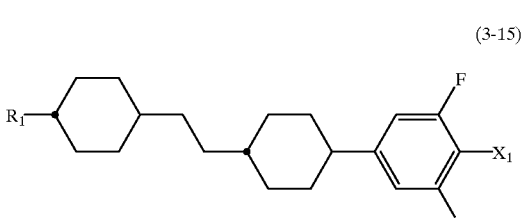
(3-16)
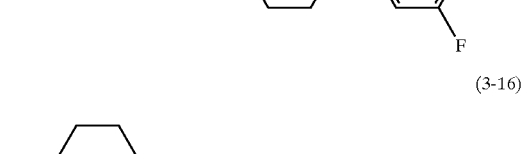
(3-17)
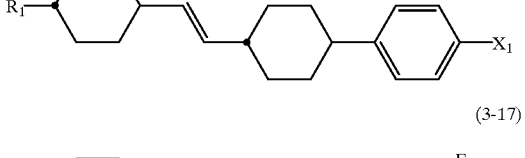
(3-18)
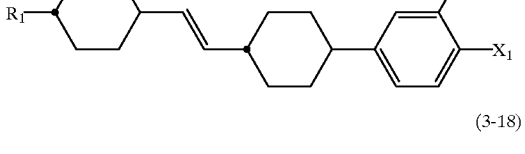
(3-19)
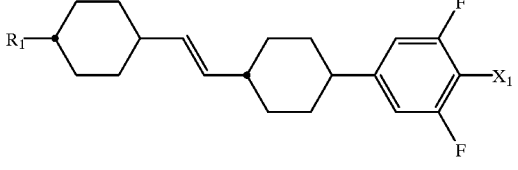
(3-20)
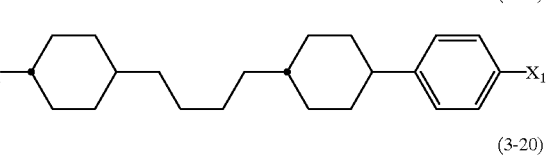
(3-21)
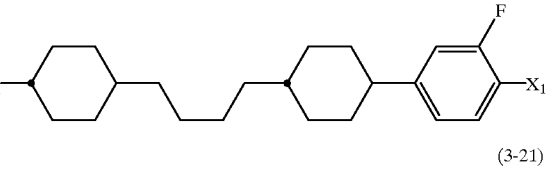
(3-22)
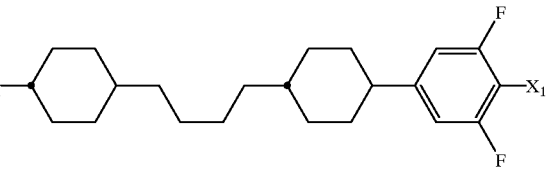
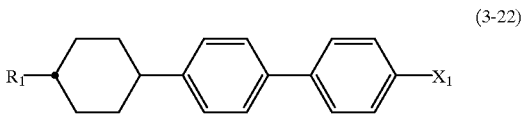

-continued
(3-23) 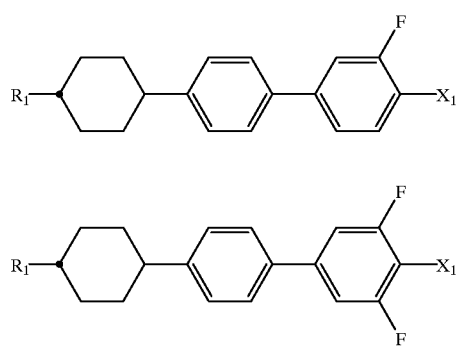
(3-24)
(3-25) 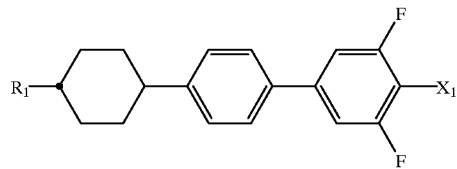
(3-26)
(3-27) 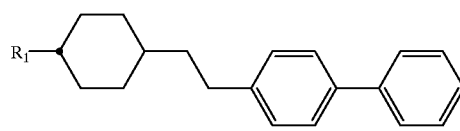
(3-28) 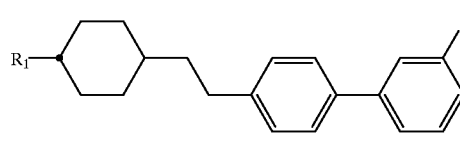
(3-29)
(3-30)
(3-31) 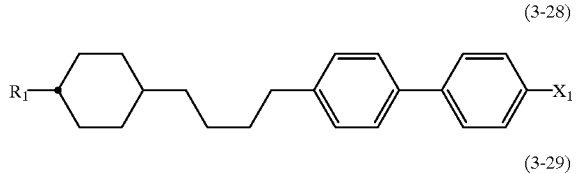
-continued
(3-32) 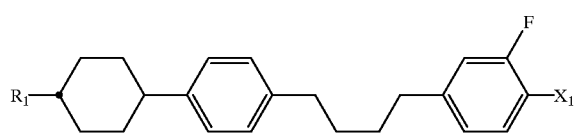
(3-33)
(3-34) 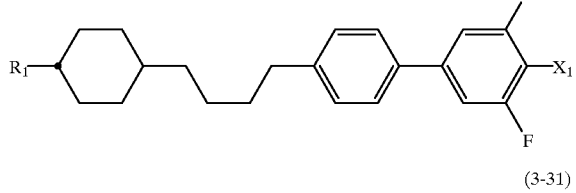
(3-35)
(3-36)
(3-37) 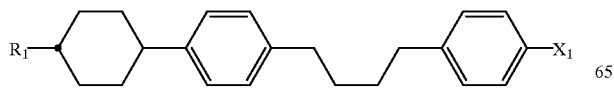
(3-38) 
(3-39) 

(3-40)
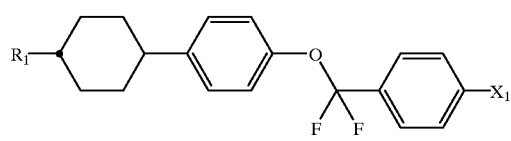
(3-41)
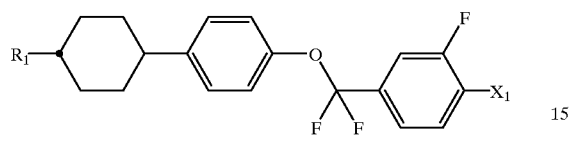
(3-42)
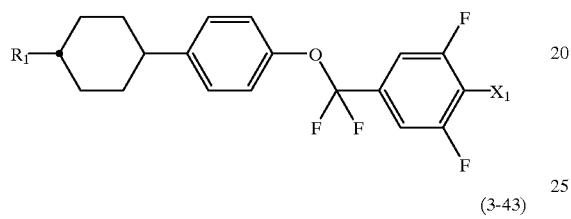
(3-43)
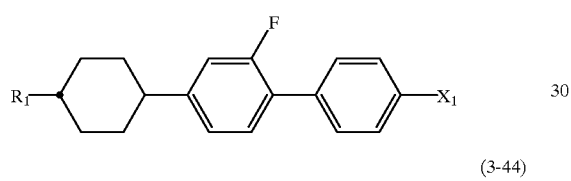
(3-44)
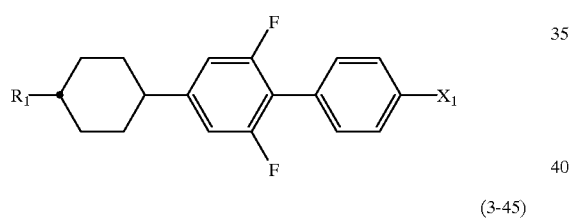
(3-45)
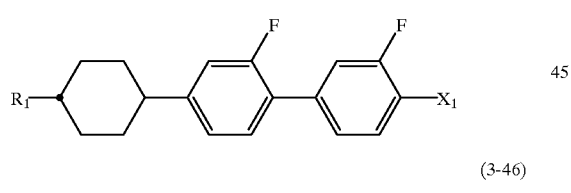
(3-46)
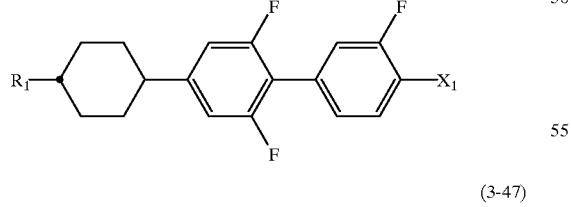
(3-47)
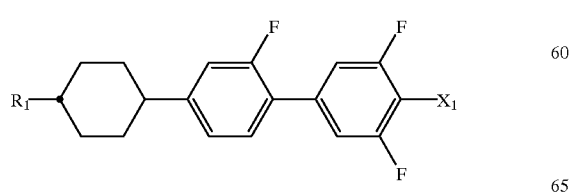
(3-48)
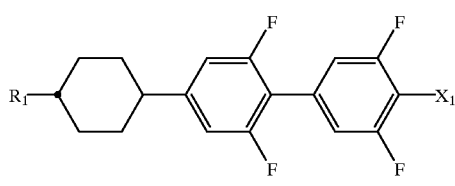
(3-49)
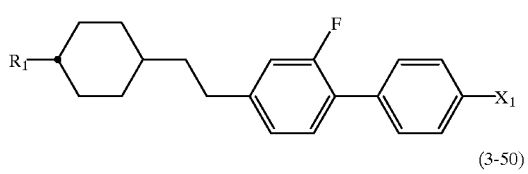
(3-50)
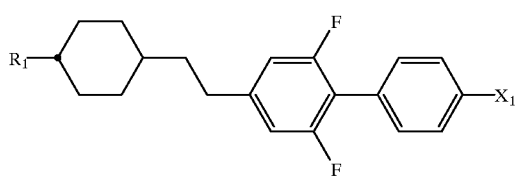
(3-51)
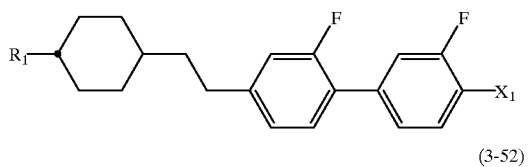
(3-52)
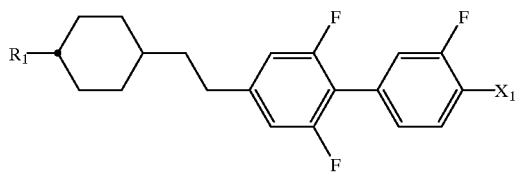
(3-53)
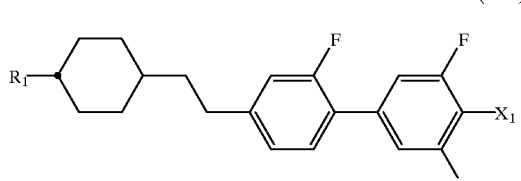
(3-54)
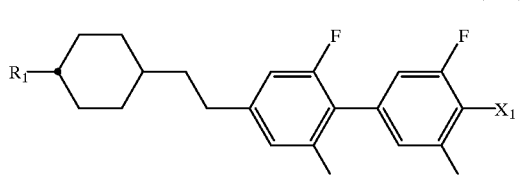
(3-55)

(3-56)
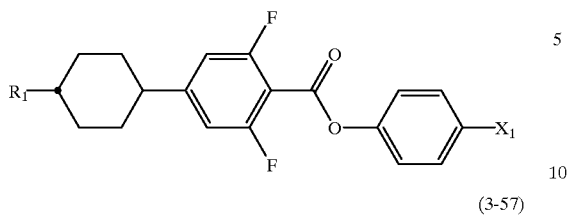
(3-57)
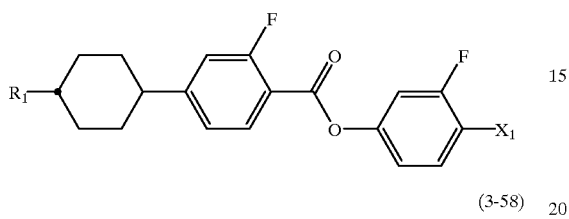
(3-58)
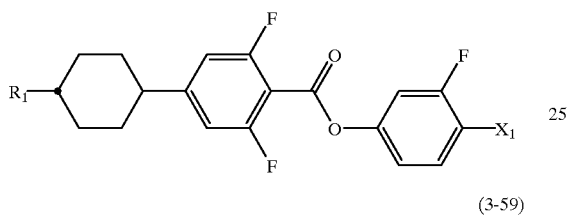
(3-59)
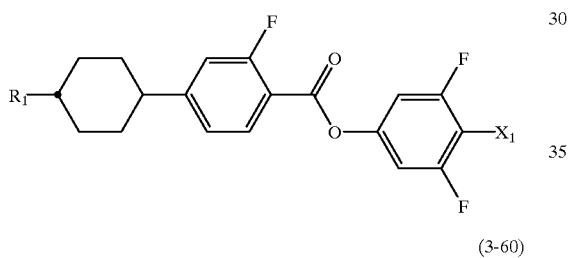
(3-60)
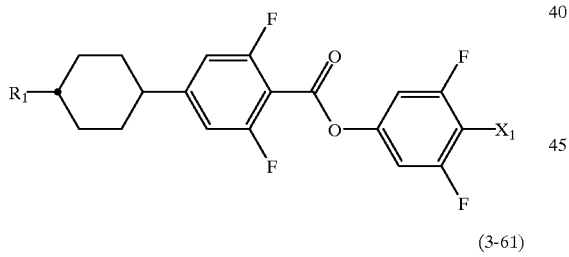
(3-61)
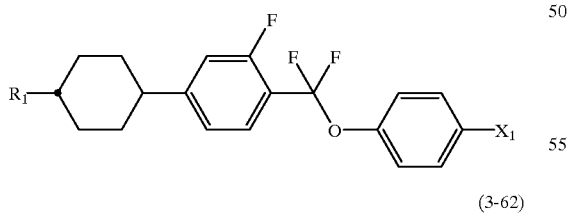
(3-62)
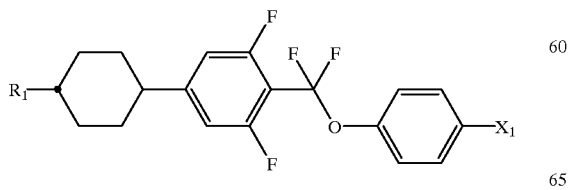
(3-63)
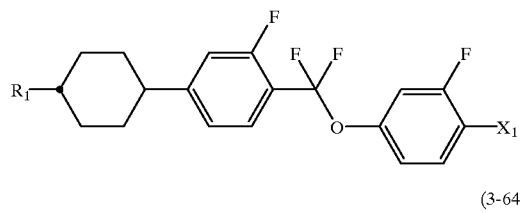
(3-64)
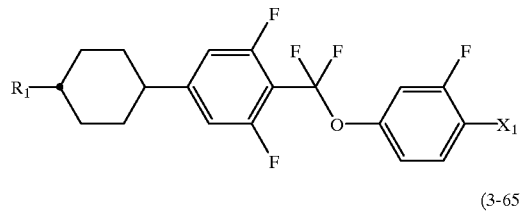
(3-65)
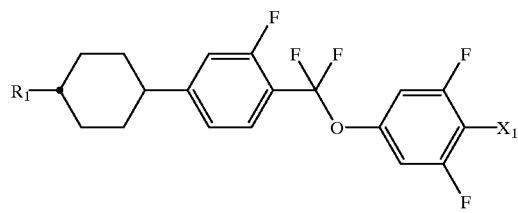
(3-66)
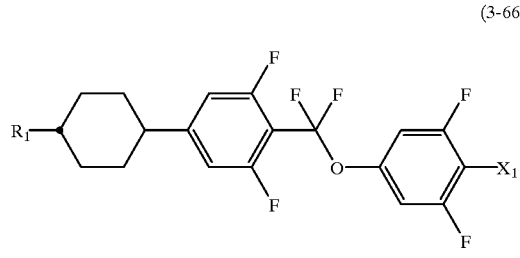
(3-67)
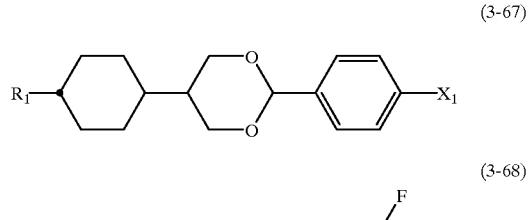
(3-68)
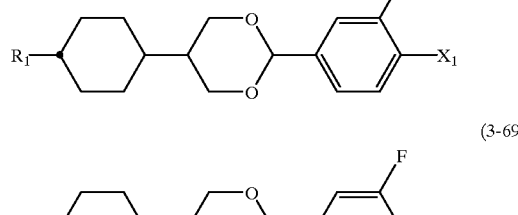
(3-69)
(4-1)
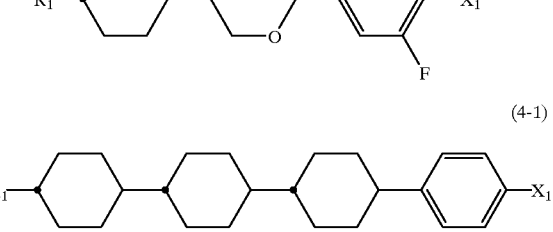

(4-2)
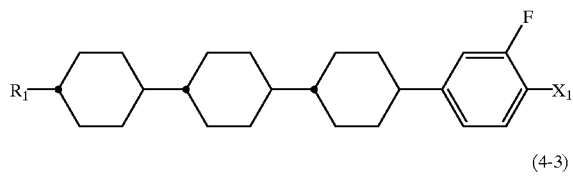
(4-3)
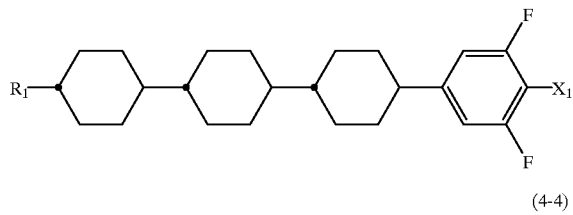
(4-4)
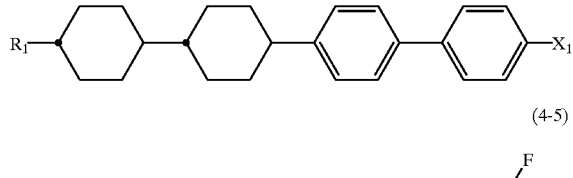
(4-5)
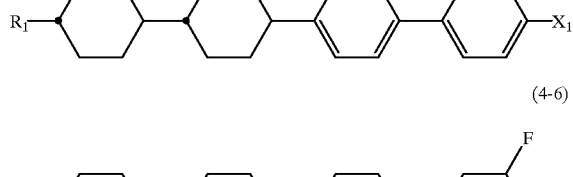
(4-6)
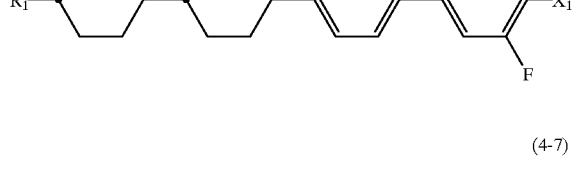
(4-7)
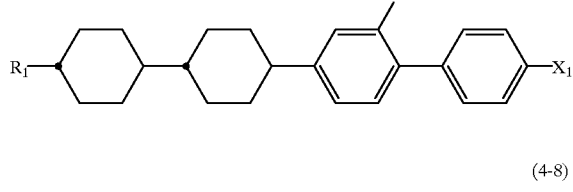
(4-8)
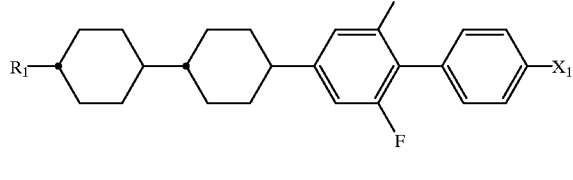
(4-9)
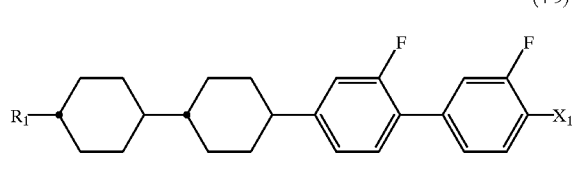
(4-10)
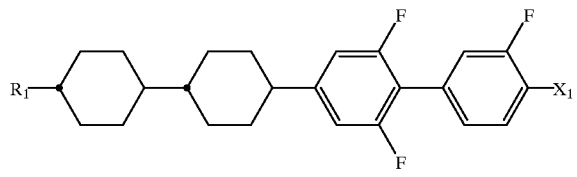
(4-11)
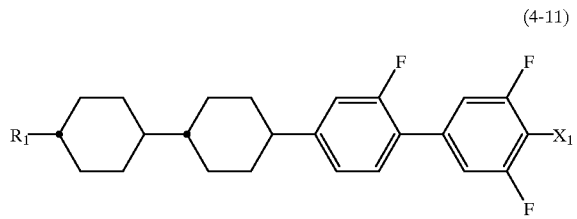
(4-12)
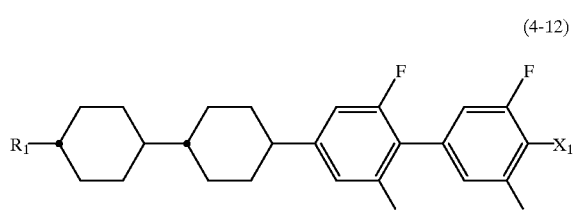
(4-13)
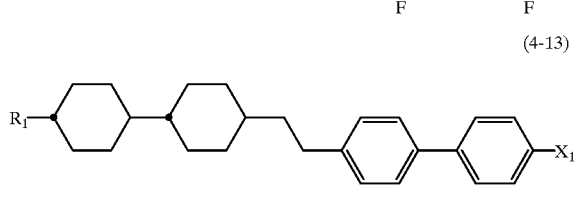
(4-14)
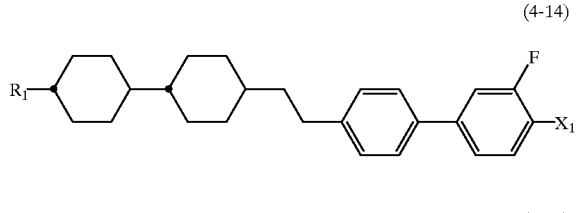
(4-15)
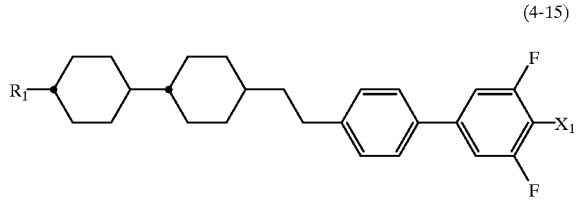
(4-16)
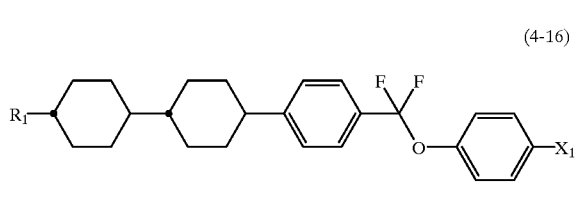
(4-17)
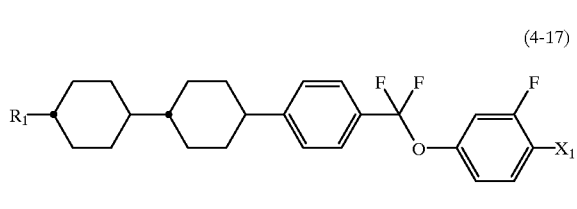

-continued

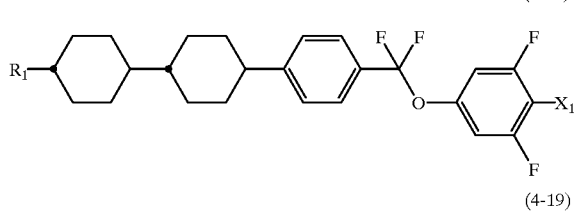
(4-18)

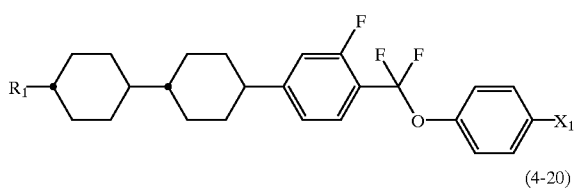
(4-19)

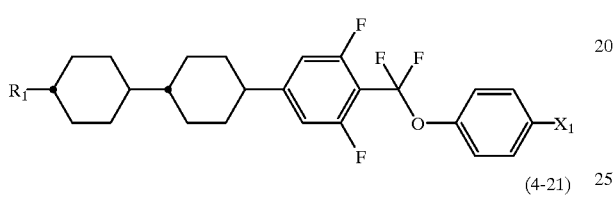
(4-20)

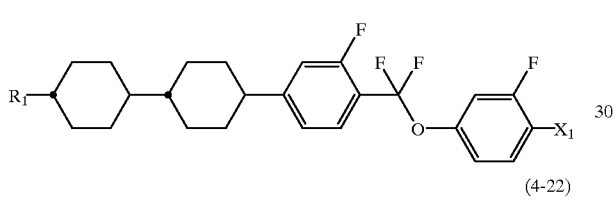
(4-21)

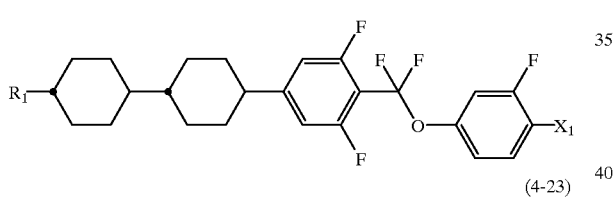
(4-22)

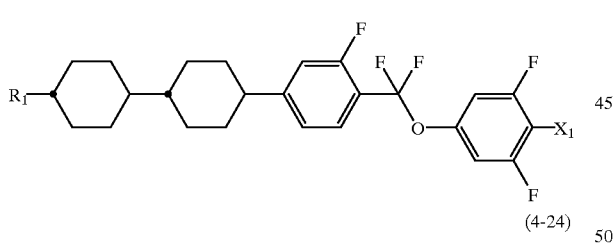
(4-23)

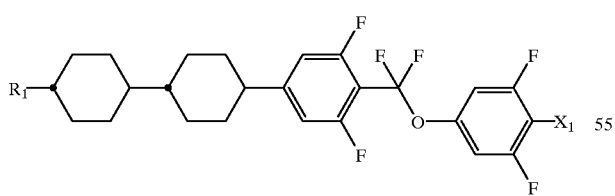
(4-24)

wherein $R_1$ and $X_1$ have the same meaning as described above.

Compounds expressed by one of the general formulas (2) to (4) have a positive dielectric anisotropy value, are considerably excellent in thermal stability and chemical stability, and are extremely useful when liquid crystal compositions for TFT of which a high reliability such as a high voltage holding ratio or large specific resistivity is required in particular are produced.

When the liquid crystal compositions for TFT are produced, the compounds expressed by one of the general formulas (2) to (4) can be used in the range of 0.1 to 99.9% by weight, and the range is preferably 10 to 97% by weight and more desirably 40 to 95% by weight. The compositions may further comprise a compound expressed by one of the general formulas (7) to (9) for the purpose of adjusting viscosity.

While a compound expressed by one of the general formulas (2) to (4) can be used even when liquid crystal compositions for STN or TN are produced, the amount is preferably less than 50% by weight.

As preferable examples of the compounds used in the liquid crystal compositions of the present invention and expressed by the general formula (5) or (6), the following compounds can be mentioned:

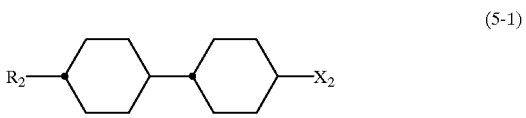
(5-1)

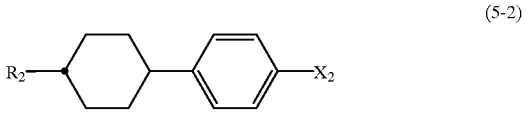
(5-2)

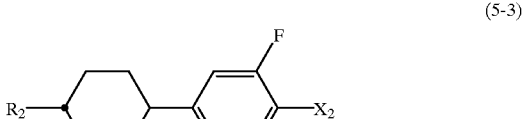
(5-3)

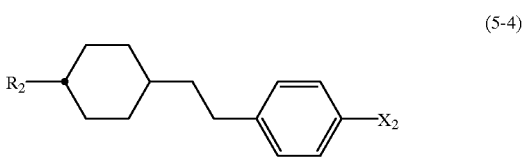
(5-4)

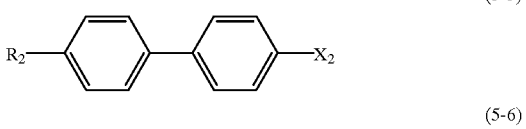
(5-5)

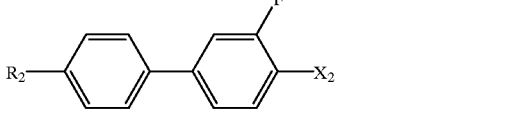
(5-6)

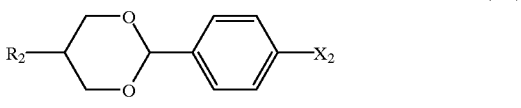
(5-7)

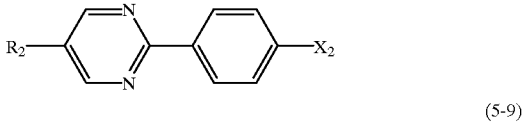
(5-8)

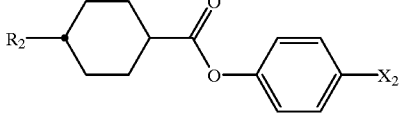
(5-9)

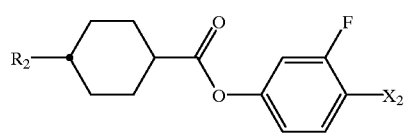 (5-10)
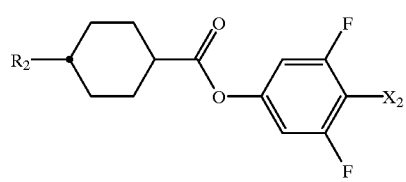 (5-11)
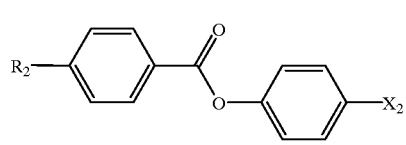 (5-12)
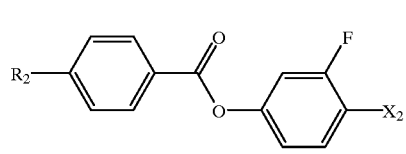 (5-13)
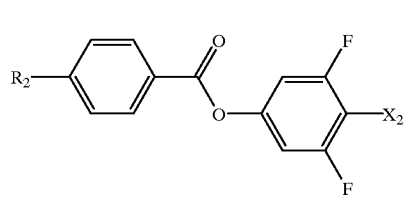 (5-14)
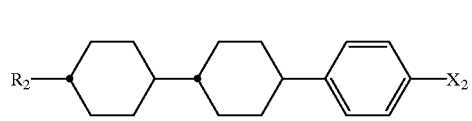 (5-15)
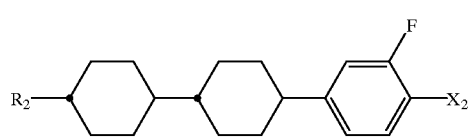 (5-16)
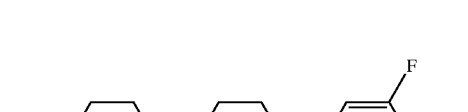 (5-17)
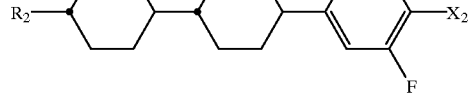 (5-18)
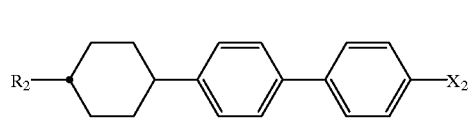 (5-19)
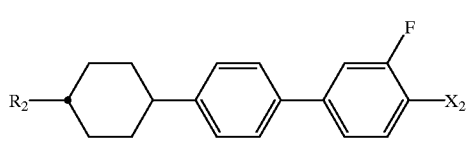 (5-19)
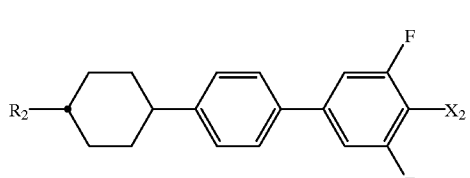 (5-20)
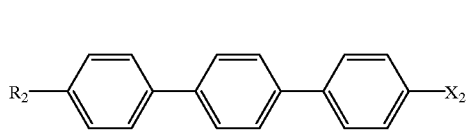 (5-21)
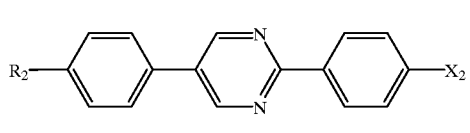 (5-22)
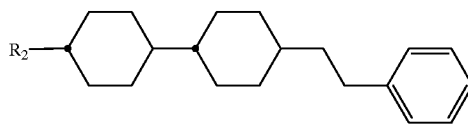 (5-23)
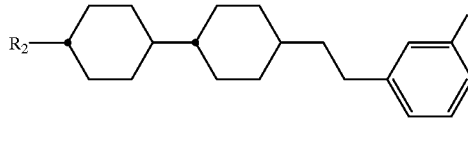 (5-24)
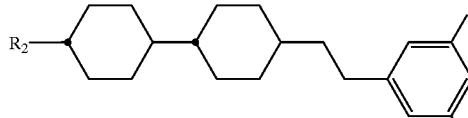 (5-25)
 (5-26)
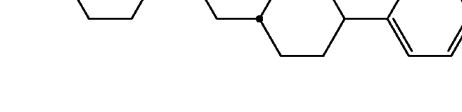 (5-27)
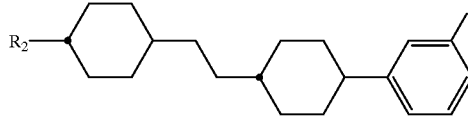

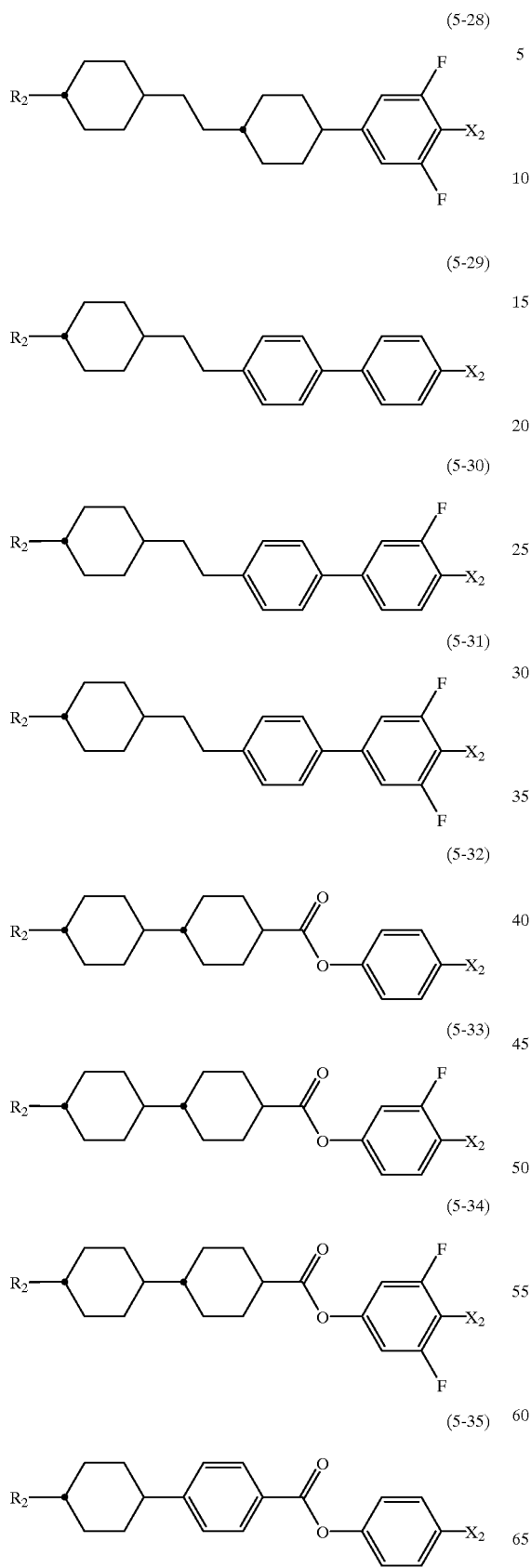
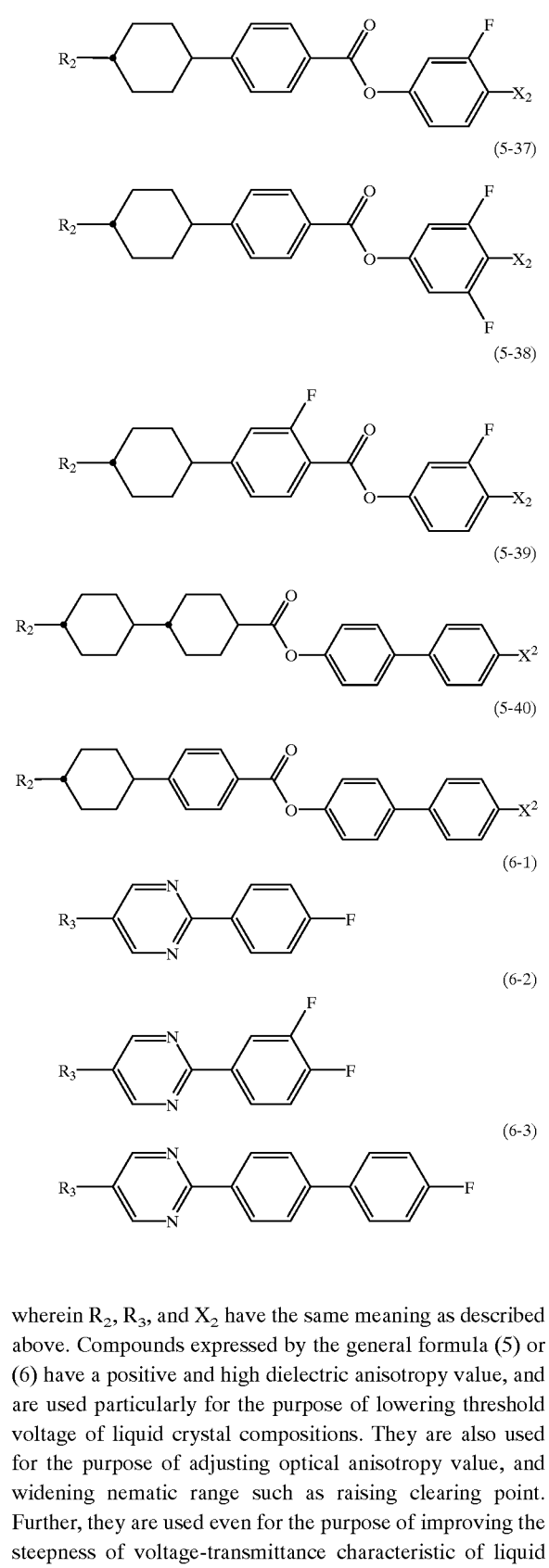

wherein $R_2$, $R_3$, and $X_2$ have the same meaning as described above. Compounds expressed by the general formula (5) or (6) have a positive and high dielectric anisotropy value, and are used particularly for the purpose of lowering threshold voltage of liquid crystal compositions. They are also used for the purpose of adjusting optical anisotropy value, and widening nematic range such as raising clearing point. Further, they are used even for the purpose of improving the steepness of voltage-transmittance characteristic of liquid crystal compositions for STN or TN.

Compounds expressed by the general formula (5) or (6) are particularly useful when liquid crystal compositions for STN or TN are produced.

Whereas when the amount of the compounds expressed by the general formula (5) or (6) is increased in liquid crystal compositions, threshold voltage of the liquid crystal compositions lowers, viscosity increases. Accordingly, it is advantageous to use a large amount of the compound since the go driving at a low voltage is possible, so far as viscosity of the liquid crystal compositions satisfies a required value. When liquid crystal compositions for STN or TN are produced, compounds expressed by the general formula (5) or (6) can be used in the range of 0.1 to 99.9% by weight, and the range is preferably 10 to 97% by weight and more desirably 40 to 95% by weight.

As preferable examples of the compounds used in the liquid crystal compositions of the present invention and expressed by one of the general formulas (7) to (9), the following compounds can be mentioned:

(7-1)
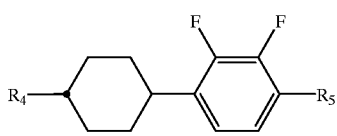

(7-2)
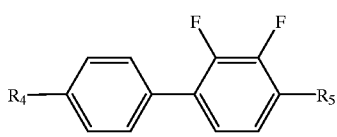

(7-3)
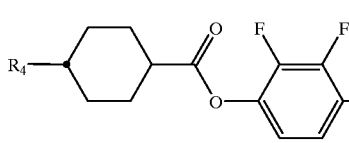

(8-1)
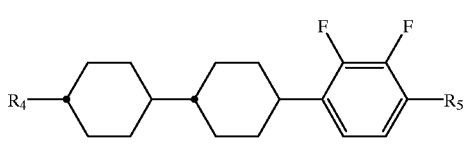

(8-2)
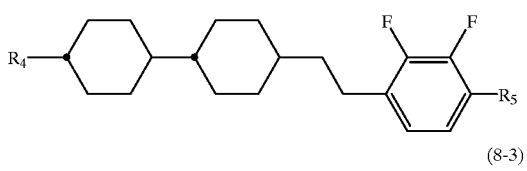

(8-3)
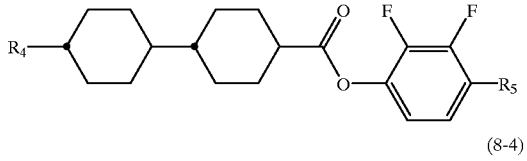

(8-4)
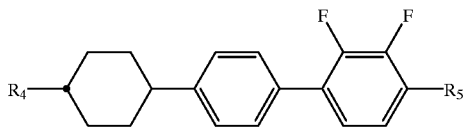

(8-5)
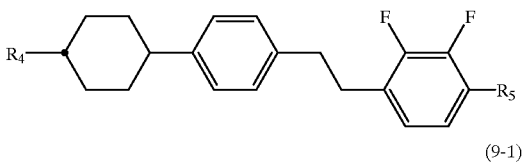

(9-1)
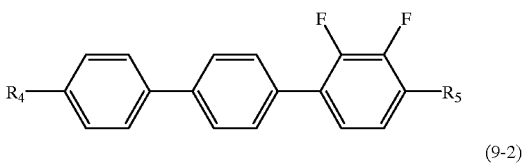

(9-2)
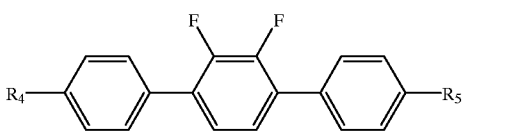

(9-3)
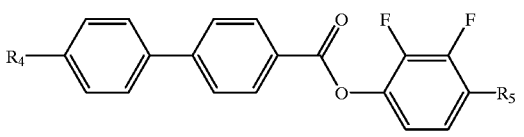

wherein $R_4$ and $R_5$ have the same meaning.

Compounds expressed by one of the general formulas (7) to (9) have a negative dielectric anisotropy value. Since the compounds expressed by the general formula (7) are two-rings compounds, they are used principally for the purpose of adjusting threshold voltage, adjusting viscosity, or adjusting optical anisotropy value. Compounds expressed by the general formula (8) are used for the purpose of widening nematic range such as raising clearing point or adjusting optical anisotropy value. Compounds expressed by the general formula (9) are used for the purpose of lowering threshold voltage and for the purpose of increasing optical anisotropy value, in addition to the purpose of widening nematic range.

Compounds expressed by one of the general formulas (7) to (9) are used principally for liquid crystal compositions having a negative dielectric anisotropy value. When the amount of the compounds to be used is increased, threshold voltage of liquid crystal compositions lowers and viscosity increases. Accordingly, it is desirable to use the compounds in a small amount so far as threshold voltage satisfies a required value. However, since their absolute value of dielectric anisotropy is lower than 5, low voltage driving sometimes becomes impossible when their amount becomes less than 40% by weight. While the amount of the compound expressed by one of the general formulas (7) to (9) to be used is preferably more than 40% by weight when liquid crystal compositions for TFT having a negative dielectric anisotropy are produced, the amount is preferably 50 to 95% by weight. Further, the compound expressed by one of the general formulas (7) to (9) is sometimes mixed to liquid crystal compositions having a positive dielectric anisotropy value for the purpose of controlling voltage-transmittance characteristic of the compositions. In this case, the amount of the compounds expressed by one of the general formulas (7) to (9) to be used is preferably less than 30% by weight.

As preferable examples of the compounds used in the liquid crystal compositions of the present invention and expressed by one of the general formulas (10) to (12), the following compounds can be mentioned:
(10-1)
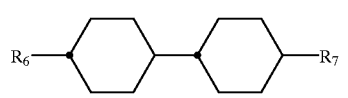
(10-2)
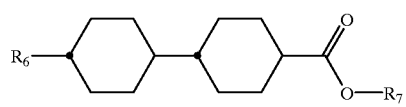
(10-3)
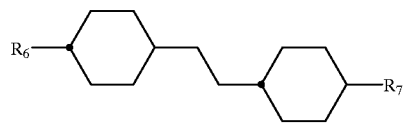
(10-4)
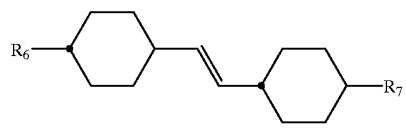
(10-5)
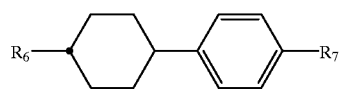
(10-6)
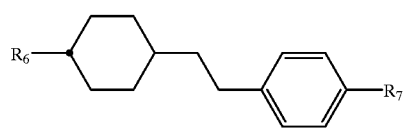
(10-7)
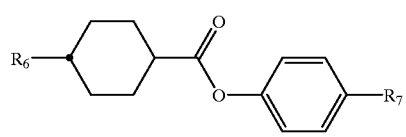
(10-8)
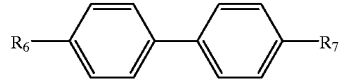
(10-9)
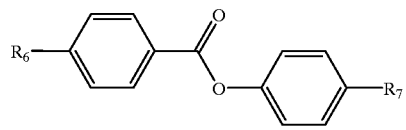
(10-10)
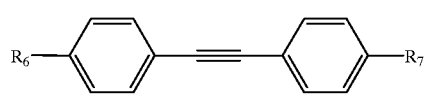
(10-11)
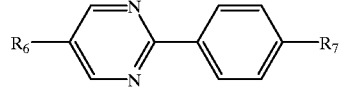
-continued
(11-1)
(11-2)
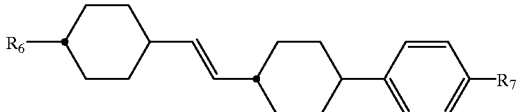
(11-3)
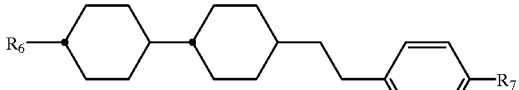
(11-4)
(11-5)
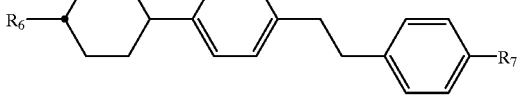
(11-6)
(11-7)
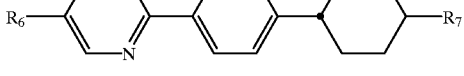
(11-8)
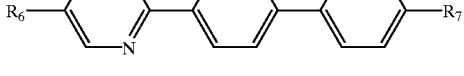
(11-9)
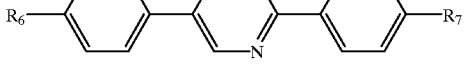
(11-10)
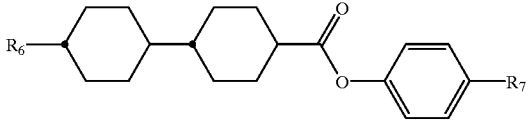

(11-11)
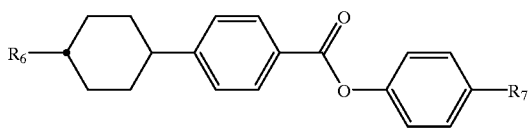

(11-12)
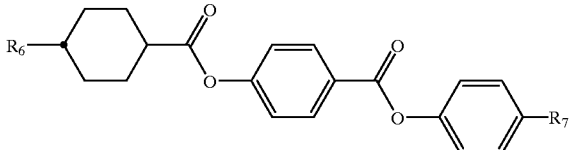

(11-13)
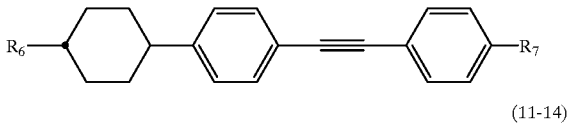

(11-14)
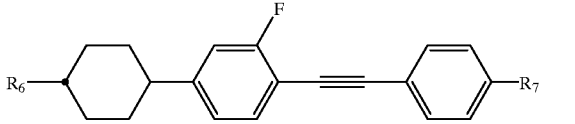

(11-15)
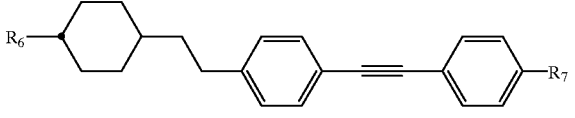

(11-16)
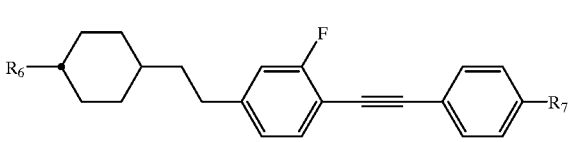

(11-17)
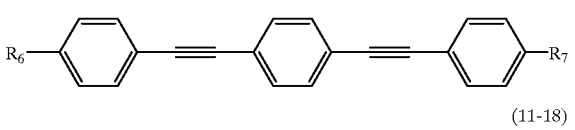

(11-18)
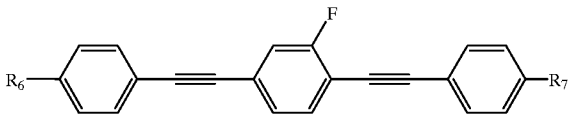

(12-1)
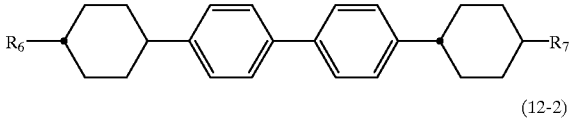

(12-2)
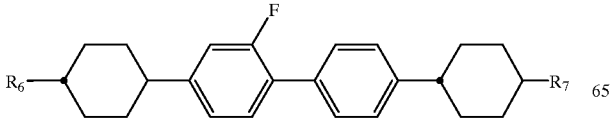

(12-3)
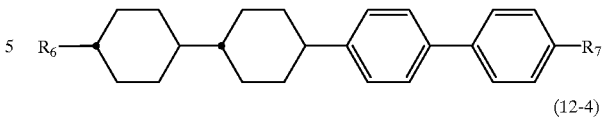

(12-4)
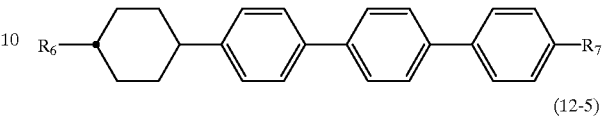

(12-5)
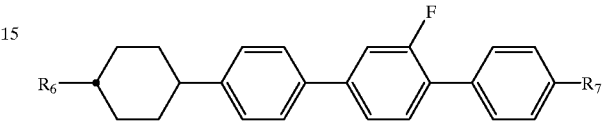

(12-6)
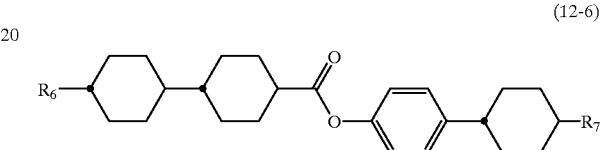

wherein $R_6$ and $R_7$ have the same meaning as described above.

Compounds expressed by one of the general formulas (10) to (12) have a small absolute value of dielectric anisotropy and are close to neutral. Compounds expressed by the general formula (10) are used principally for the purpose of adjusting viscosity or adjusting optical anisotropy value. Compounds expressed by the general formula (11) or (12) are used for the purpose of widening nematic range such as raising clearing point or for the purpose of adjusting optical anisotropy value.

When the compounds expressed by one of the general formulas (10) to (12) to be used is increased, threshold voltage of liquid crystal compositions rises and viscosity reduces. Accordingly, it is desirable to use the compounds in a large amount so far as threshold voltage of liquid crystal compositions satisfies a required value. When liquid crystal compositions for TFT are produced, the amount of the compound to be used is preferably less than 40% by weight and more desirably less than 35% by weight. When liquid crystal compositions for STN or TN are produced, the amount of the compounds expressed by one of the general formulas (10) to (12) to be used is preferably less than 70% by weight and more desirably less than 60% by weight.

With the exception of such specific cases as liquid crystal compositions for OCB (optically Compensated Birefringence) mode and the likes, an optically active compound is usually added to the liquid crystal compositions of the present invention for the purpose of inducing helical structure of liquid crystal composition to adjust required twist angle and to prevent reverse twist. For such purposes, any known optically active compounds can be used, but the following optically active compounds can be mentioned as preferable examples:

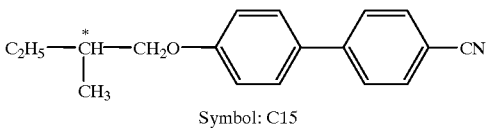

Symbol: C15

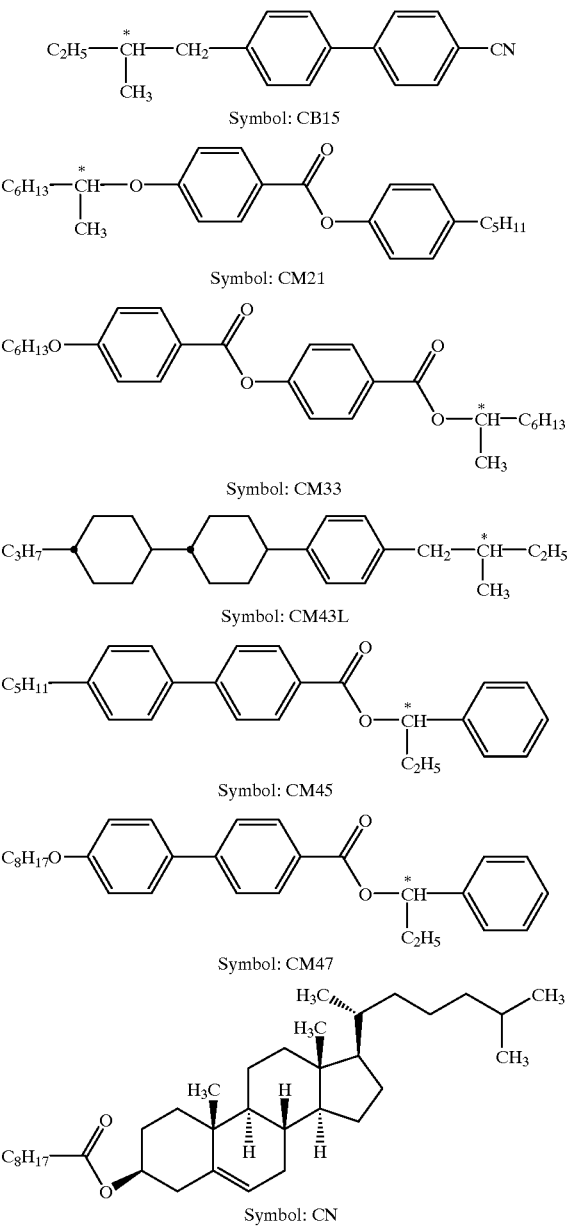

anthraquinone type, and tetrazine type thereto. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

As examples of liquid crystal compositions comprising the compound of the present invention, the following can be mentioned. The compounds in Composition Examples, and Examples described below are designated by symbolizing them according to the definition shown below, and the compound No. in Composition Examples is given in the same rule as that shown in Examples.

| Ring structure | Symbol |
|---|---|
| | B |
| | B(2F) |
| | B(3F) |
| | B(2Cl) |
| | B(3Cl) |
| | B(2,3F) |
| | (B2,3Cl) |

These optically active compounds are usually added to liquid crystal compositions of the present invention to adjust their pitch of twist. The twist pitch is preferably adjusted in the range of 40 to 200 μm in the case of liquid crystal compositions for TFT or TN, and preferably adjusted in the range of 6 to 20 μm in the case of liquid crystal compositions for STN. In the case for bistable TN mode, it is preferable to adjust the pitch in the range of 1.5 to 4 μm. Further, two or more kind of optically active compounds may be added for the purpose of adjusting the dependency of pitch on temperature.

Liquid crystal compositions of the present invention can be produced by conventional methods. Generally, a method in which various components are dissolved one another at a high temperature has been adopted.

Further, the liquid crystal compositions of the present invention can be used as ones for guest-host (GH) mode by adding a dichroic dye such as merocyanine type, styryl type, azo type, azomethine type, azoxy type, quinophthalone type, -continued

| Ring structure | Symbol |
| --- | --- |
| (dichlorophenyl, 3,5-Cl) | B(3,5Cl) |
| (2-F, 3-Cl phenyl) | B(2F,3Cl) |
| (2-Cl, 3-F phenyl) | B(2Cl,3F) |
| (3,5-difluorophenyl) | B(3,5F) |
| (3-Cl, 5-F phenyl) | B(3Cl,5F) |
| (cyclohexylene) | H |
| (cyclohexenylene) | Ch |
| (pyran-2-yl) | P(2) |
| (pyran-3-yl) | P(3) |
| (1,3-dioxane-2,5) | D(2,5) |
| (1,3-dioxane-1,6) | D(1,6) |

-continued

| Ring structure | Symbol |
| --- | --- |
| (1,3-dioxane-3,5) | D(3,5) |
| (silacyclohexane) | Si(1) |
| (silacyclohexane) | Si(4) |
| (pyrimidine) | Py |
| (pyridine) | Pr(2) |
| (pyridine) | Pr(3) |
| (2-F-pyridine) | Pr(3F) |

| | Symbol |
| --- | --- |
| Left side terminal group Ra, $R_1$ to $R_4$, $R_6$ | |
| $C_aH_{2a+1}-$ | a— |
| $C_aH_{2a+1}O-$ | aO— |
| $C_aH_{2a+1}OC_bH_{2b}-$ | aOb— |
| $C_aH_{2a+1}OC_bH_{2b}O-$ | aObO— |
| $C_{a-1}H_{2(a-1)+1}C(C_bH_{2b+1})HC_cH_{2c}-$ | a(b)c— |
| $CFH_2C_{a-1}H_{2(a-1)}-$ | Fa— |
| $CF_2HC_{a-1}H_{2(a-1)}-$ | FFa— |
| $CF_3C_{a-1}H_{2(a-1)}-$ | FFFa— |
| $CFH_2C_{a-1}H_{2(a-1)}O-$ | FaO— |
| $CFH_2C_{a-1}H_{2(a-1)}OC_bH_{2b}-$ | FaOb— |
| $C_aH_{2a+1}CFHC_bH_{2b}-$ | a(F)b— |
| $C_aH_{2a+1}CF_2C_bH_{2b}-$ | a(FF)b— |
| $C_aH_{2a+1}SiH_2C_bH_{2b}-$ | a(Si)b— |
| $C_aH_{2a+1}CH=CHC_bH_{2b}-$ | aVb— |
| $C_aH_{2a+1}CH=CHC_bH_{2b}CH=CHC_cH_{2c}-$ | aVbVc— |
| $C_aH_{2a+1}CH=CHC_bH_{2b}OC_cH_{2c}-$ | aVbOc— |
| $C_aH_{2a+1}OC_bH_{2b}CH=CHC_cH_{2c}-$ | aObVc— |
| $CFH_2C_{a-1}H_{2(a-1)}CH=CHC_bH_{2b}-$ | FaVb— |
| $FFC=CHC_aH_{2a}-$ | FFVa— |
| $F(CN)C=CHC_aH_{2a}-$ | FCVa— |
| Bonding group $Z_1$ to $Z_{10}$ | |
| $-(CH_2)_a-$ | a |
| $-CH_2O-$ | $CH_2O$ |
| $-OCH_2-$ | $OCH_2$ |
| $-C_3H_6O-$ | $C_3H_6O$ |
| $-OC_3H_6-$ | $OC_3H_6$ |

| | Symbol |
|---|---|
| —COO— | E |
| —C≡C— | T |
| —CH=CH— | V |
| —CF$_2$O— | CF$_2$O |
| —OCF$_2$— | OCF$_2$ |

Right side terminal group Rb, R$_5$, R$_7$, X$_1$, X$_2$

| | |
|---|---|
| —F | —F |
| —Cl | —CL |
| —CN | —C |
| —CF$_3$ | —CF$_3$ |
| —OCF$_3$ | —OCF$_3$ |
| —OCF$_2$H | —OCF$_2$H |
| —CF$_2$CF$_2$H | —CF$_2$CF$_2$H |
| —CF$_2$CH$_2$CF$_3$ | —CF$_2$CH$_2$CF$_3$ |
| —CF$_2$CFHCF$_3$ | —CF$_2$CFHCF$_3$ |
| —OCH$_2$CF$_2$H | —OCH$_2$CF$_2$H |
| —OCF$_2$CF$_2$H | —OCF$_2$CF$_2$H |
| —OCF$_2$CH$_2$CF$_3$ | —OCF$_2$CH$_2$CF$_3$ |
| —OCF$_2$CFHCF$_3$ | —OCF$_2$CFHCF$_3$ |
| —C$_w$H$_{2w+1}$ | —w |
| —OC$_w$H$_{2w+1}$ | —Ow |
| —C$_w$H$_{2w}$OC$_x$H$_{2x+1}$ | —wOx |
| —OC$_w$H$_{2w}$OC$_x$H$_{2x+1}$ | —OwOx |
| —C$_{w-1}$H$_{2(w-1)}$CFH$_2$ | —wF |
| —C$_w$H$_{2w}$CH=CH$_2$ | —wV |
| —C$_w$H$_{2w}$CH=CHC$_x$H$_{2x+1}$ | —wVx |
| —C$_w$H$_{2w}$CH=CHC$_x$H$_{2x}$CH=CH$_2$ | —wVxV |
| —COOCH$_3$ | —EMe |
| —C$_w$H$_{2w}$CH=CHC$_{x-1}$H$_{2(x-1)}$CFH$_2$ | —wVxF |
| —CH=CF$_2$ | —VFF |
| —C$_w$H$_{2w}$CH=CF$_2$ | —wVFF |
| —C≡C—CN | —TC |

When the hydrogen atom of trans-1,4-cyclohexylene in the following partial structure was replaced by deuterium (heavy hydrogen) at positions Q$_1$, Q$_2$, and Q$_3$, it is designated by symbol H [1D, 2D, 3D], and when replaced at positions Q$_5$, Q$_6$, and Q$_7$, it is designated by symbol H [5D, 6D, 7D]. In other words, the positions where deuterium substituted are indicated by the numeral in the bracket [ ].

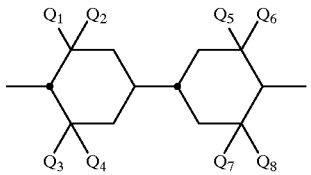

In the Composition Examples and Examples, "%" means % by weight unless otherwise specified. When cis-trans isomers exist in particular compounds, they are trans form.

COMPOSITION EXAMPLE 1

| | |
|---|---|
| 3-HB(3Cl, 5F)B(3F)—F (Compound No. 19) | 7.0% |
| 3-HB 3, 5F)B(3Cl)—F (Compound No. 31) | 3.0% |
| 1V2-BEB(3, 5F)—C | 5.0% |
| 3-HB—C | 20.0% |
| V2-HB—C | 6.0% |
| 1-BTB-3 | 5.0% |
| 2-BTB-1 | 6.0% |
| 1O1-HH-3 | 3.0% |
| 3-HH-4 | 5.0% |
| 3-HHB-1 | 11.0% |
| 3-HHB-3 | 3.0% |
| 3-H2BTB-2 | 4.0% |
| 3-H2BTB-3 | 4.0% |
| 3-H2BTB-4 | 4.0% |
| 3-HB(3F)TB-2 | 6.0% |
| 3-HB(3F)TB-3 | 5.0% |
| 3-HHB—C | 3.0% |

COMPOSITION EXAMPLE 2

| | |
|---|---|
| 3-HB(3, 5F)B(3Cl)—F (Compound No. 31) | 4.0% |
| 5-PyB—F | 4.0% |
| 3-PyB(3F)—F | 4.0% |
| 2-BB—C | 5.0% |
| 4-BB—C | 4.0% |
| 5-BB—C | 5.0% |
| 2-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

COMPOSITION EXAMPLE 3

| | |
|---|---|
| 3-HB(3, 5F)B(3Cl)—F (Compound No. 31) | 4.0% |
| 3-BB(3F)B(3Cl, 5F)B(3F)—F (Compound No. 88) | 5.0% |
| 2O1-BEB(3F)—C | 5.0% |
| 3O1-BEB(3F)—C | 12.0% |
| 5O1-BEB(3F)—C | 4.0% |
| 1V2-BEB(3, 5F)—C | 10.0% |
| 3-HEB-O4 | 4.0% |
| 3-HH—EMe | 2.0% |
| 3-HB-O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(3F)—C | 2.0% |
| 3-HB(3F)EB(3F)—C | 2.0% |
| 3-HBEB(3, 5F)—C | 2.0% |
| 3-HHB—F | 4.0% |
| 3-HHB-O1 | 4.0% |
| 3-HHB-3 | 4.0% |
| 3-HEBEB—F | 2.0% |
| 3-HEBEB-1 | 2.0% |
| 3-HHB(3F)—C | 4.0% |

COMPOSITION EXAMPLE 4

| | |
|---|---|
| 3-HB(3Cl, 5F)B(3F)—F (Compound No. 19) | 2.0% |
| 3-HB(3, 5F)B(3Cl)—F (Compound No. 31) | 3.0% |
| 3-BB(3F)B(3Cl, 5F)B(3F)—F (Compound No. 88) | 5.0% |
| 5-BEB(3F)—C | 5.0% |
| V-HB—C | 11.0% |
| 5-PyB—C | 6.0% |
| 4-BB-3 | 6.0% |

-continued

| | |
|---|---|
| 5-HH—V2V | 4.0% |
| 3-HH-2V | 10.0% |
| 5-HH—V | 7.0% |
| V-HHB-1 | 7.0% |
| V2-HHB-1 | 15.0% |
| 3-HHB-1 | 4.0% |
| 1V2-HBB-2 | 10.0% |
| 3-HHEBH-3 | 5.0% |

COMPOSITION EXAMPLE 5

| | |
|---|---|
| 3-HB(3, 5F)B(3Cl)—F (Compound No. 31) | 5.0% |
| 5-BTB(3F)TB-3 | 10.0% |
| V2-HB-TC | 10.0% |
| 3-HB-TC | 10.0% |
| 3-HB—C | 10.0% |
| 5-HB—C | 7.0% |
| 5-BB—C | 3.0% |
| 2-BTB-1 | 5.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB(3F)TB-2 | 3.0% |

COMPOSITION EXAMPLE 6

| | |
|---|---|
| 3-BB(3F)B(3Cl, 5F)B(3F)—F (Compound No. 88) | 7.0% |
| 1V2-BEB(3, 5F)—C | 6.0% |
| 3-HB—C | 18.0% |
| 2-BTB-1 | 10.0% |
| 5-HH—VFF | 30.0% |
| 1-BHH—VFF | 8.0% |
| 1-BHH-2VFF | 4.0% |
| 3-H2BTB-2 | 5.0% |
| 3-H2BTB-3 | 4.0% |
| 3-H2BTB-4 | 4.0% |
| 3-HHB-1 | 4.0% |

COMPOSITION EXAMPLE 7

| | |
|---|---|
| 3-BB(3F)B(3Cl, 5F)B(3F)—F (Compound No. 88) | 8.0% |
| 7-HB(3F)—F | 5.0% |
| 5-H2B(3F)—F | 5.0% |
| 3-HB-O2 | 10.0% |
| 3-HH-4 | 2.0% |
| 3-HH[5D, 6D, 7D]-4 | 3.0% |
| 2-HHB(3F)—F | 10.0% |
| 3-HHB(3F)—F | 10.0% |
| 5-HH[5D, 6D, 7D]B(3F)—F | 10.0% |
| 3-H2HB(3F)—F | 5.0% |
| 2-HBB(3F)—F | 3.0% |
| 3-HBB(3F)—F | 3.0% |
| 5-HBB(3F)—F | 6.0% |
| 2-H2BB(3F)—F | 5.0% |
| 3-H2BB(3F)—F | 6.0% |
| 3-HHB-O1 | 5.0% |
| 3-HHB-3 | 4.0% |

COMPOSITION EXAMPLE 8

| | |
|---|---|
| 3-HB(3Cl, 5F)B(3F)—F (Compound No. 19) | 2.0% |
| 3-HB(3, 5F)B(3Cl)—F (Compound No. 31) | 3.0% |
| 3-BB(3F)B(3Cl, 5F)B(3F)—F (Compound No. 88) | 4.0% |
| 7-HB(3, 5F)—F | 2.0% |
| 3-H2HB(3, 5F)—F | 12.0% |
| 4-H2HB(3, 5F)—F | 4.0% |
| 3-HHB(3, 5F)—F | 10.0% |
| 4-HHB(3, 5F)—F | 5.0% |
| 3-HBB(3, 5F)—F | 10.0% |
| 3-HHEB(3, 5F)—F | 10.0% |
| 4-HHEB(3, 5F)—F | 3.0% |
| 5-HHEB(3, 5F)—F | 3.0% |
| 2-HBEB(3, 5F)—F | 3.0% |
| 3-HBEB(3, 5F)—F | 5.0% |
| 5-HBEB(3, 5F)—F | 3.0% |
| 3-HD(3, 5)B(3, 5F)—F | 15.0% |
| 3-HBCF$_2$OBP—OCF$_3$ | 4.0% |
| 3-HHBB(3, 5F)—F | 2.0% |

COMPOSITION EXAMPLE 9

| | |
|---|---|
| 3-HB(3, 5F)B(3Cl)—F (Compound No. 31) | 6.0% |
| 3-BB(3F)B(3Cl, 5F)B(3F)—F (Compound No. 88) | 4.0% |
| 3-HB—CL | 10.0% |
| 5-HB—CL | 4.0% |
| 1O1-HH-5 | 3.0% |
| 2-HBB(3F)—F | 8.0% |
| 3-HBB(3F)—F | 8.0% |
| 5-HBB(3F)—F | 14.0% |
| 4-HHB—CL | 8.0% |
| 5-HHB—CL | 8.0% |
| 3-H2HB(3F)—CL | 4.0% |
| 3-HBB(3, 5F)—F | 10.0% |
| 5-H2BB(3, 5F)—F | 9.0% |
| 3-HB(3F)VB-2 | 2.0% |
| 3-H2BTB-2 | 2.0% |

COMPOSITION EXAMPLE 10

| | |
|---|---|
| 3-HB(3Cl, 5F)B(3F)—F (Compound No. 19) | 3.0% |
| 3-HB(3, 5F)B(3Cl)—F (Compound No. 31) | 4.0% |
| 3-BB(3F)B(3Cl, 5F)B(3F)—F (Compound No. 88) | 5.0% |
| 3-H2B(2, 3F)B(2Cl, 3F)-1 (Compound No. 40) | 2.0% |
| 5-HB—F | 10.0% |
| 6-HB—F | 9.0% |
| 2-HHB—OCF$_3$ | 7.0% |
| 3-HHB—OCF$_3$ | 7.0% |
| 4-HHB—OCF$_3$ | 7.0% |
| 3-HH2B—OCF$_3$ | 4.0% |
| 5-HH2B—OCF$_3$ | 4.0% |
| 3-HHB(3, 5F)—OCF$_3$ | 5.0% |
| 3-HBB(3F)—F | 10.0% |
| 5-HBB(3F)—F | 10.0% |
| 3-HH2B(3F)—F | 3.0% |
| 3-HB(3F)BH-3 | 3.0% |
| 5-HBBH-3 | 3.0% |
| 3-HHB(3, 5F)—OCF$_2$H | 4.0% |

COMPOSITION EXAMPLE 11

| | |
|---|---|
| 3-HB(3Cl, 5F)B(3F)—F (Compound No. 19) | 4.0% |
| 3-BB(3F)B(3Cl, 5F)B(3F)—F (Compound No. 88) | 4.0% |
| 5-H4HB(3, 5F)—F | 7.0% |

-continued

| | |
|---|---|
| 5-H4HB—OCF₃ | 15.0% |
| 5-H4HB(3, 5F)—CF₃ | 10.0% |
| 3-HB—CL | 6.0% |
| 5-HB—CL | 4.0% |
| 2-H2BB(3F)—F | 5.0% |
| 3-H2BB(3F)—F | 10.0% |
| 5-HVHB(3, 5F)—F | 5.0% |
| 3-HHB—OCF₃ | 5.0% |
| 3-H2HB—OCF₃ | 5.0% |
| V-HHB(3F)—F | 5.0% |
| 3-HHB(3F)—F | 5.0% |
| 5-HHEB—OCF₃ | 2.0% |
| 3-HBEB(3, 5F)—F | 5.0% |
| 5-HH—V2F | 3.0% |

COMPOSITION EXAMPLE 12

| | |
|---|---|
| 3-H2B(2, 3F)B(2Cl, 3F)-1 (Compound No. 40) | 15.0% |
| 3-HEB-O4 | 24.0% |
| 4-HEB-O2 | 17.0% |
| 5-HEB-O1 | 17.0% |
| 3-HEB-O2 | 15.0% |
| 5-HEB-O2 | 12.0% |

COMPOSITION EXAMPLE 13

| | |
|---|---|
| 3-H2B(2, 3F)B(2Cl, 3F)-1 (Compound No. 40) | 6.0% |
| 3-HH-2 | 5.0% |
| 3-HH-O1 | 4.0% |
| 3-HH-O3 | 5.0% |
| 5-HH-O1 | 4.0% |
| 3-HB(2, 3F)—O2 | 12.0% |
| 5-HB(2, 3F)—O2 | 11.0% |
| 3-HHB(2, 3F)—O2 | 14.0% |
| 5-HHB(2, 3F)—O2 | 15.0% |
| 3-HHB(2, 3F)-2 | 24.0% |

COMPOSITION EXAMPLE 14

| | |
|---|---|
| 3-HB(3Cl, 5F)B(3F)—F (Compound No. 19) | 10.0% |
| 3-HB(3, 5F)B(3Cl)—F (Compound No. 31) | 10.0% |
| 3-BB(3F)B(3Cl, 5F)B(3F)—F (Compound No. 88) | 8.0% |
| 3-H2B(2, 3F)B(2Cl, 3F)-1 (Compound No. 40) | 3.0% |
| 2-HHB(3F)—F | 2.0% |
| 3-HHB(3F)—F | 2.0% |
| 5-HHB(3F)—F | 2.0% |
| 2-HBB(3F)—F | 6.0% |
| 3-HBB(3F)—F | 6.0% |
| 5-HBB(3F)—F | 10.0% |
| 2-H2BB(3F)—F | 9.0% |
| 3-H2BB(3F)—F | 9.0% |
| 3-HBB(3, 5F)—F | 15.0% |
| 5-HBB(3, 5F)—F | 3.0% |
| 1O1-HBBH-4 | 5.0% |

BEST MODE FOR CARRYING OUT THE INVENTION

Now, the present invention will be described in more detail with reference to Examples. In each of the Examples, C indicates crystal, SA: smectic phase A, $S_B$: smectic phase B, $S_X$: smectic phase the structure of which has not yet been defined, N: nematic phase, and Iso: isotropic phase, and unit of all phase transition temperatures is ° C.

EXAMPLE 1

Preparation of 4-propoxycyclohexyl-3-chloro-5-fluoro-4-trifluoromethylbenzene (3O-HB(3Cl,5F)-CF₃ (Compound No. 1))

(First step) Preparation of trans-4-propoxycyclohexyl-3-chloro-5-fluorobenzene

A solution of 3-chloro-5-fluorophenylmagnesium bromide [prepared from 40.2 g (192.0 mmol) of 3-chloro-5-fluorobromobenzene and 4.7 g (192.0 mmol) of magnesium] in 150 ml of tetrahydrofuran (THF) was added by drops to a solution of 25 g (160 mmol) of 4-propoxycyclohexanone in 100 ml of THF at room temperature in 1 hour. After finishing of the dropping, it was stirred at 50° C. for 1 hour. A diluted hydrochloric acid in an amount of 150 ml was added to the reaction solution, stirred for 30 minutes, and then extracted with 250 ml of heptane. The organic layer thus obtained was washed with a diluted aqueous sodium bicarbonate solution thrice and water thrice, and then dried over anhydrous magnesium sulfate. The solvent was distilled off under a reduced pressure to obtain 42.7 g of a yellow oily product.

A mixture of 42.7 g of the yellow oily product, 2.0 g of p-toluenesulfonic acid, and 200 ml of toluene was heated to reflux while taking out the distilled water for 3 hours. After termination of the reaction, the organic layer was washed with water thrice and then dried over anhydrous magnesium sulfate. The solvent was distilled off under a reduced pressure to obtain 37.3 g of a yellow oily product.

The yellow oily product in an amount of 37.3 g, 1.8 g of 5% Pd-C, and 150 ml of ethanol were mixed and subjected to a reduction with hydrogen. After absorption of hydrogen was terminated, the catalyst was removed by filtration. The solvent was distilled off under a reduced pressure and the residue thus obtained was subjected to silica gel column chromatography (eluent: heptane) to obtain 36.8 g of a crude 4-propoxy-cyclohexyl-3-chloro-5-fluorobenzene. (Yield: 84.9%)

This product was used for the subsequent reaction without further purification.

(Second step) Preparation of 4-propoxycyclohexyl-3-chloro-4-iodo-5-fluorobenzene To a solution of 36.8 g (135.9 imol) of the trans-4-propoxycyclohexyl-3-chloro-5-f luorobenzene obtained in the previous step in 150 ml of THF was added by drops 99 ml (1.64 M, THF solution, corresponding to 163.1 mmol) of BuLi while being maintained at a temperature lower than −60° C., and then stirred at the same temperature for 1 hour. Subsequently, a solution of 41.4 g (163.1 mmol) of iodine in 160 ml of THF was added by 1 drops to the reaction mixture while being maintained at a temperature lower than −60° C., and stirred at the same temperature for 1 hour. The reaction solution was poured into 200 ml of a diluted aqueous sodium thiosulfate solution, and then extracted with 150 ml of heptane. The organic layer thus obtained was washed with water thrice and then dried over anhydrous magnesium sulfate. After the solvent was distilled off under a reduced pressure, the residue was subjected to silica gel column chromatography (eluent: heptane) to obtain 53.3 g of a yellow oily product. (Yield: 96.5%)

This product was used for the subsequent reaction without further purification.

(Third step) Preparation of 4-propoxycyclohexyl-3-chloro-5-fluoro-4-trifluoromethylbenzene A mixture of 10.0 g (25.2 mmol) of the trans-4-propoxycyclohexyl-3-chloro-4-iodo-5-fluorobenzene obtained in the previous step, 24.2 g (126.0 mmol) of methyl fluorosulfonyldifluoroacetate, 2.9 g (15.1 mmol) of copper iodide, and 100 ml of dimethyl formamide (DMF) was stirred at 80° C. for 15 hour. The reaction mixture was poured into 300 ml of water and then extracted with 150 ml of heptane. The organic layer thus obtained was washed with a diluted hydrochloric acid thrice, a diluted aqueous sodium bicarbonate solution thrice, and water thrice, and then dried over anhydrous magnesium sulfate. After the solvent was distilled off under a reduced pressure, the residue was subjected to silica gel column chromatography (eluent: heptane) to obtain 7.9 g of a crude trans-4-propoxycyclohexyl-3-chloro-5-fluoro-4-trifluoromethylbenzene. This product was recrystallized from a mixed solvent of ethanol/ethyl acetate to obtain 2.8 g of the subject compound.

(Yield: 32.9%);

$^1$H-NMR (CDCl$_3$, TMS internal standard)

δ (PPm)

0.83–1.95 (m, 14H)

2.49 (tq, 1H)

3.56 (t, 2H)

6.90–7.12 (m, 2H)

By a method similar to that in Example 1, the following compounds can be prepared:

Compound No. 2: 5-HB(3Cl, 5F)-C
Compound No. 3: 3O1-HB(3Cl, 5F)-OCF$_3$
Compound No. 4: 1O5-HB(3, 5Cl)-CFH$_2$
Compound No. 5: 5-HB(2Cl, 3F)-3
Compound No. 6: 4-HB(2F, 3Cl)-O3
Compound No. 7: V-HB(2Cl, 3F)-5
Compound No. 8: 3-H2B(3Cl, 5F)-F
Compound No. 9: 17-H2B(3Cl, 5F)-OCH$_2$CF$_2$H
Compound No. 10: F5-H2B(3Cl, 5F)-CF$_2$H
Compound No. 11: 2-H2B(2Cl, 3F)-O5
Compound No. 12: V2-HVB(2F, 3Cl)-2
Compound No. 13: 3O-H4B(2, 3Cl)-3
Compound No. 14: 3-HB(2Cl, 3F)H-2
Compound No. 15: 3-HB(2, 3Cl)H-5
Compound No. 16: 3-HHHB(3Cl, 5F)-CF$_3$
Compound No. 17: 3O-HHHB(3, 5Cl)-CF$_2$H
Compound No. 18: 5-HHHB(2Cl, 3F)-1

EXAMPLE 2

Preparation of 4'-(trans-4-propylcyclohexyl)-2'-chloro-3,4,6'-trifluorobiphenyl (3-HB(3Cl,5F)B(3F)-F (Compound No. 19))

A mixture of 5.0 g (13.1 mmol) of 4-propylcyclohexyl-3-chloro-5-fluoro-4-iodobenzene [prepared by the same method as in the second step of Example 1 with the exception that 4-propylcyclohexyl-3-chloro-5-fluorobenzene was used in place of the 4-propoxycyclohexyl-3-chloro-5-fluorobenzene used in the second step of Example 1], 3.1 g (19.7 mmol) of dihydroxy (3,4-difluorophenyl)borane [prepared by reacting a Grignard reagent, which was prepared in turn from 3,4-difluorobromobenzene, with trimethoxyborane, and then hydrolyzing with hydrochloric acid], 3.6 g (26.3 mmol) of potassium carbonate, 0.5 g of 5% Pd-C, and 50 ml of mixed solvent of toluene/ethanol/water (1/1/1) was heated to reflux for 32 hours. After the catalyst was removed by filtration, the mixture was extracted with 100 ml of toluene. The organic layer thus obtained was washed with water thrice and then dried over anhydrous magnesium sulfate. The solvent was distilled off under a reduce pressure and the residue thus obtained was subjected to silica gel column chromatography (eluent: heptane) to obtain 4.4 g of a crude 4'-(trans-4-propyl-cyclohexyl)-2'-chloro-3,4,6'-trifluorobiphenyl. This product was recrystallized from a mixed solvent of ethanol/ethyl acetate to obtain 0.9 g of the subject compound. (Yield: 18.3%)

Phase transition temperatures of this compound were as follows:

C 50.6~51.7 Iso $^1$H—NMR (CDCl$_3$, TMS internal standard)

δ (ppm)

0.83–1.96 (m, 16H)

2.48 (t, 1H)

6.86–7.38 (m, 5H)

Examples in which the compounds of the present invention are used as component of liquid crystal compositions are shown below. In each of the use examples, NI indicates phase transition temperature of nematic phase to isotropic phase (°C.), Δ∈: dielectric anisotropy value, Δn: optical anisotropy value, η: viscosity (mPa.s), Vth: threshold voltage (V), and VHR: voltage holding ratio (%).

In this connection, η shows the value determined at 20° C.; each of Δ∈, Δn, Vth, and pitch length of twist shows the value determined at 25° C.; and VHR shows values determined at 250° C., 80° C., and 100° C., respectively, from left side in turn.

EXAMPLE 3 (USE EXAMPLE 1)

Liquid crystal composition (A) comprising the following cyanophenylcyclohexane type liquid crystalline compounds in the amount shown below

| 3-HB—C | 24% |
|---|---|
| 5-HB—C | 36% |
| 7-HB—C | 25% |
| 5-HBB—C | 15% | had the following physical properties:

NI: 71.7, Δ∈: 11.0, Δn: 0.137, η: 26.7, Vth: 1.78

Physical properties of liquid crystal composition (B) comprising 85% of the liquid crystal composition (A) and 15% of the 4'-(trans-4-propylcyclohexyl)-2'-chloro-3,4,6'-trifluorobipehnyl (Compound No. 19) obtained in Example 2 were as follows:

NI: 55.1, Δ∈: 11.1, Δn: 0.125, η: 35.5, Vth: 1.44

While this liquid crystal composition (B) was left in a freezer at −20° C., development of smectic phase or separation of crystals was not observed over 60 days.

By a method similar to that in Example 2, the following compounds can be prepared. In the following, physical properties shown therein are values determined according to those in Example 3.

Compound No. 20: 3-BB(3Cl, 5F)-OCF$_2$CF$_2$H
Compound No. 21: 7-B(3F) B (3Cl, 5F)-OCF$_2$CFHCF$_3$
Compound No. 22: F3-B(3Cl, 5F)B(3Cl, 5F)-CL
Compound No. 23: 2-BB(2Cl, 3F)-O2
Compound No. 24: 5-B(3Cl)B(2F, 3Cl)-1O5
Compound No. 25: 2-B(2, 3F)B(2Cl, 3F)-O5
Compound No. 26: FF3-B(3F)2B(2Cl, 3F)-C
Compound No. 27: 8-B(3,5F)2B(3,5Cl)-CF$_3$
Compound No. 28: 5O-B(2, 3F)2B(2, 3Cl)-1
Compound No. 29: 3-B(3, 5F)CF$_2$OB(3Cl)-F
Compound No. 30: 5-B(2, 3Cl)4B(2, 3Cl)-F
Compound No. 31: 3-HB(3, 5F)B(3Cl)-F NI: 59.5, Δ∈: 11.0, Δn: 0.129, η: 34.4, Vth: 1.45

Compound No. 32: 5-HB(2, 3F)B(3Cl, 5F)-OCF$_3$

Compound No. 33: 7-H[5D,6D,7D]2B(3Cl)B(3,5F)-OCF$_3$
Compound No. 34: F2V-HB (2, 3Cl)B(3, 5F)-F
Compound No. 35: 4-HB(3Cl)B(2, 3F)-O2
Compound No. 36: 5-HB(2Cl, 3F)B(2Cl, 3F)-3
Compound No. 37: 2-H2B(3, 5F)B(3Cl)-F
Compound No. 38: 5-H2B(3Cl, 5F)B(3Cl, 5F)-OCH$_2$CF$_2$H
Compound No. 39: 7-H4B(3Cl)B(3, 5F)-F
Compound No. 40: 3-H2B(2, 3F)B(2Cl, 3F)-1
  NI: 61.3, Δ∈: 9.60, Δn: 0.131, η: 36.1, Vth: 1.66
Compound No. 41: 3-H2B(2F, 3Cl)B(2, 3F)-O3
Compound No. 42: V2V-H4B(3Cl)B(2, 3Cl)-3
Compound No. 43: 6-HB(3, 5F)2B(3Cl)-F
Compound No. 44: 2-BBB(3Cl, 5F)-CF$_3$
Compound No. 45: 5-BB(3Cl, 5F)B(3F)-OCF$_3$
Compound No. 46: 3-B(3, 5F)BB(3C 1, 5F)-F
Compound No. 47: 8O-B(3F)B(3, 5Cl)B(3F)-CF$_3$
Compound No. 48: 4O-B(3, 5Cl)B(3Cl)B(3, 5F)-OCF$_2$CFHCF$_3$
Compound No. 49: F2V-BBB(3Cl, 5F)-V2F
Compound No. 50: 2(1)1-BB(2Cl, 3F)B(3Cl)-7
Compound No. 51: 5-B(2, 3F)B(3Cl)B-2
Compound No. 52: 4-BB(2F, 3Cl)B(2Cl, 3F)-O3
Compound No. 53: 16-B(2F, 3Cl)BB(2, 3F)-1
Compound No. 54: 3O-B(2, 3F)B(2, 3Cl)B(2, 3F)-O2
Compound No. 55: 3-B2B(3, 5Cl)B(3F)-F
Compound No. 56: 5-B 2B(3, 5F)B(3Cl)-F
Compound No. 57: 11O-B(3, 5F)2B(3Cl)B(3, 5F)-F
Compound No. 58: 8O8-B(3Cl)2B(3, 5F)B(3, 5F)-C
Compound No. 59: 3-B(3Cl)4B(3, 5F)B-OCF$_3$
Compound No. 60: 4-B(3F)CF$_2$OB(3Cl)B(3F)-OCF$_3$
Compound No. 61: 3-B2B(3F)B(2Cl, 3F)-2
Compound No. 62: 6-B2B(2, 3Cl)B(2, 3Cl)-O2
Compound No. 63: 3O-B(2, 3F)2B(2Cl)B(2, 3F)-O2
Compound No. 64: 2O1-BCF$_2$OB(3Cl)B(2, 3F)-O3
Compound No. 65: 5-BB(3Cl)2B(3, 5F)-C
Compound No. 66: 5-B(3, 5F)B(3Cl)2B(3Cl)-F
Compound No. 67: 5-BB(2, 3Cl)4B(3F)-CL
Compound No. 68: 3-HHB(3, 5F)B(3Cl)-OCH$_2$CF$_2$H
Compound No. 69: 7-HHB(3F)B(3Cl)-C
Compound No. 70: 14-HHB(3Cl, 5F)B(3, 5F)-F
Compound No. 71: 3O-HHB(2Cl, 3F)B(3F)-O2
Compound No. 72: 5-HH2B(3Cl, 5F)B(3F)-OCF$_3$
Compound No. 73: 4-HH2B(3, 5Cl)B(3, 5F)-CFH$_2$
Compound No. 74: 5-HH2B(2, 3Cl)B(2, 3F)-1O1
Compound No. 75: 3-HBB(3Cl)B(3F)-OCF$_2$H
Compound No. 76: 5-HB(3Cl)BB(3F)-OCF$_2$H
Compound No. 77: 1O-HB(3Cl, 5F)B(3, 5Cl)B-OCF$_3$
Compound No. 78: 3O1-HB(3, 5F)B(3Cl, 5F)B(3F)-CF$_3$
Compound No. 79: 5-HBB(2Cl)B(2, 3F)-O2
Compound No. 80: FFF3-HB(2, 3F)B(3Cl)B(2, 3F)-2
Compound No. 81: FFV-HB(2F, 3Cl)B(2Cl)B(2Cl, 3F)-3
Compound No. 82: 2Si2-H2B(3Cl, 5F)B(3F)B(3F)-CF$_2$CH$_2$CF$_3$
Compound No. 83: 3-H2BB(2, 3Cl)B(2, 3F)-O2
Compound No. 84: 5-H4B(3Cl, 5F)B(3F)B(3, 5F)-CFH$_2$
Compound No. 85: 4O-HB(3F)2B(3Cl, 5F)B(3, 5F)-CL
Compound No. 86: 3-BBB(3Cl, 5F)B(3F)-CF$_2$H
Compound No. 87: 7-BB(3Cl)B(3, 5Cl)B-CF$_3$
Compound No. 88: 3-BB(3F)B(3Cl, 5F)B(3F)-F
  NI: 74.4, Δ∈: 12.2, Δn: 0.152, η: 40.6, Vth: 1.56
Compound No. 89: 2O-BB(3Cl, 5F)B(3F)B(3F)-OCF$_3$
Compound No. 90: 1O1O-B(3Cl)B(3, 5F)B(3Cl, 5F)B(3F)-F
Compound No. 91: 1O-BBB(3Cl, 5F)B(5F)-2
Compound No. 92: 3-BB(2Cl)B(2Cl, 3F)B(2, 3F)-5
Compound No. 93: 3O-B(2, 3F)B(2Cl)B(3Cl)B(2, 3F)-O2
Compound No. 94: 2-B2B(3F)B(3Cl, 5F)B-C
Compound No. 95: 5-B2B(3Cl)B(3Cl, 5F)B(3F)-CF$_2$CF$_2$H
Compound No. 96: 4-B(3F)B(3F)2B(3Cl, 5F)B(3F)-CF$_3$
Compound No. 97: 3O-B(2, 3F)B2B(3F)B(2Cl, 3F)-1
Compound No. 98: 5-BB(3Cl, 5F)B(3F)2B(3, 5F)-C
Compound No. 99: 3-HBB(2Cl, 3F)H-5
Compound No. 100: 4-HBB(2, 3Cl)H-5
Compound No. 101: 2-HB(2Cl, 3F)B(2Cl, 3F)H-5
Compound No. 102: V-HB(2, 3F)B(2Cl)H-V1

EXAMPLE 4

Preparation of 2'-chloro-2,3,3'-trifluoro-4'-methyl-4-((trans-4-(trans-4-butylcyclohexyl)cyclohexyl)methoxy)biphenyl (4-HHCH$_2$OB(2,3F)B(2Cl,3F)-1 (compound No. 103))

(First step) Preparation of 2'-chloro-2,3,3'-trifluoro-4-hydroxy-4'-methylbiphenyl To a solution of 40.0 g (276.7 mmol) of 3-chloro-2-fluorotoluene and 200 ml of THF was added by drops 287 ml (1.06M, cyclohexane solution, corresponding to 304.3 mmol) of sec-BuLi while being maintained at a temperature lower than −60° C. and stirred at the same temperature for 1 hour. Subsequently, 830 ml (0.5M, THF solution, 415.0 mmol) of zinc chloride was added by drops to the reaction mixture while being maintained at a temperature lower than −60° C. and stirred at the same temperature for 1 hour. To the reaction solution were added 55.3 g (184.4 mmol) of 2,3-difluoro-4-methoxymethoxy-iodobenzene and 6.4 g (5.5 mmol) of tetrakistriphenylphosphine palladium and then heated to reflux for 7 hours. After termination of the reaction, 300 ml of water was added thereto and extracted with 200 ml of heptane. The organic layer thus obtained was washed with water thrice and then dried over anhydrous magnesium sulfate. The solvent was distilled off under a reduced pressure to obtain 57.2 g of a brown oily product.

Subsequently, the residue was subjected to silica gel column chromatography (eluent: heptane) to obtain 12.4 of a colorless oily product.

The colorless oily product in an amount of 12.4 g, 10 ml of a concentrated hydrochloric acid, and 50 ml of methanol were mixed and heated to reflux for 3 hours. To the reaction mixture was added 50 ml of water and extracted with 100 ml of diethyl ether. The organic layer thus obtained was washed with a diluted aqueous sodium bicarbonate solution once and water thrice, and then dried over anhydrous magnesium sulfate. The solvent was distilled off under a reduced pressure to obtain 9.8 g of a crude 2'-chloro-2,3,3'-trifluoro-4-hydroxy-4'-methylbiphenyl. (Yield: 50.3%)

This product was used for the subsequent reaction without further purification.

(Second step) Preparation of 2'-chloro-2,3,3'-trifluoro-4'-methyl-4-((trans-4-(trans-4-butylcyclohexyl)cyclohexyl)methoxy)biphenyl In a mixture of 0.7 g (60% oiliness, corresponding to 17.6 mmol) of sodium hydride and 5 ml of DMF was added by drops a solution of 4.0 g (14.7 mmol) of the 2'-chloro-2,3,3'-trifluoro-4-hydroxy-4'-methylbiphenyl in 20 ml of DMF at room temperature and stirred at the same temperature for 1 hour. Subsequently, a solution of 8.0 g (22.0 mmol) of trans-4-(trans-4-butylcyclohexyl)-1-iodomethylcyclohexane in 20 ml of DMF was added by drops to the reaction solution at room temperature, stirred at the same temperature for 1 hour, and then refluxed for 3 hours. After termination of the reaction, the reaction solution was poured into 50 ml of a diluted hydrochloric acid and extracted with 150 ml of toluene. The organic layer thus obtained was washed with a diluted aqueous sodium hydroxide solution thrice and water thrice, and then dried over anhydrous magnesium sulfate. The solvent was distilled off under a reduced pressure and the residue was subjected to silica gel column chromatography (eluent: heptane/toluene= 7/3) to obtain 4.6 g of a crude 2'-chloro-2,3,3'-trifluoro-4'-methyl-4-((trans-4-(trans-4-butylcyclohexyl)cyclohexyl) methoxy)biphenyl. This product was recrystallized from a mixed solvent of ethanol/ethyl acetate to obtain 3.3 g of the subject compound. (Yield: 44.6%)

$^1$H—NMR (CDCl$_3$, TMS internal standard)

δ (ppm)

0.79–2.03 (m, 29H)

2.35 (d, 3H)

3.85 (d, 2H)

6.87–7.26 (m, 4H)

By a method similar to that of Example 4, the following compounds can be prepared:

Compound No. 104: 3-HCH$_2$OB(3Cl, 5F)-CF$_3$
Compound No. 105: 3O-HCH$_2$OB(3Cl, 5F)-OCF$_3$
Compound No. 106: V-HCH$_2$OB(3Cl, 5F)-CF$_2$H
Compound No. 107: FFV-HCH$_2$OB(3Cl, 5F)-OCF$_2$H
Compound No. 108: 5-HCH$_2$OB(3Cl, 5F)-1
Compound No. 109: 3-B(3F) CH$_2$OB(3Cl, 5F)-F
Compound No. 110: 5-B(3Cl, 5F)OCH$_2$B-F
Compound No. 111: 7-B(3, 5F)CH$_2$OB(3Cl, 5F)-CL
Compound No. 112: 3-B(3F)CH$_2$OB(2Cl, 3F)-O2
Compound No. 113: 7O-B(2Cl, 3F)CH$_2$OB(3, 5F)-O1
Compound No. 114: 2-D(3, 5)CH$_2$OB(3Cl, 5F)-OCF$_2$CFHCF$_3$
Compound No. 115: 4-PyCH$_2$OB(3Cl, 5F)-OCF$_2$CF$_2$H
Compound No. 116: 6-Pr(3)CH$_2$OB(3Cl, 5F)-CF$_3$
Compound No. 117: 3-HCH$_2$OHB(3Cl, 5F)-F
Compound No. 118: 5-HCH$_2$OHB(2Cl, 3F)-O2
Compound No. 119: 2-HCH$_2$OB(3F)B(3Cl, 5F)-CL
Compound No. 120: 4-HCH$_2$OB(3Cl, 5F)B(3F)-OCF$_3$
Compound No. 121: 6-HOCH$_2$B(3, 5Cl)B(3Cl, 5F)-CF$_3$
Compound No. 122: 3-HCH$_2$OB(2, 3F)B(3Cl)-2
Compound No. 123: 3-HCH$_2$OB(2Cl, 3F)B(2Cl, 3F)-O2
Compound No. 124: 2-B(3F)CH$_2$OB(3Cl, 5F)B(3F)-F
Compound No. 125: 3-B(3Cl, 5F)CH$_2$OB(3, 5Cl)B-OCF$_2$H
Compound No. 126: 4-B(3F)CH$_2$OB(3Cl, 5F)B(3, 5F)-CF$_2$H
Compound No. 127: F3-B(3F)CH$_2$OB(2Cl, 3F)B(2Cl)-4F
Compound No. 128: 5-B(2, 3Cl)CH$_2$OB(2, 3F)B-3
Compound No. 129: 2O-B(2, 3Cl)CH$_2$OB(2, 3Cl)B(2, 3Cl)-O1
Compound No. 130: 17O-D(3, 5)CH$_2$OB(3Cl, 5F)B(3F)-CL
Compound No. 131: 3-D(2, 5)CH$_2$OB(2, 3F)B(2Cl, 3F)-1
Compound No. 132: 5-PyCH$_2$OB(3Cl)B(3, 5F)-C
Compound No. 133: 7-Pr(3)CH$_2$OB(3Cl, 5F)B(3, 5F)-F
Compound No. 134: 3-HHCH$_2$OB(3Cl, 5F)-OCH$_2$CF$_2$H
Compound No. 135: 5-HHCH$_2$OB(2F, 3Cl)-3
Compound No. 136: 4-D(3, 5)HCH$_2$OB(3Cl, 5F)-CF$_2$CF$_2$H
Compound No. 137: 3-HB(3Cl, 5F)CH$_2$OB(3F)-CL
Compound No. 138: 3-HB(2Cl)CH$_2$OB(2, 3F)-O2
Compound No. 139: 4-BB(3, 5F)CH$_2$OB(3Cl)-F
Compound No. 140: 5-B(3Cl, 5F)B(3Cl, 5F)CH$_2$OB(3F)-OCF$_3$
Compound No. 141: 5-BB(2, 3Cl)CH$_2$OB(2, 3F)-5
Compound No. 142: 4-B(2Cl, 3F)B(3F)CH$_2$OB(2, 3F)-1O3
Compound No. 143: 2O1-D(3, 5)B(3Cl, 5F)CH$_2$OB-CL
Compound No. 144: 6-PyB(3, 5F)CH$_2$OB(3Cl)-F
Compound No. 145: 4O-Pr(3)B(3, 5F)CH$_2$OB(3, 5F)-OCF$_3$
Compound No. 146: 2-HHHCH$_2$OB(3Cl, 5F)-C
Compound No. 147: 1V2-HHHCH$_2$OB(2Cl, 3F)-3
Compound No. 148: 5-HHCH$_2$OHHB(3Cl, 5F)-CF$_3$
Compound No. 149: 4-HCH$_2$OHHB(3, 5Cl)-OCF$_3$
Compound No. 150: 6-HHB(3Cl, 5F)CH$_2$OB(3Cl)-CL
Compound No. 151: 3-HHCH$_2$OB(2, 3F)B(3, 5Cl)-3
Compound No. 152: 5O-HCH$_2$OHB(3Cl, 5F)B(3Cl)-F
Compound No. 153: 3-HB(3Cl)B(3, 5F)CH$_2$OB(3Cl)-F
Compound No. 154: 5-HBB(2Cl, 3F)CH$_2$OB(2, 3F)-3
Compound No. 155: 4O-HB(3F)CH$_2$OB(3Cl, 5F)B(3Cl)-CF$_3$
Compound No. 156: 2-HCH$_2$OB(2, 3F)BB(2Cl, 3F)-1
Compound No. 157: 2O2-BB(3Cl,5F)B(3F)CH$_2$OB(3,5F)-OCF$_3$
Compound No. 158: 5-BBB(2Cl, 3F)CH$_2$OB(2, 3F)-O2
Compound No. 159: FF6-B(3F)B(3F)CH$_2$OB(3Cl)B-CF$_3$
Compound No. 160: 3-BB(3Cl)CH$_2$OB(2, 3F)B(2, 3F)-O3
Compound No. 161: 4-B(3F)CH$_2$OB(3, 5Cl)B(3Cl, 5F)B(3F)-CFH$_2$
Compound No. 162: 3-D(3, 5)D(3, 5)HCH$_2$OB(3Cl, 5F)-CF$_3$
Compound No. 163: 3-HD(3, 5)CH$_2$OB(3Cl, 5F)B(3F)-OCF$_3$
Compound No. 164: 4-HPyCH$_2$OB(3Cl, 5F)B(3Cl)-F
Compound No. 165: 4-HPrCH$_2$OB(3, 5Cl)B(3F)-CF$_2$H
Compound No. 166: 5-B(3F)CH$_2$OPyB(3Cl, 5F)B(3, 5F)-C

EXAMPLE 5

Preparation of 3,5-difluoro-4-cyanophenyl2-chloro-6-fluoro-4-pentyloxymethylbenzoate (5O1-B(3Cl,5F)EB(3,5F)-C (Compound No. 167))

First, 3.0 g (10.9 mmol) of 2-chloro-6-fluoro-4-pentyloxymethylbenzoic acid [prepared by reacting 3-chloro-5-fluoropentyloxymethylbenzene with n-BuLi and carbon dioxide], 1.9 g (16.4 imol) of thionyl chloride, 0.1 ml of pyridine, and 6 ml of toluene were mixed and reacted at 60° C. for 3 hours. Excess of the thionyl chloride and the toluene were distilled off under a reduced pressure to obtain 3.2 g of a yellow oily product.

Subsequently, 2.0 g (13.1 mmol) of 3,5-difluoro-4-cyanophenol, 1.3 g of pyridine, and 5 ml of toluene were dissolved. To this solution was added by drops a solution of the yellow oily product obtained in the previous step in 3 ml of toluene at room temperature. After finishing of the dropping, it was reacted at 50° C. for 2 hours. After termination of the reaction, 10 ml of water was added to the reaction mixture and then extracted with 30 ml of toluene. The organic layer thus obtained was washed with a diluted hydrochloric acid thrice, a diluted aqueous sodium hydroxide solution thrice, and water thrice, and then dried over anhydrous magnesium sulfate. The solvent was distilled off under a reduced pressure and the residue was subjected to silica gel column chromatography (eluent: toluene) to obtain 4.0 g of a crude 3,5-difluoro-4-cyanophenyl2-chloro-6-fluoro-4-pentyloxymethylbenzoate. This product was recrystallized from a mixed solvent of heptane/ether to obtain 1.8 g of the subject compound. (Yield: 40.0%)

$^1$H-NMR (CDCl$_3$, TMS internal standard)

δ (ppm)

0.97 (t, 3H)

1.30–0.78 (m, 6H)

3.53 (t, 2H)

4.60 (s, 2H)

5 6.93–7.36 (m, 4H)

By a method similar to that of Example 5, the following compounds can be prepared:

Compound No. 168: 5-HEB(3Cl, 5F)-OCF$_3$
Compound No. 169: 3O-HEB(2F, 3Cl)-3

Compound No. 170: 5-B(3CL, 5F)EB(3F)-CF$_3$
Compound No. 171: 4-D(3, 5)EB(3Cl, 5F)-CF$_3$
Compound No. 172: 6-Si (1)EB(3, 5Cl)-OCF$_2$CFHCF$_3$
Compound No. 173: 1V2-PyEB(3Cl, 5F)-C
Compound No. 174: F4-Pr(3)EB(2Cl, 3F)-O2
Compound No. 175: 2-HB(3F)EB(3Cl, 5F)-F
Compound No. 176: 3-HB(3Cl, 5F)EB(3F)-OCF$_3$
Compound No. 177: V-HB(3Cl, 5F)EB(3, 5F)-CN
Compound No. 178: 2V-HB(3Cl)EB(2, 3F)-O3
Compound No. 179: 5-Si (1)B(3Cl)EB(3, 5F)-CF$_3$
Compound No. 180: 3-D(2, 5)B(3F)EB(2F, 3Cl)-O2
Compound No. 181: 5O2-HEB(3Cl, 5F)B(3F)-CF$_2$H
Compound No. 182: 3-HEB(3, 5Cl)B(3, 5F)-C
Compound No. 183: 5-HEB(3Cl)B(2Cl, 3F)-1
Compound No. 184: 5-HEB(2F, 3Cl)B(2, 3F)-O2
Compound No. 185: 4-Si (4)EB(3Cl, 5F)B(3F)-OCF$_2$CH$_2$CF$_3$
Compound No. 186: 4-D(3, 5)EB(3, 5F)B(3Cl, 5F)-CF$_3$
Compound No. 187: 2-BB(3F)EB(3, 5Cl)-CF$_3$
Compound No. 188: 1O5-B(3Cl)B(3, 5F)EB(3Cl)-OCH$_2$CF$_2$H
Compound No. 189: 7-B(3F)B(3, 5F)EB(3Cl, 5F)-C
Compound No. 190; FFF3-BB(2Cl)EB(2, 3F)-O2
Compound No. 191: 5O-B(2, 3 F)B(3Cl)EB(2Cl, 3F)-O2
Compound No. 192: 2-B(3, 5F)PyEB(3Cl, 5F)-CL
Compound No. 193: 3-Pr(3)B(3Cl, 5F)EB(3F)-CF$_2$H
Compound No. 194: 5-B(3, 5F)Pr(2)EB(2Cl)-3
Compound No. 195: 4-B(3Cl)EB(3, 5F)B(3F)-OCF$_2$CF$_2$H
Compound No. 196: F5-B(3F)EB(3, 5Cl)B(3Cl)-CL
Compound No. 197: 6-BEB(2F, 3Cl)B(2, 3F)-O2
Compound No. 198: 2O3-B(3Cl, 5F,) EPyB(3Cl, 5F)-CF$_3$
Compound No. 199: 1-Pr(3)EB(3Cl, 5F)B(3F)-C
Compound No. 200: 4O-B(3F)EB(3Cl, 5F)EB(3F)-CL
Compound No. 201: 12O-HHB(3Cl, 5F)EB(3F)-OCF$_2$H
Compound No. 202: 4-HSi(4)EB(2F, 3Cl)B(3, 5F)-O2
Compound No. 203: 3-HHEB(3Cl, 5F)B(3, 5F)-F
Compound No. 204: 4-Si(4)HEB(3, 5F)B(3Cl)-CL
Compound No. 205: 5-HD(3, 5)EB(3Cl, 5F)B(3Cl, 5F)-CF$_3$
Compound No. 206: 8O-HEHB(3Cl, 5F)B(3F)-CF$_2$H
Compound No. 207: 2O3-HB(3Cl, 5F)B(3F)EB(3, 5F)-C
Compound No. 208: FFV-HB(3F)EB(3Cl, 5F)B(3F)-CFH$_2$
Compound No. 209: FF3-HEB(3, 5Cl)B(3F)B(3Cl, 5F)-OCF$_2$CFHCF$_3$
Compound No. 210: 3-BB(3F)B(3Cl, 5F) EB(3F)-CL
Compound No. 211: 7-B(3Cl)B(3F)EB(3Cl, 5F)B(3, 5F)-F
Compound No. 212: 9-BEB(2, 3F)B(2Cl, 3F)B-3
Compound No. 213: 5-PyEB(3F)B(3, 5Cl)B(3F)-OCF$_3$
Compound No. 214: 4-B(3F)B(3Cl, 5F)Pr(3)EB(3Cl, 5F)-CF$_3$

EXAMPLE 6

Preparation of trans-2-(2-(2,6-dichloro-3',4',5'-triflurobiphenyl-4-yl)ethyl)-5-propyl-1,3-dioxane (3-D(3,5)2B(3,5Cl)B(3,5F)-F (Compound No. 215))

(First step) Preparation of trans-2-(2-(3,5-dichlorophenyl)-ethyl)-5-propyl-1,3-dioxane A solution comprising 18.3 g (155.1 mmol) of 2-propyl-1,3-propanediol, 30.0 g (147.7 mmol) of 3-(3,5-dichlorophenyl)-propionaldehyde, 1.5 g of p-toluenesulfonic acid, and 300 ml of toluene was heated to reflux while taking out the distilled water for 3 hours. After termination of the reaction, the organic layer was washed with a diluted aqueous sodium bicarbonate solution once and water thrice, and then dried over anhydrous magnesium sulfate. The solvent was distilled off under a reduced pressure and the residue was subjected to silica gel column chromatography (eluent: toluene) to obtain 32.3 g of a crude trans-2-(2-(3,5-dichlorophenyl)ethyl)-5-propyl-1,3-dioxane. (Yield: 72.1%)

This product was used for the subsequent reaction without further purification.

(Second step) Preparation of trans-2-(2-(3,5-dichloro-4-iodophenyl)ethyl)-5-propyl-1,3-dioxane Crude trans-2-(2-(3,5-dichloro-4-iodophenyl)ethyl)-5-propyl-1,3-dioxane in an amount of 39.9 g was obtained by the same method as in the second step of Example 1 with the exception that 32.3 g (106.5 mmol) of the trans-2-(2-(3,5-dichlorophenyl)-ethyl)-5-propyl-1,3-dioxane obtained in the previous step was used in place of the 4-propoxycyclohexyl-3-chloro-5-fluorobenzene used in the second step of Example 1. (Yield: 87.3%)

This product was used for the subsequent reaction without further purification.

(Third step) Preparation of trans-2-(2-(2,6-dichloro-3',4',5'-trifluorobiphenyl-4-yl)ethyl)-5-propyl-1,3-dioxane Crude trans-2-(2-(2,6-dichloro-3',4',5'-triflurobiphenyl-4-yl)ethyl)-5-propyl-1,3-dioxane in amount of 3.9 g was obtained by the same method as Example 2 with the exception that 5 g (11.7 mmol) of the trans-2-(2-(3,5-dichloro-4-iodophenyl)ethyl)-5-propyl-1,3-dioxane obtained in the previous step was used in place of the trans-4-propylcyclohexyl-3-chloro-5-fluoro-4-iodobenzene used in Example 2, and that 2.7 g (15.1 mmol) of dihydroxy(3,4,5-trifluorophenyl)borane was used in place of dihydroxy(3,4-difluorophenyl)borane.

This product was recrystallized from a mixed solvent of ethanol/ethyl acetate to obtain 1.1 g of the subject compound.

(Yield: 22.0%)

$^1$H-NMR (CDCl$_3$, TMS internal standard)

δ (ppm)

0.82–1.29 (m, 7H)

1.82–2.23 (m, 3H)

2.75 (dd, 2H)

3.31 (dd, 2H)

4.10 (dd, 2H)

4.46 (dd, 1H)

6.78–6.92 (m, 2H)

0.74 (d, 2H)

By a method similar to that in Example 6, the following compounds can be prepared:

Compound No. 216: 3-D(3, 5)B(3Cl, 5F)-CF$_3$
Compound No. 217: 5-D(3, 5)B(2Cl, 3F)-1
Compound No. 218: 4O-D(3, 5)2B(3Cl, 5F)-C
Compound No. 219: 2O1-D(2, 5)4B(3Cl, 5F)-F
Compound No. 220: F5-D(3, 5)HB(3Cl, 5F)-OCF$_2$H
Compound No. 221: F3V-HD(3, 5)B(3Cl, 5F)-CF$_2$H
Compound No. 222: 3O-D(3, 5)2HB(3, 5Cl)-CL
Compound No. 223: 7-D(3, 5)H2B(3Cl, 5F)-CF$_2$CH$_2$CF$_3$
Compound No. 224: 3(F)2-H4D(2, 5)B(2F, 3Cl)-O2
Compound No. 225: 5-HD(3, 5)2B(3, 5Cl)-C
Compound No. 226: 4-D(3, 5)B(3Cl, 5F)B(3, 5F)-OCF$_3$
Compound No. 227: 5-D(2, 5)B(2, 3Cl)B(3, 5F)-O1
Compound No. 228: 2-D(3, 5)2B(3Cl)B(3, 5F)-CL
Compound No. 229: 10-D(3, 5)B(3Cl, 5F)2(3Cl, 5F)-OCH$_2$CF$_2$H
Compound No. 230: 2-B(2Cl, 3F)D(2, 5)B(2F, 3Cl)-3
Compound No. 231: 11-D(3, 5)HHB(3Cl, 5F)-C
Compound No. 232: 5-HHD(2, 5)B(2Cl, 3F)-O2
Compound No. 233: 7-D(3, 5)HB(3Cl, 5F)B(3F)-CFH$_2$
Compound No. 234: 2O-HD(3, 5)B(3, 5Cl)B(3Cl)-CL
Compound No. 235: 4-D(3, 5)B(3F)B(3Cl, 5F)B(3, 5F)-OCF$_3$ Compound No. 236: 5-B(2, 3F)D(2, 5)B(2, 3F)B(3Cl)-3
Compound No. 237: 13-D(3, 5)HH$_2$B(3Cl, 5F)-C
Compound No. 238: 1O1-D(3, 5)2HHB(3, 5Cl)-CF$_3$
Compound No. 239: F-6-HD(3, 5)2B(3Cl, 5F)B(3F)-OCF$_2$H
Compound No. 240: 3-D(2, 5)B(2, 3F)B 2B(2F, 3Cl)-2

EXAMPLE 7

Preparation of 2-(2-chloro-3',5',6-trifluoro-4'-trifluoromethoxybiphenyl-4-yl)-5-pentylpyrimidine (5-PyB(3Cl,5F)B(3,5F)-OCF$_3$ (Compound No. 241)

(First step) Preparation of 2-(3-chloro-5-fluorophenyl)-5-pentylpyrimidine

A solution of 3-chloro-5-fluorophenylmagnesium bromide [prepared from 22.7 g (108.3 mmol) of 3-chloro-5-fluoro-bromobenzene and 2.7 g (111.0 mmol) of magnesium, and 100 ml of diethyl ether] in diethyl ether was added by drops to a mixture of 10 g (54.1 mmol) of 2-chloro-5-pentylpyrimidine, 0.4 g (0.5 mmol) of dichloro[1,1'-bis(diphenylphosphino) ferrrocene]palladium, and 300 ml of diethyl ether while being maintained at a temperature lower than −60° C., stirred at the same temperature for 1 hour, and then stirred at 10° C. for 10 hours. A diluted hydrochloric acid in an amount of 300 ml was added to the reaction mixture and extracted with 250 ml of heptane. The organic layer thus obtained was washed with a diluted aqueous sodium bicarbonate solution thrice and water thrice, and then dried over anhydrous magnesium sulfate. The solvent was distilled off under a reduced pressure and the residue was subjected to silica gel column chromatography (eluent: heptane/toluene=1/1) to obtain 11.0 g of a crude 2-(3-chloro-5-fluorophenyl)-5-pentylpyrimidine. (Yield: 72.8%)

This product was used for the subsequent reaction without further purification.

(Second step) Preparation of 2-(3-chloro-5-fluoro-4-iodophenyl)-5-pentylpyrimidine 2-(3-Chloro-5-fluoro-4-iodophenyl)-5-pentylpyrimidine in an amount of 14.3 g was obtained by the same method as in the second step of Example 1 with the exception that 11.0 g (39.5 mmol) of the 2-(3-chloro-5-fluorophenyl)-5-pentylpyrimidine obtained in the previous step was used in place of the 4-propoxycyclohexyl-3-chloro-5-fluorobenzene used in the second step of Example 1. (Yield: 89.3%)

This product was used for the subsequent reaction without further reaction.

(Third step) Preparation of 2-(2-chloro-3',5',6-trifluoro-4'-trifluoromethoxybiphenyl-4-yl)-5-pentylpyrimidine Crude 2-(2-chloro-3',5',6-trifluoro-4'-trifluoromethoxybiphenyl-4-yl)-5-pentylpyrimidine in an amount of 2.9 g was obtained by the same method as Example 2 with the exception that 3 g (7.4 mmol) of the 2-(3-chloro-5-fluoro-4-iodophenyl)-5-pentylpyrimidine obtained in the previous step was used in place of the 4-propylcyclohexyl-3-chloro-5-fluoro-4-iodobenzene used in Example 2, and that 2.3 g (9.6 mmol) of dihydroxy(3,5-difluoro-4-trifluromethoxyphenyl)borane was used in place of dihydroxy(3,4-difluorophenyl)borane.

This product was recrystallized from a mixed solvent of ethanol/ethyl acetate to obtain 2.1 g of the subject compound.

(Yield: 60.0%)

$^1$H-NMR (CDCl$_3$, TMS internal standard)

δ (ppm)

0.91 (t, 3H)

1.33–1.89 (m, 6H)

2.65 (t, 2H)

5 7.99–8.32 (m, 4H)

8.60 (s, 2H)

By a method similar to that of Example 7, the following compounds can be prepared:

Compound No. 242: 3-PyB(3Cl, 5F)-F
Compound No. 243: 5-PyB(3Cl, 5F)-C
Compound No. 244; 2-PyB(2F, 3Cl)-3
Compound No. 245: 2O-Pr(3)B(3Cl, 5F)-CF$_3$
Compound No. 246: 5-Pr(3)B(2, 3Cl)-3
Compound No. 247: 3O1-PyB(3Cl, 5F)B(3F)-CF$_2$H
Compound No. 248: 4-PyB(3F)B(3, 5Cl)-OCF$_2$H
Compound No. 249: 6-B(3, 5F)PyB(3Cl)-OCH$_2$CF$_2$H
Compound No. 250: 8-B(3, 5F)B(3Cl, 5F)Py-F
Compound No. 251: 7-B(3Cl, 5F)2PyB(3, 5F)-C
Compound No. 252: 9-Pr(3)B(3, 5Cl)-B(3F)-OCF$_3$
Compound No. 253: 1-Pr(2)B(2Cl)B(2, 3F)-O5
Compound No. 254: 4O6-B(2Cl, 3F)Pr(3)B(2F, 3Cl)-2
Compound No. 255: 4O-Pr(3)2B(3Cl, 5F)B-OCF$_3$
Compound No. 256: 3-B(3Cl, 5F)B(3, 5F)2Pr(3)-CL
Compound No. 257: 5-HPyB(3Cl, 5F)-CFH$_2$
Compound No. 258: 2O-HPr(3)B(3Cl, 5F)-F
Compound No. 259: 5-HPr(2)B(2, 3Cl)-3
Compound No. 260: 5-HHPyB(3Cl, 5F)-OCF$_2$CH$_2$CF$_3$
Compound No. 261: 4-HHPyB(2F, 3Cl)-O2
Compound No. 262: 5-HHPr(3)B(3Cl, 5F)-CF$_2$H
Compound No. 263: 3-HHPr(2)B(2, 3Cl)-O3
Compound No. 264: 3-HHB(3, 5Cl)2Py-CF$_3$
Compound No. 265: 3O-HH2PyB(3Cl, 5F)-C
Compound No. 266: 3O1-HH4Pr(3)B(2Cl, 3F)-3
Compound No. 267: F5V-HPyB(3, 5Cl)B(3F)-CL
Compound No. 268: 5-HB(3Cl, 5F)PyB(3, 5F)-OCF$_3$
Compound No. 269: 1V-HP(3)B(2,3F)B(2Cl,3F)-O2
Compound No. 270: 1O4-H2PyB(3Cl)B(3, 5F)-OCF$_2$H
Compound No. 271: FFV2-H2Pr(2)B(2, 3F)B(2, 3Cl)-3
Compound No. 272: 3(2)1-HB(3, 5Cl)2PyB(3F)-OCF$_2$CF$_2$H
Compound No. 273: 2-PyB(3, 5F)B(3Cl)B(3, 5F)-CF$_2$H
Compound No. 274: 12O-B(3Cl)B(3Cl)PyB(3Cl, 5F)-CFH$_2$
Compound No. 275: 11O5-B(3F)2PyB(3Cl, 5F)B-OCF$_3$
Compound No. 276: 4-B(3Cl, 5F)B(3Cl, 5F)2PyB-C
Compound No. 277: F2-BB(2F, 3Cl)B(2Cl, 3F)4Pr(2)-3

EXAMPLE 8

Preparation of trans-2-(3-chloro-5-fluoro-4-trifluoromethylphenyl)-5-propyltetrahydropyran (3-P(3)B(3Cl,5F)-CF$_3$ (Compound No. 278))

(First step) Preparation of 6-(3-chloro-5-fluoro-4-trifluoromethylphenyl)-3-propyltetrahydro-2-pyrone A solution of 12.0 g (31.2 mmol) of ethyl=5-(3-chloro-5-fluoro-4-trifluoromethylphenyl)-5-hydroxy-2-propylpentanoate [prepared by reacting 3-propyl-5-formylpentanoic acid with 3-chloro-5-fluoro-4-trifluromethylphenylmagnesium bromide], 25 ml of a concentrated hydrochloric acid, and 100 ml of ethanol was heated at 50° C. while being stirred for 3 hours. To the reaction solution was added 50 ml of toluene, and the organic layer thus obtained was washed with a diluted aqueous sodium bicarbonate solution thrice and water thrice, and then dried over anhydrous magnesium sulfate. The solvent was distilled off under a reduced pressure and the residue was subjected to silica gel chromatography (eluent: heptane/toluene=1/1) to obtain 7.7 g of a crude 6-(3-chloro-5-fluoro-4-trifluoromethylphenyl)-3-propyltetrahydro-2-pyrone. (Yield: 73.3%)

This product was used for the subsequent reaction without further purification.

(Second step) Preparation of trans-2-(3-chloro-5-fluoro-4-trifluoromethylphenyl)-5-propyltetrahydropyran A mixture of 7.7 g (22.7 mmol) of the 6-(3-chloro-5-fluoro-4-trifluoromethylphenyl)-3-propyltetrahydro-2-pyrone, 13.2 g (113.6 mmol) of triethylsilane, and 50 ml of trifluoroacetic acid was stirred at room temperature for 1 hour. After termination of the reaction, 30 ml of water was added to the reaction solution and extracted with 50 ml of toluene. The organic layer thus obtained was washed with a diluted aqueous sodium bicarbonate solution thrice and water thrice, and then dried over anhydrous magnesium sulfate. The solvent was distilled off under a reduced pressure and the residue was subjected to silica gel column chromatography (eluent: heptane/toluene=9/1) to obtain 6.6 g of a crude trans-2-(3-chloro-5-fluoro-4-trifluoromethylphenyl)-5-propyltetrahydropyran.

This product was recrystallized from a mixed solvent of ethanol/ethyl acetate to obtain 2.1 g of the subject compound. (yield: 28.7%)

By a method similar to that of Example 8, the following compounds can be prepared:
Compound No. 279: 5-P(3)B(2, 3Cl)-O2
Compound No. 280: 5-P(3)HB(3Cl, 5F)-C
Compound No. 281: 12-HP(3)B(2Cl, 3F)-1O3
Compound No. 282: 2-P(3)2HB(3Cl, 5F)-F
Compound No. 283: 2-HP(2)2B(2Cl, 3F)-5
Compound No. 284: 4-P(3)B(3, 5Cl)B(3F)-CL
Compound No. 285: 6-B(2, 3F)P(2)B(2, 3Cl)-O5
Compound No. 286: 8-P(3)B(3Cl)B(3, 5F)-OCF$_3$
Compound No. 287: 3O-P(3)2B(2F, 3Cl)B(2, 3F)-O5
Compound No. 288: F4-B(3Cl, 5F)B(3Cl, 5F)2P(3)-CF$_3$
Compound No. 289: 2V3V-P(3)HHB(3Cl, 5F)-C
Compound No. 290: 4-P(2)HH2B(2, 3Cl)-3
Compound No. 291: 4-HP(3)4HB(2Cl, 3F)-1
Compound No. 292: 3-P(3)HB(3, 5Cl)B(3, 5F)-CF$_2$CH$_2$CF$_3$
Compound No. 293: 4O-P(3)HB(3, 5F)2B(3Cl)-F
Compound No. 294: 1O3-HP(3)2B(3Cl, 5F)B(3Cl)-OCF$_2$H
Compound No. 295: 5-P(3)B(3Cl)B(2, 3Cl)B(3Cl)-CL
Compound No. 296: 3(FF)1-P(3)B(2, 3F)B2B(2F, 3Cl)-5
Compound No. 297: 7-P(3)2B(3F)B(3Cl, 5F)B(3, 5F)-OCF$_3$

EXAMPLE 9

Preparation of trans-4-(trans-4-(2-(2-chloro-3-fluoro-4-methylphenyl)ethyl)cyclohexyl)-1-propyl-1-silacyclohexane (3-Si(1)H2B(2Cl,3F)-1 (Compound No. 298))

To a solution of 5.0 g (12.9 mmol) of 1-chloro(trans-4-(2-(2-chloro-3-fluoro-4-methylphenyl)ethyl)cyclohexyl)-1-silacyclohexane [prepared by using 3-(trans-4-(2-(2-chloro-3-fluoro-4-methylphenyl)ethyl)cyclohexyl)pentyl-bis-1,5-magnesium bromide and trichlorosilane by a method similar to that described in Laid-open Japanese Patent Publication No. Hei 7-112990) in 50 ml of THF was added by drops 14 ml of propylmagnesium bromide (1M, THF solution, corresponding to 14.2 mmol) at room temperature. After finishing of the dropping, it was heated at 40° C. while being stirred for 3 hours. To the reaction solution was added 15 ml of a diluted hydrochloric acid and extracted with 100 ml of heptane. The organic layer thus obtained was washed with a diluted aqueous sodium bicarbonate solution thrice and water thrice, and then dried over anhydrous magnesium sulfate. The solvent was distilled off under a reduced pressure and the residue was subjected to silica gel column chromatography (eluent: heptane) to obtain 3.8 g of a crude trans-4-(trans-4-(2-(2-chloro-3-fluoro-4-methylphenyl)ethyl)cyclohexyl)-1-propyl-1-silacyclohexane.

This product was recrystallized from a mixed solvent of a ws ethanol/ethyl acetate to obtain 1.9 g of the subject compound. (Yield: 37.2%)

By a method similar to that of Example 9, the following compounds can be prepared:
Compound No. 299: 3-Si(1)B(3Cl, 5F)-C
Compound No. 300: 5-Si(4)B(2F, 3Cl)-O2
Compound No. 301: 5-Si(1)HB(3Cl, 5F)-OCH$_2$CF$_2$H
Compound No. 302: 2O-HSi(1)B(2, 3Cl)-3
Compound No. 303: 5O-HSi(4)2B(3Cl, 5F)-CL
Compound No. 304: 2-Si(1)2HB(3, 5Cl)-CF$_3$
Compound No. 305: 1V-Si(1)VHB(2Cl, 3F)-2
Compound No. 306: 2-(1)4Si(1)B(2Cl, 3F)-O3
Compound No. 307: F5-Si(4)B(3, 5Cl)B(3F)-OCF$_3$
Compound No. 308: 4-Si(4)B(3Cl)B(2, 3F)-O2
Compound No. 309: 4-Si(1)B(3Cl)2B(3Cl, 5F)-OCF$_2$H
Compound No. 310: 3-Si(1)2B(3F)B(3Cl, 5F)-CF$_2$H
Compound No. 311: 1-Si(4)2B(2, 3F)B(3Cl)-F
Compound No. 312: 3-Si(1)HHB(3Cl, 5F)-CF$_3$
Compound No. 313: 2V-HHSi(4)B(3Cl, 5F)-CL
Compound No. 314: 5-HSi(1)H2B(2Cl, 3F)-3
Compound No. 315: 5-Si(1)H2HB(3, 5Cl)-OCF$_3$
Compound No. 316: 4-Si(1)Si(1)2HB(2Cl, 3F)-O2
Compound No. 317: 4-Si(4)HB(3, 5Cl)B(3F)-F
Compound No. 318: 3O-Si(4)Si(4)B(2, 3Cl)B(2, 3F)-O2
Compound No. 319: 3-Si(1)HB(3Cl, 5F)2B(3F)-CL
Compound No. 320: 2-HSi(4)2B(3F)B(3Cl, 5F)-OCF$_2$CH$_2$CF$_3$
Compound No. 321: 2-Si(4)Si(4)2B(3Cl)B(2, 3F)-O3
Compound No. 322: 7-Si(1)B B(3Cl, 5F)B(3F)-CF$_2$H
Compound No. 323: 7-Si(4)B(3F)B(3Cl, 5F)B(3, 5F)-OCF$_3$
Compound No. 324: 3-Si(1)BB(3Cl)B(3, 5F)-O2
Compound No. 325: 4-Si(1)B(3Cl)2B(3Cl, 5F)B-CF$_3$
Compound No. 326: 2-Si(4)2BB(2Cl, 3F)B(2Cl, 3F)-5
Compound No. 327: 5-Si(1)B(3, 5Cl)B(3, 5F)H-4
Compound No. 328: 5-Si(1)B(3C)B(2Cl)Si(4)-3
Compound No. 329: 5-Si(4)B(2Cl)B(3, 5F)Si(1)-2

EXAMPLE 10 (USE EXAMPLE 2)

Physical properties of the liquid crystal composition of Composition Example 1 were as follows:

NI: 83.4, Δ∈: 8.7, Δn: 0.161, η: 21.2, Vth: 1.90

While this liquid crystal composition was left in a freezer at −20° C., development of smectic phase or separation of crystals la was not observed over 60 days.

Pitch of the liquid crystal composition prepared by dissolving 0.8 part of optically active compound CM-33 to 100 parts of the liquid crystal composition of this Example was 10.6 μm

EXAMPLE 11 (USE EXAMPLE 3)

Physical properties of the liquid crystal composition of Composition Example 2 were as follows:

NI: 94.3, Δ∈: 6.7, Δn: 0.200, η: 37.0, Vth: 2.22

While this liquid crystal composition was left in a freezer at −20° C., development of smectic phase or separation of crystals was not observed over 60 days.

EXAMPLE 12 (USE EXAMPLE 4)

Physical properties of the liquid crystal composition of Composition Example 3 were as follows:

NI: 71.8, Δ∈: 25.7, Δn: 0.119, η: 44.0, Vth: 0.92

While this liquid crystal composition was left in a freezer at −20° C., development of smectic phase or separation of crystals was not observed over 60 days.

EXAMPLE 13 (USE EXAMPLE 5)

Physical properties of the liquid crystal composition of Composition Example 4 were as follows:

NI: 88.2, $\Delta\epsilon$: 6.6, $\Delta n$: 0.117, $\eta$: 21.4, Vth: 2.18

While this liquid crystal composition was left in a freezer at −20° C., development of smectic phase or separation of crystals was not observed over 60 days.

EXAMPLE 14 (USE EXAMPLE 6)

Physical properties of the liquid crystal composition of Composition Example 5 were as follows:

NI: 100.2, $\Delta\epsilon$: 7.5, $\Delta n$: 0.200, $\eta$: 17.6, Vth: 1.98

While this liquid crystal composition was left in a freezer at −20° C., development of smectic phase or separation of crystals was not observed over 60 days.

EXAMPLE 15 (USE EXAMPLE 7)

Physical properties of the liquid crystal composition of Composition Example 6 were as follows:

NI: 78.1, $\Delta\epsilon$: 7.8, $\Delta n$: 0.137, $\eta$: 18.8, Vth: 1.91

While this liquid crystal composition was left in a freezer at −20° C., development of smectic phase or separation of crystals was not observed over 60 days.

EXAMPLE 16 (USE EXAMPLE 8)

Physical properties of the liquid crystal composition of Composition Example 7 were as follows:

NI: 84.7, $\Delta\epsilon$: 4.9, $\Delta n$: 0.102, $\eta$: 26.1, Vth: 2.31

While this liquid crystal composition was left in a freezer at −20° C., development of smectic phase or separation of crystals was not observed over 60 days.

Pitch of the liquid crystal composition prepared by dissolving 0.3 part of optically active compound CN to 100 parts of the liquid crystal composition of this Example was 80 $\mu$m.

EXAMPLE 17 (USE EXAMPLE 9)

Physical properties of the liquid crystal composition of Composition Example 8 were as follows:

NI: 71.5, $\Delta\epsilon$: 13.8, $\Delta n$: 0.089, $\eta$: 39.9, Vth: 1.32

While this liquid crystal composition was left in a freezer at −20° C., development of smectic phase or separation of crystals was not observed over 60 days.

EXAMPLE 18 (USE EXAMPLE 10)

Physical properties of the liquid crystal composition of Composition Example 9 were as follows:

NI: 88.0, $\Delta\epsilon$: 6.3, $\Delta n$: 0.131, $\eta$: 27.8, Vth: 2.05

While this liquid crystal composition was left in a freezer at −20° C., development of smectic phase or separation of crystals was not observed over 60 days.

EXAMPLE 19 (USE EXAMPLE 11)

Physical properties of the liquid crystal composition of Composition Example 10 were as follows:

NI: 87.2, $\Delta\epsilon$: 4.5, $\Delta n$: 0.101, $\eta$: 24.1, Vth: 2.07, VHR: 98.4, 97.2, 96.7

While this liquid crystal composition was left in a freezer at −20° C., development of smectic phase or separation of crystals was not observed over 60 days.

EXAMPLE 20 (USE EXAMPLE 12)

Physical properties of the liquid crystal composition of Composition Example 11 were as follows:

NI: 70.8, $\Delta\epsilon$: 8.4, $\Delta n$: 0.102, $\eta$: 25.1, Vth: 1.72

While this liquid crystal composition was left in a freezer at −20° C., development of smectic phase or separation of crystals was not observed over 60 days.

EXAMPLE 21 (USE EXAMPLE 13)

Physical properties of the liquid crystal composition of Composition Example 12 were as follows:

NI: 68.0, $\Delta\epsilon$: −1.8, $\Delta n$: 0.090, $\eta$: 27.5

While this liquid crystal composition was left in a freezer at −20° C., development of smectic phase or separation of crystals was not observed over 60 days.

EXAMPLE 22 (USE EXAMPLE 14)

Physical properties of the liquid crystal composition of Composition Example 13 were as follows:

NI: 84.2, $\Delta\epsilon$: −4.2, $\Delta n$: 0.086

While this liquid crystal composition was left in a freezer at −20° C., development of smectic phase or separation of crystals was not observed over 60 days.

EXAMPLE 23 (COMPARATIVE EXAMPLE 1)

Physical properties of liquid crystal composition (C) which was prepared by the same method as Example 3 with the exception that 4'-(trans-4-propylcyclohexyl)-2',6',3,4-tetrafluorobiphenyl which is a compound having the same structure as the compound of Compound No. 19 except that chlorine atom is replaced by fluorine atom and described in Tokuhyo (Laid-open Japanese WO publication) No. Hei 6-504032 was used in place of the 4'-(trans-4-propylcyclohexyl)-2'-chloro-3,4,6'-trifluorobiphenyl (Compound No. 19) were as follows:

NI: 64.3, $\Delta\epsilon$: 11.8, $\Delta n$: 0.132, $\eta$: 29.6, Vth: 1.57

From this fact, it was found out that the compound of the present invention, 4'-(trans-4-propylcyclohexyl)-2'-chloro-3,4,6'-trifluorobiphenyl (Compound No. 19) has a low $\Delta n$ and low threshold voltage compared with known fluorine type compounds.

EXAMPLE 24 (COMPARATIVE EXAMPLE 2)

When liquid crystal composition (D) which was prepared by dissolving 5% of 4'"-propyl-2",2',6',3,4-pentafluoroquaterphenyl which has the same structure as the compound of the present invention, 4'"-propyl-2'-chloro-2", 6',3,4-tetrafluoroquaterphenyl (compound No. 88) except that chlorine atom is replaced by fluorine atom, and 95% of the liquid crystal composition (A) used in Example 3 at 100° C. each other was allowed to cool to room temperature, crystals separated.

On the other hand, a mixture of 15% of the compound of the present invention, 4'"-propyl-2'-chloro-2",6',3,4-tetrafluroquaterphenyl (Compound No. 88) with 85% of liquid crystal composition (A) readily dissolved at room temperature. From this fact, it was found out that chlorine substituted compounds of the present invention are remarkably excellent in miscibility compared with chlorine unsubstituted compounds.

EXAMPLE 25 (COMPARATIVE EXAMPLE 3)

Physical properties of liquid crystal composition (E) which has the same chemical composition as Composition Example 12 with the exception that (trans-4-(2-(trans-4-ethylcyclohexyl)ethyl)-cyclohexyl)-4-ethoxy-2,3-difluorobenzene (3-H2HB(2,3F)-O2) which is a compound described in Tokuhyo (Laid-open Japanese WO publication) No. Hei 2-503441 is used in the composition instead of the 4'-(2-(trans-4-propylcyclohexyl)ethyl)-2-chloro-2',3',3-trifluoro-4-methylbiphenyl (Compound No. 40) used in Composition Example 12 were as follows:

NI: 64.8, Δ∈: −1.7, Δn: 0.092, η: 24.8

From this fact, it was found out that the compounds of the present invention have a high Δ∈ and a low Δn compared with known compounds.

EXAMPLE 26 (COMPARATIVE EXAMPLE 4)

Physical properties of liquid crystal composition (F) which has the same chemical composition as Composition Example 12 with the exception that 4,4'-dimethyl-2,2",3,3"-tetrafluoroterphenyl (1-B(2,3F)BB(2,2F)-1) which is a compound described in DE 3,839,213 A1 is used in the composition instead of the 4'-(2-(trans-4-propylcyclohexyl)ethyl)-2-chloro-2',3',3-trifluoro-4-methylbiphenyl (compound No. 40) used in Composition Example 12 were as follows:

NI: 74.6, Δ∈: −1.6, Δn: 0.095, η: 26.7

When this liquid crystal composition (F) was left in a freezer at −20° C., smectic phase occurred after 5 days.

From this fact, it was found out that the compounds of the present invention have a high Δ∈, a low Δn, and a good miscibility even at low temperatures compared with known compounds.

Liquid crystalline compounds of the present invention have an extremely high voltage holding ratio and a low threshold voltage, are considerably low in their dependency on temperature, have a low Δn, and are improved in miscibility with other liquid crystal materials besides. Further, novel liquid crystalline compounds having desired physical properties can be provided by selecting proper substituents therein.

INDUSTRIAL APPLICABILITY

Accordingly, novel liquid crystal compositions which have an extremely high voltage holding ratio, are considerably low in its dependency on temperature, have a low threshold voltage, a proper value of Δn and Δ∈, and are excellent in stability, and miscibility with other liquid crystal materials can be provided by using the liquid crystalline compound of the present invention as component of liquid crystal compositions. Further, excellent liquid crystal display devices of in-plane switching (IPS) mode or vertical alignment (VA) mode can be provided by using the liquid crystal composition.

What is claimed is:

1. A chlorobenzene derivative expressed by the general formula (1)

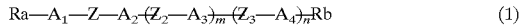

(1)

wherein Ra represents a straight chain or branched alkyl group having 1 to 20 carbon atoms in which group any methylene group (—CH$_2$) may be replaced by —O—, —CO—, —CH=CH—, —C≡C—, —SiH$_2$—, or cyclobutane-1,3-diyl, but in no case continues —O—, and in no case continue —O— and —CO—, and one or more hydrogen atoms in the Ra may be replaced by a halogen atom; Rb represents a group selected from the Ra, or a halogen atom; A$_1$, A$_2$, A$_3$, and A$_4$ independently represent trans-1,4-cyclohexylene or 1,4-phenylene in which ring any —CH$_2$— may be replaced by —O—, >CH— may be replaced by >SiH—, and —CH= may be represented by —N=, respectively, and one or two hydrogen atoms on the 1,4-phenylene may be replaced by a chlorine atom and/or fluorine atom provided that at least two rings among A$_1$, A$_2$, A$_3$ and A$_4$ are 1,4-phenylenes, and at least three hydrogen atoms among all hydrogen atoms on the 1,4-phenylenes are replaced by one chlorine atom and at least two fluorine atoms; Z$_1$, Z$_2$ and Z$_3$ independently represent single bond or an alkylene group having 1 to 4 carbon atoms in which group one or more hydrogen atoms may be replaced by a halogen atom, any methylene group (—CH$_2$—) in the alkylene group may be replaced by —O—, —CO—, —CH=CH—, —C≡C—, or —SiH$_2$— but in no case continues —O—, and in no case continue —O— and —CO—; and m is 1, and n is 0 or 1.

2. The chlorobenzene derivative according to claim 1 wherein n=0.

3. The chlorobenzene derivative according to claim 1 wherein n is 1.

4. A liquid crystal composition comprising at least two components, at least one of which is a chlorobenzene derivative defined in any one of claims 1 to 3.

5. A liquid crystal composition comprising, as a first component, at least one chlorobenzene derivative defined in any one of claims 1 to 3, as a second component, at least one compound selected from the group consisting of the compounds expressed by the general formulas (2), (3), and (4)

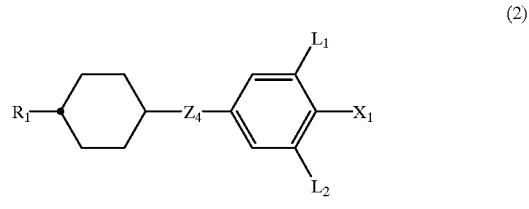

(2)

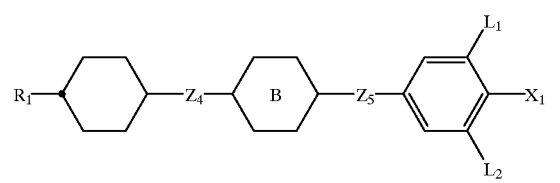

(3)

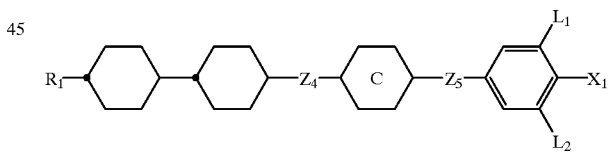

(4)

wherein R$_1$ represents an alkyl group having 1 to 10 carbon atoms in which group, any not-adjacent methylene group may be replaced by —O— or —CH=CH—, and any hydrogen atom in the alkyl group may be replaced by fluorine atom; X$_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; L$_1$ and L$_2$ independently represent hydrogen atom or fluorine atom; Z$_4$ and Z$_5$ independently represent 1,2-ethylene, 1,4-butylene, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; and ring C represents trans-1,4-cyclohexylene, or 1,4-phenylene in which hydrogen atom may be replaced by fluorine atom, and optionally, as a third component, at least one optically active compound.

6. A liquid crystal composition comprising, as a first component, at least one chlorobenzene derivative defined in any one of claims 1 to 3, as a second component, at least one compound selected from the group consisting of the compounds expressed by the general formulas (5) and (6)

(5)

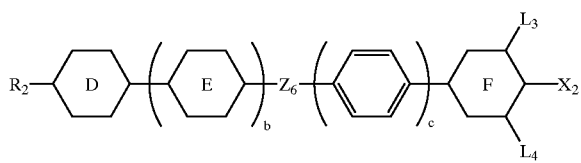

(6)

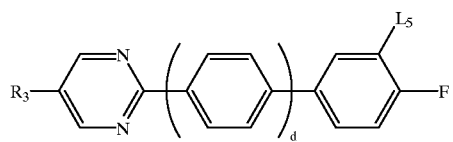

wherein $R_2$ and $R_3$ independently represent an alkyl group having 1 to 10 carbon atoms in which group, any not-adjacent methylene group may be replaced by —O— or —CH=CH—, and any hydrogen atom in the alkyl group may be replaced by fluorine atom; $X_2$ represents —CN group or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom may be replaced by fluorine atom, or pyrimidine-2,5-diyl; ring F represents trans-1,4-cyclohexylene or 1,4-phenylene; $Z_6$ represents 1,2-ethylene, —COO—, or single bond; $L_3$, $L_4$, and $L_5$ independently represent hydrogen atom or fluorine atom; and b, c, and d are independently 0 or 1, and optionally, as a third component, at least one optically active compound.

7. A liquid crystal composition comprising, as a first component, at least one chlorobenzene derivative defined in any one of claims 1 to 3, as a second component, at least one compound selected from the group consisting of the compounds expressed by the general formulas (7), (8), and (9)

(7)

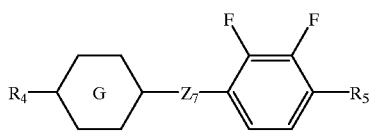

(8)

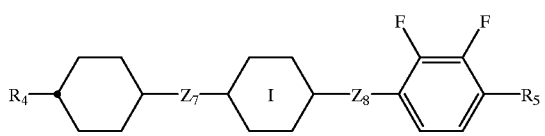

(9)

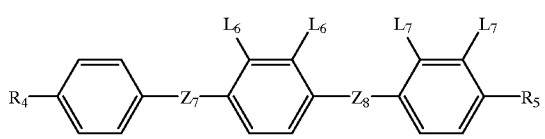

wherein $R_4$ and $R_5$ independently represent an alkyl group having 1 to 10 carbon atoms in which group, any not-adjacent methylene group may be replaced by —O— or —CH=CH—, and any hydrogen atom in the alkyl group may be replaced by fluorine atom; ring G and ring I independently represent trans-1,4-cyclohexylene or 1,4-phenylene; $L_6$ and $L_7$ independently represent hydrogen atom or fluorine atom but in no case represent both $L_6$ and $L_7$ hydrogen atom at the same time; and $Z_7$ and $Z_8$ independently represent 1,2-ethylene, —COO—, or single bond, and optionally, as a third component, at least one optically active compound.

8. A liquid crystal composition comprising, as a first component, at least one chlorobenzene derivative defined in any one of claims 1 to 3, as a second component, at least one compound selected from the group consisting of the compounds expressed by the general formulas (2), (3), and (4)

(2)

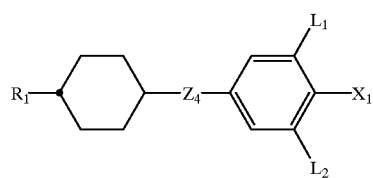

(3)

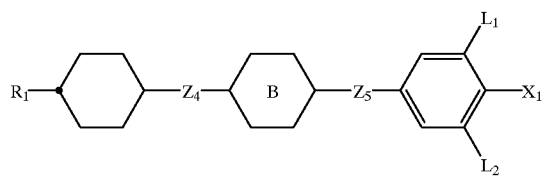

(4)

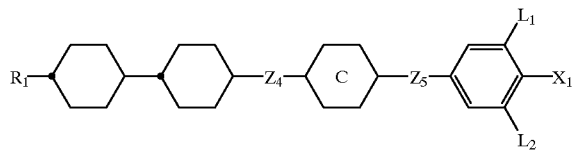

wherein $R_1$ represents an alkyl group having 1 to 10 carbon atoms in which group, any not-adjacent mnethylene group may be replaced by —O— or —CH=CH—, and any hydrogen atone in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_4$ and $Z_5$ independently represent 1,2-ethylene, 1,4-butylene, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; and ring C represents trans-1,4-cyclohexylene, or 1,4-phenylene in which hydrogen atom may be replaced by fluorine atom, as a third component, at least one compound selected from the group consisting of the compounds expressed by the general formulas (10), (11), and (12)

(10)

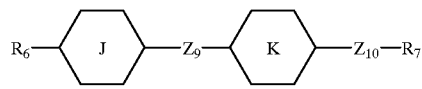

(11)

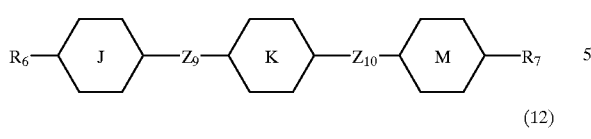

(12)

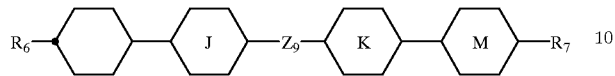

wherein $R_6$ and $R_7$ independently represent an alkyl group having 1 to 10 carbon atoms in which group, any not-adjacent methylene group may be replaced by —O— or —CH=CH—, and any hydrogen atom in this alkylgroup may be replaced by fluorine atom; ring J, ring K, and ring M independently represent trans-1,4-cyclohexylene or pyrimidine-2,5-diyl, or 1,4-phenylene in which hydrogen atom may be replaced by fluorine atom; and $Z_9$ and $Z_{10}$ independently represent 1,2-ethylene, —C≡C—, —COO—, —CH=CH—, or single bond, and optionally, as a fourth component, at least one optically active compound.

9. A liquid crystal composition comprising, as a first component, at least or chlorobenzene derivative defined in any one of claims 1 to 3, as a second component, at least one compound selected from the group consisting of the compounds expressed by the general formulas (5) and (6)

(5)

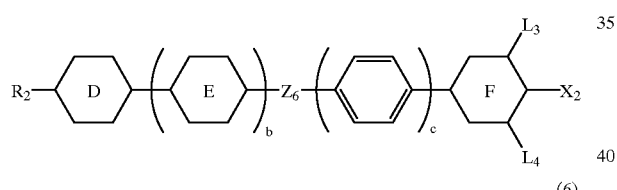

(6)

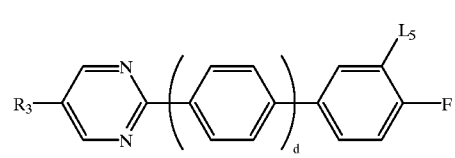

wherein $R_2$ and $R_3$ independently represent an alkyl group having 1 to 10 carbon atoms in which group, any not-adjacent methylene group may be replaced by —O— or —CH=CH—, and any hydrogen atom in the alkyl group may be replaced by fluorine atom; $X_2$ represents —CN group or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom may be replaced by fluorine atom, or pyrimidine-2,5-diyl; ring F represents trans-1,4-cyclohexylene or 1,4-phenylene; $Z_6$ represents 1,2-ethylene, —COO—, or single bond; $L_3$, $L_4$, and $L_5$ independently represent hydrogen atom or fluorine atom; and b, c, and d are independently 0 or 1, as a third component, at least one compound selected from the group consisting of the compounds expressed by the general formulas (10), (11), and (12)

(10)

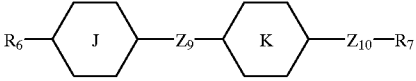

(11)

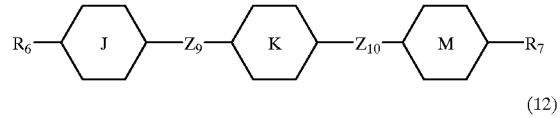

(12)

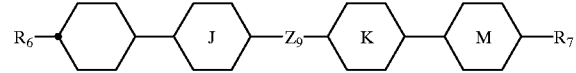

wherein $R_6$ and $R_7$ independently represent an alkyl group having 1 to 10 carbon atoms in which group, any not-adjacent methylene group may be replaced by —O— or —CH=CH—, and any hydrogen atom in this alkyl group may be replaced by fluorine atom; ring J, ring K, and ring M independently represent trans-1,4-cyclohexylene or pyrimidine-2,5-diyl, or 1,4-phenylene in which hydrogen atom may be replaced by fluorine atom; and $Z_9$ and $Z_{10}$ independently represent 1,2-ethylene, —C≡C—, —COO—, —CH=CH—, or single bond, and optionally, as a fourth component, at least one optically active compound.

10. A liquid crystal composition comprising, as a first component, at least one chlorobenzene derivative defined in any one of claims 1 to 3, as a second component, at least one compound selected from the group consisting of the compounds expressed by the general formulas (7), (8), and (9)

(7)

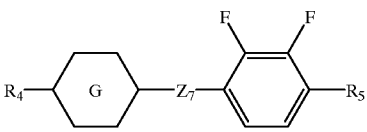

(8)

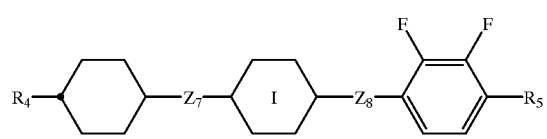

(9)

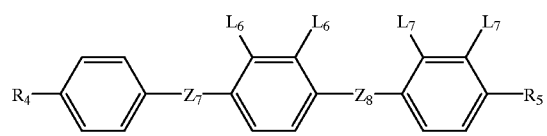

wherein $R_4$ and $R_5$ independently represent an alkyl group having 1 to 10 carbon atoms in which group, any not-adjacent methylene group may be replaced by —O— or —CH=CH—, and any hydrogen atom in the alkyl group may be replaced by fluorine atom; ring G and ring I independently represent trans-1,4-cyclohexylene or 1,4-phenylene; $L_6$ and $L_7$ independently represent hydrogen atom or fluorine atom but in no case represent both $L_6$ and $L_7$ hydrogen atom at the same time; and $Z_7$ and Z8 independently represent 1,2-ethylene, —COO—, or single bond, as a third component, at least one compound selected from the group consisting of the compounds expressed by the general formulas (10), (11), and (12)

(10)
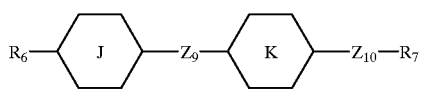

(11)
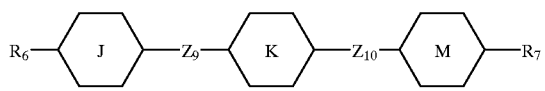

(12)
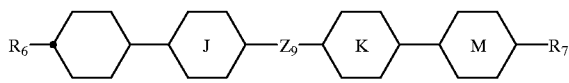

wherein $R_6$ and $R_7$ independently represent an alkyl group having 1 to 10 carbon atoms in which group, any not-adjacent methylene group may be replaced by —O— or —CH=CH—, and any hydrogen atom in his alkyl group may be replaced by fluorine atom; ring J, ring K, and ring M independently represent trans-1,4-cyclohexylene or pyrimidine-2,5-diyl, or 1,4-phenylene in which hydrogen atom may be replaced by fluorine atom; and $Z_9$ and $Z_{10}$ independently represent 1,2-ethylene, —C≡C—, —COO—, —CH=CH—, or single bond, and optionally, as a fourth component, at least one optically active compound.

11. A liquid crystal composition comprising, as a first component, at least one chlorobenzene derivative defined in any one of claims 1 to 3, as a second component, at least one compound selected from the group consisting of the compounds expressed by the general formulas (2), (3), and (4)

(2)
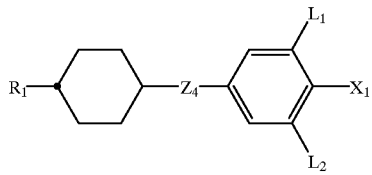

(3)
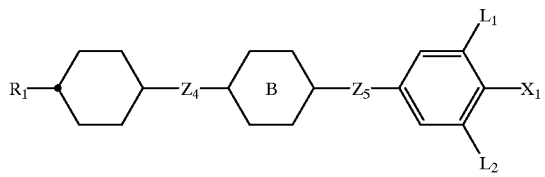

(4)
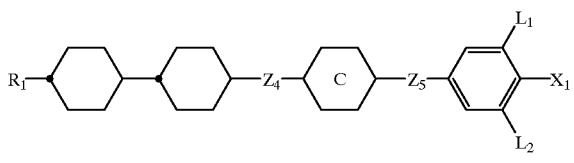

wherein $R_1$ represents an alkyl group having 1 to 10 carbon atoms in which group, any not-adjacent methylene group may be replaced by —O— or —CH=CH—, and any hydrogen atom in the alkyl group may be replaced by fluorine atom,; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$;

$L_1$ and $L_2$ independently represent hydrogen atom or fluorine atom;

$Z_4$ and $Z_5$ independently represent 1,2-ethylene, 1,4-butylene, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom;

and ring C represents trans-1,4-cyclohexylene, or 1,4-phenylene in which hydrogen atom may be replaced by fluorine atom, as a third component, at least one compound selected from the group consisting of the compounds expressed by the general formulas (5) and (6)

(5)
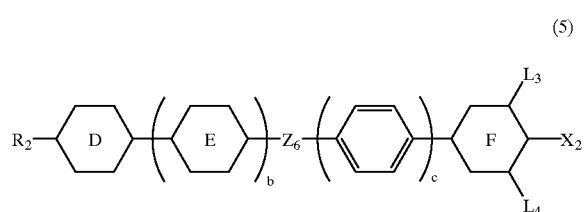

(6)
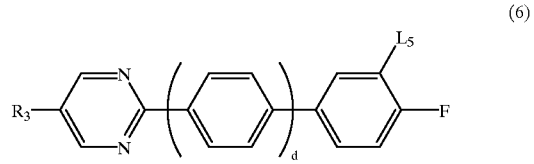

wherein $R_2$ and $R_3$ independently represent an alkyl group having 1 to 10 carbon atoms in which group, any not-adjacent methylene group may be replaced by —O— or —CH=CH—, and any hydrogen atom in the alkylgroup may be replaced by fluorine atom; $X_2$ represents —CN group or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene, 1,4-phenylene in which hydrogen atom may be replaced by fluorine atom, or pyrimidine-2,5-diyl; ring F represents trans-1,4-cyclohexylene 1,4-phenylene; $Z_6$ represents 1,2-ethylene, —COO—, or single bond; $L_3$, $L_4$, and $L_5$ independently represent hydrogen atom or fluorine atom; and b, c, and d are independently 0 or 1, as a fourth component, at least one compound selected from the group consisting of the compounds expressed by the general formulas (10), (11), and (12)

(10)
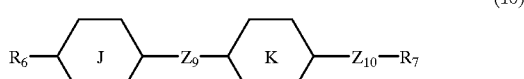

(11)
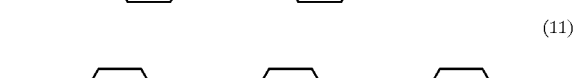

(12)
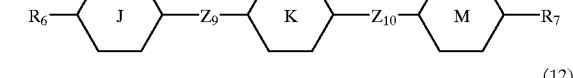

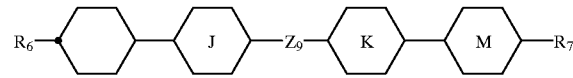

wherein $R_6$ and $R_7$ independently represent an alkyl group having 1 to 10 carbon atoms in which group, any not-adjacent methylene group may be replaced by —O— or —CH=CH—, and any hydrogen atom ir this alkyl group may be replaced by fluorine atom; ring J, ring K, and ring M independently represent trans-1,4-cyclohexylene or pyrimidine-2,5-diyl, or 1,4-phenylene in which hydrogen atom may be replaced by fluorine atom; and $Z_9$ and $Z_{10}$ independently represent 1,2-ethylene, —C≡C—, —COO—, —CH=CH—, or single bond, and optionally, as a fifth component, at least one optically active compound.

12. A liquid crystal display device comprising the liquid crystal composition defined in claim 4.